United States Patent
Easley, IV et al.

(10) Patent No.: US 11,939,593 B2
(45) Date of Patent: Mar. 26, 2024

(54) COMPOSITIONS AND METHODS FOR IMPROVING EMBRYO DEVELOPMENT

(71) Applicants: University of Georgia Research Foundation, Inc., Athens, GA (US); Emory University, Atlanta, GA (US)

(72) Inventors: Charles A. Easley, IV, Athens, GA (US); Anthony W. S. Chan, Atlanta, GA (US)

(73) Assignees: UNIVERSITY OF GEORGIA RESEARCH FOUNDATION, INC., Athens, GA (US); EMORY UNIVERSITY, Atlanta, GA (US)

( * ) Notice: Subject to any disclaimer, the term of this patent is extended or adjusted under 35 U.S.C. 154(b) by 519 days.

(21) Appl. No.: 17/265,157

(22) PCT Filed: Aug. 1, 2019

(86) PCT No.: PCT/US2019/044589
§ 371 (c)(1),
(2) Date: Feb. 1, 2021

(87) PCT Pub. No.: WO2020/028617
PCT Pub. Date: Feb. 6, 2020

(65) Prior Publication Data
US 2021/0340493 A1 Nov. 4, 2021

Related U.S. Application Data

(60) Provisional application No. 62/713,182, filed on Aug. 1, 2018.

(51) Int. Cl.
*C12N 5/073* (2010.01)
*C12N 5/076* (2010.01)
*C12N 15/90* (2006.01)

(52) U.S. Cl.
CPC ........... *C12N 5/0604* (2013.01); *C12N 5/061* (2013.01); *C12N 15/90* (2013.01); *C12N 2506/02* (2013.01); *C12N 2506/45* (2013.01); *C12N 2510/00* (2013.01); *C12N 2517/10* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton |
| 5,142,047 A | 8/1992 | Summerton |
| 5,166,315 A | 11/1992 | Summerton |
| 5,217,866 A | 6/1993 | Summerton |
| 5,356,802 A | 10/1994 | Chandrasegaran |
| 5,436,150 A | 7/1995 | Chandrasegaran |
| 5,487,994 A | 1/1996 | Chandrasegaran |
| 5,506,337 A | 4/1996 | Summerton |
| 5,521,063 A | 5/1996 | Summerton |
| 5,527,675 A | 6/1996 | Coull |
| 5,539,082 A | 7/1996 | Nielsen |
| 5,623,049 A | 4/1997 | Loebberding |
| 5,698,685 A | 12/1997 | Summerton |
| 5,714,331 A | 2/1998 | Buchardt |
| 5,736,336 A | 4/1998 | Buchardt |
| 5,773,571 A | 6/1998 | Nielsen |
| 5,786,571 A | 7/1998 | Bethel |
| 6,140,081 A | 10/2000 | Barbas |
| 6,453,242 B1 | 9/2002 | Eisenberg |
| 6,534,261 B1 | 3/2003 | Cox, III et al. |
| 6,610,512 B1 | 8/2003 | Barbas |
| 6,746,838 B1 | 6/2004 | Choo |

(Continued)

FOREIGN PATENT DOCUMENTS

| | | |
|---|---|---|
| EP | 0502976 | 9/1992 |
| WO | 9853059 | 11/1998 |

(Continued)

OTHER PUBLICATIONS

Boettcher M, McManus MT. Choosing the Right Tool for the Job: RNAi, TALEN, or CRISPR. Mol Cell. May 21, 2015;58(4):575-85. doi: 10.1016/j.molcel.2015.04.028. PMID: 26000843; PMCID: PMC4441801. (Year: 2015).*

Han C, Deng R, Mao T, Luo Y, Wei B, Meng P, Zhao L, Zhang Q, Quan F, Liu J, Zhang Y. Overexpression of Tet3 in donor cells enhances goat somatic cell nuclear transfer efficiency. FEBS J. Jul. 2018;285(14):2708-2723. doi: 10.1111/febs.14515. Epub Jun. 8, 2018. PMID: 29791079. (Year: 2018).*

Bahadur, "Fertility issues for cancer patients", Mol Cell Endocrinol., 169:117-5 (2000).

(Continued)

*Primary Examiner* — Allison M Fox
*Assistant Examiner* — Alyssa G Weston
(74) *Attorney, Agent, or Firm* — PABST PATENT GROUP LLP

(57) ABSTRACT

Compositions and methods for improving embryo development, treating idiopathic male factor infertility, and enabling infertile/sub-fertile/sterile men to father their own genetic offspring are provided. Typically, the methods include administering into a male or female gamete or fertilized embryo an effective amount of a compound that increases bioavailability of a TET protein to improve development of an embryo resulting from fertilization of the female gamete by a male gamete. The compound can be administered into the gamete or embryo before, during, or after fertilization. The compound can be administered by an injection such as intracytoplasmic injection. The compound and the male gamete can be administered in combination by intracytoplasmic sperm injection. Methods of making male gametes, and methods of modifying the genome of a male gamete or embryo using an effective amount of a gene editing composition to correct a gene mutation or anomaly in the genome thereof are also provided.

20 Claims, 14 Drawing Sheets

Specification includes a Sequence Listing.

(56) References Cited

U.S. PATENT DOCUMENTS

| | | | |
|---|---|---|---|
| 6,866,997 | B1 | 3/2005 | Choo |
| 7,067,617 | B2 | 6/2006 | Barbas, III et al. |
| 2002/0165356 | A1 | 11/2002 | Barbas |
| 2004/0197892 | A1 | 10/2004 | Moore |
| 2007/0154989 | A1 | 7/2007 | Barbas |
| 2007/0213269 | A1 | 9/2007 | Barbas |
| 2011/0145940 | A1 | 6/2011 | Voytas |
| 2011/0236894 | A1 | 9/2011 | Rao |
| 2016/0186207 | A1 | 6/2016 | Reik |

FOREIGN PATENT DOCUMENTS

| | | | | |
|---|---|---|---|---|
| WO | | 2003016496 | | 2/2003 |
| WO | | 2010037001 | | 4/2010 |
| WO | | 2011072246 | | 6/2011 |
| WO | WO-2012029957 | A1 * | 3/2012 | ......... A01K 67/0273 |
| WO | | 2013176772 | | 11/2013 |
| WO | | 2014018423 | | 1/2014 |
| WO | | 2014096800 | | 6/2014 |

OTHER PUBLICATIONS

Braasch, et al., "Locked nucleic acid (LNA): fine-tuning the recognition of DNA and RNA", Chem. Biol., 8(1):1-7 (2001).

Byrne, et al., "Producing primate embryonic stem cells by somatic cell nuclear transfer", Nature 450(7169):497-502 (2007).

Carillo, et al., "The Multiple Sequence Alignment Problem in Biology", SIAM. J. Applied Math., 48(5):1073-1082 (1988).

Cermak, et al, "Efficient design and assembly of custom TALEN and other TAL effector-based constructs for DNA targeting", Nucl. Acids Res., 39(12):e89, 11 pages (2011).

Chang, "Assisted reproductive technology in nonhuman primates", Methods Mol Biol, 770:337-363 (2011).

Chang, et al., "Modification of DNA ends can decrease end joining relative to homologous recombination in mammalian cells", Proc. Natl. Acad. Sci., 84:4959-4963 (1987).

Chitwood, et al., "Transcriptome profiling of individual rhesus macaque oocytes and preimplantation embryos", Biol Reprod, 97(3):353-364 (2017).

Cong, "Multiplex genome engineering using CRISPR/Cas systems", Science, 15:339(6121):819-823 (2013).

Dawlaty, et al., "Combined Deficiency of Tet1 and Tet2 Causes Epigenetic Abnormalities but Is Compatible with Postnatal Development", Developmental Cell, 24(3):310-323 (2013).

Deutsch, et al., "Sirolimus-associated infertility: case report and literature review of possible mechanisms", Am J Transplant, 7(10):2414-2421 (2007).

Duan, et al., "The dynanlic changes of DNA rnethylation in primordial genn cell differentiation", Gene, 591 (2): 305-213 (2016).

Easley IV, et al., "Assessing reproductive toxicity of two environmental toxicants with a novel in vitro human spermatogenic model", Stem Cell Res., 14(3):347-355 (2015).

Easley IV, et al., "Direct differentiation of human pluripotent stem cells into haploid spermatogenic cells", Cell Rep. 2(3):440-446 (2012).

Easley IV, et al., "Using Pluripotent Stem Cells to Treat Male-factor Infertility: Towards a Potential Regenerative Medicine Strategy", University of Georgia, Regenerative Bioscience Center, RBC Poster, (Mar. 8, 2018).

Ehmcke, et al., "Spermatogonial stem cells: questions, models and perspectives", Hum Reprod Update, 12:275-282 (2006).

Fayomi, et al., "Spermatogonial stem cells and spermatogenesis in mice, monkeys and men", Stem Cell Res, 29:207-214 (2018).

Fujimoto, et al., "Aberrant genomic imprinting in rhesus monkey embryonic stem cells", Stem Cells, 24(3):595-603 (2006).

Fujimoto, et al., "Development of a monkey model for the study of primate genomic imprinting", Mol. Hum. Reprod., 11(6):413-422 (2005).

Gao, et al., "De novo DNA methylation during monkey preimplantation embryogenesis", Cell Res, 27(4):526-539 (2017).

Gassei, et al., "Experimental methods to preserve male fertility and treat male factor infertility", Fertil Steril, 105(2):256-266 (2016).

Gu, et al. The role of Tet3 DNA dioxygenase in epigenetic reprogramming by oocytes, Nature, 477(7366): 606-610 (2011).

Guo, et al., "Active and passive demethylation of male and female pronuclear DNA in the mammalian zygote", Cell Stem Cell, 15(4):447-459 (2014).

Handel, et al., "Applying "gold standards" to in-vitro-derived germ cells", Cell, 157(6):1257-1261 (2014).

Hayashi, et al., "Reconstitution of the Mouse Germ Cell Specification Pathway in Culture by Pluripotent Stem Cells", Cell, 146(4):1-14 (2011).

International Search Report for PCT/US2019/044589 dated Dec. 17, 2019.

Jinek, et al., "A programmable dual-RNA-guided DNA endonuclease in adaptive bacterial immunity", Science, 337(6096):816-21 (2012).

Kee, et al., "Human DAZL, DAZ and BOULE genes modulate primordial germ-cell and haploid gamete formation", Nature, 462(7270):222-225 (2009).

Kim, et al., "Chimeric restriction endonuclease", Proc. Natl. Acad. Sci., 91(3):883-887 (1994a).

Kim, et al., "Insertion and deletion mutants of FokI restriction endonuclease", J. Biol. Chem., 269(50):31978-31982 (1994b).

Levine, et al., "Temporal trends in sperm count: a systematic review and meta-regression analysis", Hum Reprod Update, 23(6):646-659 (2017).

Li, et al., "Alteration of the cleavage distance of Fok I restriction endonuclease by insertion mutagenesis", Proc. Natl. Acad. Sci., 90(7):2764-2768 (1993).

Li, et al., "Functional domains in Fok I restriction endonuclease", Proc. Natl. Acad. Sci., 89(10): 4275-4279 (1992).

Liu, "Linking Telomere Regulation to Stem Cell Pluripotency", Trends in Genetics, 33(1): 16-33 (2017).

Long, et al., "ZF-CxxC domain-containing proteins, CpG islands and the chromatin connection", Biochem Soc Trans., 41(Pt 3): 727-740 (2013).

Louis, et al., "The prevalence of couple infertility in the United States from a male perspective: evidence from a nationally representative sample", Andrology, 1(5):741-748 (2013).

Meng, et al., "Sperm-induced oocyte activation in the rhesus monkey: nuclear and cytoplasmic changes following intracytoplasmic sperm injection", Hum Reprod., 12(5):1062-1068 (1997).

Messerschmidt, et al., "DNA methylation dynamics during epigenetic reprogramming in the germline and preimplantation embryos", Genes & Development, 28(8): 812-828 (2014).

Miller, et al., "A TALE nuclease architecture for efficient genome editing", Nature Biotechnol., 29(2): 143-148 (2011).

Nakamura, et al., "Codon usage tabulated from international DNA sequence databases: status for the year 2000", Nucl. Acids Res., 28(1):292 (2000).

Navara, "The sperm centrosome during fertilization in mammals: implications for fertility and reproduction", Reprod Fertil Dev., 7(4):747-754 (1995).

Navara, et al., "Pedigreed primate embryonic stem cells express homogeneous familial gene profiles", Stem Cells, 25(11):2695-2704 (2007).

Needleman, et al., "A general method applicable to the search for similarities in the amino acid sequence of two proteins", J. Mol. Biol., 48(3): 443-453 (1970).

Nehls, et al., "Two genetically separable steps in the differentiation of thymic epithelium", Science, 272(5263):886-889 (1996).

Ni, et al., "TET enzymes are successively expressed during human spermatogenesis and their expression level is pivotal for male fertility", Hum Reprod., 31(7):1411-24 (2016).

Panula, et al., "Human germ cell differentiation from fetal- and adult-derived induced pluripotent stem cells", Hum Mol Genet., 20(4):752-762 (2011).

Raab, et al., "A Comparative View on Human Somatic Cell Sources for iPSC Generation", Stem Cells International, vol. 2014, Article ID 768391, 12 pages, (2014).

(56) References Cited

OTHER PUBLICATIONS

Rasmussen, et al., "Role of TET enzymes in DNA methylation, development, and cancer", Genes Dev., 30(7): 733-750 (2016).
Schatten, et al., "LEGOs® and legacies of centrioles and centrosomes", EMBO reports, 16:1052-1054 (2015).
Schlegel, "Evaluation of male infertility", Minerva Ginecol., 61(4):261-283 (2009).
Shen, et al., "Tet3 and DNA replication mediate demethylation of both the maternal and paternal genomes in mouse zygotes", Cell Stem Cell, 15(4):459-71 (2014).
Simerly, et al., "Nuclear transfer in the rhesus monkey: opportunities and challenges", Cloning and Stem Cells, 5(4):319-331 (2003).
Simerly, et al., "The paternal inheritance of the centrosome, the cell's microtubule-organizing center, in humans, and the implications for infertility", Nat Med., 1(1):47-52 (1995).
Skrzypek, et al., "Azoospermia in a renal transplant recipient during sirolimus (rapamycin) treatment", Andrologia, 39:198-199 (2007).
Steves, et al., "Per- and polyfluoroalkyl substances impact human spermatogenesis in a stem-cell-derived model", Syst Biol Reprod Med., 64:225-239 (2018).
Steves, et al., "Ubiquitous Flame-Retardant Toxicants Impair Spermatogenesis in a Human Stem Cell Model", iScience, 3:161-176 (2018).
Stice, et al., "Nuclear Reprogramming in Nuclear Transplant Rabbit Embryos", Biol. Reprod., 39(3):657-664 (1988).
Stirchak, et al., "Uncharged Stereoregular Nucleic Acid Analogues. 1. Synthesis of a Cytosine-Containing Oligomer with Carbamate Internucleoside Linkages", Organic. Chem., 52(19):4202 (1987).
Stone, et al., "Embryo fragmentation as a determinant of blastocyst development in vitro and pregnancy outcomes following embryo transfer", Am J Obstet Gynecol., 192(6):2014-9 (2005).
Swann, et al., "A cytosolic sperm factor stimulates repetitive calcium increases and mimics fertilization in hamster eggs", Development, 110: 1295-1302 (1990).
Tanaka, et al., "Fourteen babies born after round spermatid injection into human oocytes", Proc Natl Acad Sci, 112:14629-14634 (2015).
Tanaka, et al., "Ninety babies born after round spermatid injection into oocytes: survey of their development from fertilization to 2 years of age", Fertil. Steril., 110(3):443-451 (2018).
Voo, et al., "Cloning of a mammalian transcriptional activator that binds unmethylated CpG motifs and shares a CXXC domain with DNA methyltransferase, human trithorax, and methyl-CpG binding domain protein 1", Mol Cell Biol., 20(6): 2108-2121 (2000).
Wallace, "Oncofertility and preservation of reproductive capacity in children and young adults", Cancer, 117(10 Suppl):2301-2310 (2011).
Zhao, et al., "In Vitro Modeling of Human Germ Cell Development Using Pluripotent Stem Cells", Stem Cell Reports, 10(2):509-523 (2018).
Zhou, et al., "Complete Meiosis from Embryonic Stem Cell-Derived Germ Cells In Vitro", Cell Stem Cell, 18(3):330-340 (2016).

\* cited by examiner

Human SHANK3    CCTGCAGAAACGGGACCACGAGGG
Rhesus SHANK3   CCTGCAGAAACGGGACCATGAGGG
                      Target site PAM
gRNA            GCTGCAGAAACGGGACCACGNGG WT Rhesus *SHANK3*  CCTGCAGAAACGGGACCATGAGGGCTTTGGTTTTG
Mutated *SHANK3*   CCTGCAGAAACGGGACCAT..............TTTGGTTTTG

COMPOSITIONS AND METHODS FOR IMPROVING EMBRYO DEVELOPMENT

CROSS-REFERENCE TO RELATED APPLICATIONS

This application is a National Phase application under 35 U.S.C. § 371 of International Application No. PCT/US2019/044589, filed on Aug. 1, 2019, which claims the benefit of and priority to U. S. S. N. 62/713,182, filed Aug. 1, 2018, which are specifically incorporated by reference herein in their entireties.

STATEMENT REGARDING FEDERALLY SPONSORED RESEARCH

This invention was made with government support under Grant No. OD020182 awarded by the National Institutes of Health. The government has certain rights in the invention.

REFERENCE TO THE SEQUENCE LISTING

The Sequence Listing submitted as a text file named "UGA_2018_017_PCT" created on Jul. 31, 2019, and having a size of 24,184 bytes is hereby incorporated by reference pursuant to 37 C.F.R. § 1.52(e)(5).

FIELD OF THE INVENTION

The invention is generally directed to compositions and methods for improving embryo development during, for example, in vitro fertilization.

BACKGROUND OF THE INVENTION

Infertility is now a progressive global health issue affecting more than 50 million couples worldwide. Since the 1970's, there has been a ~50% decrease in sperm parameters in Western men, sparking global concerns about a "sperm crisis" (Levine et al., *Hum Reprod Update* 23, 646-659, doi:10.1093/humupd/dmx022 (2017)). Currently, ~15% of couples worldwide and ~12% of men in the United States are subfertile or infertile (Chandra et al., *Natl Health Stat Report*, 1-18, 11 p following 19 (2013), Gassei & Orwig, *Fertil Steril* 105, 256-266, doi:10.1016/j.fertnstert.2015.12.020 (2016), Louis et al., *Andrology* 1, 741-748, doi:10.1111/j.2047-2927.2013.00110.x (2013)).

Some root causes for this infertility lie in genetic defects, but others are due to exposure to industrial and environmental toxicants, injury, or medical treatments such as alkylating chemotherapies which almost always result in sterility, especially in men (Bahadur, *Mol Cell Endocrinol* 169, 117-122, doi:S0303-7207(00)00364-6 [pii](2000), Deutsch et al., *Am J Transplant* 7, 2414-2421, doi:AJT1929 [pii]10.1111/j.1600-6143.2007.01929.x (2007), Schlegel, *Minerva Ginecol* 61, 261-283 (2009), Skrzypek & Krause, *Andrologia* 39, 198-199, doi:AND787 [pii]10.1111/j.1439-0272.2007.00787.x (2007), Wallace, *Cancer* 117, 2301-2310, doi:10.1002/cncr.26045 (2011)). While advances in fertility preservation during cancer therapies has improved fertile outcomes after treatment cessation, there still exists a large number of male patients that have survived cancer but are permanently sterile. Since 1980, Assisted Reproductive Technologies (ART) such as Intracytoplasmic Sperm Injection (ICSI) have aided couples with severe male factor infertility to achieve pregnancies. However, these techniques rely on the production of male gametes (sperm or spermatids) to fertilize a partner's oocyte in vitro. For those patients unable to provide sperm or spermatid samples, no treatment options are available.

Regardless of the root cause, men who are unable to produce gametes useful in ART are unable to father a child with their partner as no cures currently exist to treat their infertility. Thus, there remains a need for improved treatment options for male factor infertility.

It is an object of the invention to provide compositions and methods for increasing fertilization rates of sperm derived from male subjects with reduced fertility.

It is also an object of the present invention to provide compositions and methods for treating idiopathic male factor infertility.

It is another object of the invention to provide feeder cell-free compositions and methods of making functional male gametes.

SUMMARY OF THE INVENTION

Compositions and methods for improving embryo development are provided. Typically, the methods include administering into a female gamete, male gamete, or fertilized embryo an effective amount of a compound that increases bioavailability of a Ten-eleven translocation (TET) protein family to improve fertilization rate, or development of the fertilized embryo or a subsequent embryo resulting from fertilization of the female gamete by the male gamete. For example, the compound can be administered into an oocyte before, during, or after fertilization. The compound can be administered by, for example, an injection such as intracytoplasmic injection or electroporation. In preferred embodiments, the compound and the male gamete are administered into an oocyte in combination by intracytoplasmic sperm injection (ICSI) of sperm, spermatids, or other male gametes. The compositions and methods can increase the number of fertilized oocytes that develop, for example, to the two-cell, four-cell, eight-cell, sixteen-cell, morula, and/or blastocyte stages following fertilization; increase the rate (e.g., speed) at which an individual embryo develops to the two-cell, four-cell, eight-cell, sixteen-cell, morula, and/or blastocyte stages following fertilization; improve the rate of embryo cleavage; or a combination thereof. In some embodiments, the increase and/or improvement is similar to fertilization and subsequent embryo development using normal spermatozoa.

The compositions and methods can be used to treat idiopathic male factor infertility, allowing infertile/sub-fertile/sterile men to father their own genetic offspring. The disclosed methods typically include injecting or otherwise delivering a compound that increases TET bioavailability into a male gamete preferably, spermatids or haploid spermatogenic cells (or a female gamete, or fertilized embryo). In some embodiments, spermatids or haploid spermatogenic cells are from a male subject who does not produce mature spermatozoa. Immature sperm cells such as haploid round spermatids or elongated spermatids from male with low semen quality have lower levels of TET protein compared to mature spermatozoa resulting in insufficient TET bioactivity to achieve efficient fertilization and subsequent development. Thus the increase of TET bioactivity by co-injecting or otherwise delivering haploid round spermatids or elongated spermatids with a compound that increases TET bioactivity can improve fertilization and embryo development with higher quantity and quality embryos for embryo transfer.

The TET protein can be TET1, TET2, TET3, or a combination thereof. The compound for increasing TET bioavailability can be a small molecule, a TET polypeptide or protein, a fusion protein including a TET polypeptide or protein, an isolated nucleic acid encoding a TET polypeptide or protein or TET fusion protein, an agent such as a transcription factor that increases endogenous expression of a TET polypeptide or protein, or a combination thereof.

In preferred embodiments, the compound increases bioavailability of TET3. Exemplary compounds include TET3 polypeptide or protein, a fusion protein including a TET3 polypeptide or protein, an isolated nucleic acid encoding a TET3 polypeptide or protein or TET3 fusion protein, an agent such as a transcription factor or small molecule that increases endogenous expression of a TET3 polypeptide or protein, or a combination thereof. For example, the TET3 polypeptide or protein can be full-length TET3 or a functional fragment thereof. In particular embodiments, the TET3 polypeptide or protein is human TET3, a functional fragment thereof, or a variant thereof having at least 85% sequence identity to human TET3.

The male gamete can be a round spermatid, elongating spermatid, condensing spermatid, or condensed spermatid derived in vitro or in vivo. In some embodiments, the male gamete is prepared by differentiating an embryonic stem cell, induced pluripotent stem cell, or spermatogonia stem cell into a spermatid. Methods for doing so are also provided.

Methods of modifying the genome of a male gamete or an embryo are also provided. In some embodiments, the method includes administering to the induced pluripotent stem cells, male gamete or embryo, an effective amount of a gene editing composition to correct a gene mutation or anomaly in the genome thereof. A preferred gene editing composition is a CRISPR/Cas system but other gene editing methods are not excluded. In some embodiments, the gene editing compositions also includes a donor polynucleotide with sufficient homology to the genomic sequence at the target site to modify the genome at or adjacent to the target site by homology-directed repair. The donor polynucleotide can introduce one or more insertions, deletions, or substitutions in the genome. In some embodiments, the insertions, deletions, or substitutions correct a mutation, such as a mutation associated with genetic disease or condition.

Thus, the compositions and methods disclosed herein include, but are not limited to, composition and methods for increasing the bioavailability/co-injecting TET proteins to, for example, improve ICSI/embryo development rates when injecting immature sperm/spermatids; methods of using patient specific pluripotent stem cells to generate functional gametes in vitro and to treat, e.g., male factor infertility; feeder-free differentiation methods and protocols for generating functional gametes from patient specific stem cells including spermatogonia; and using gene editing tools to correct mutations disease-causing mutations in, for example fibroblasts or iPSCs, prior to differentiation into functional gametes.

BRIEF DESCRIPTION OF THE DRAWINGS

FIG. 6A shows a population distribution showing wild-type (25%) and mutant (75%) genotypes. FIG. 6B shows a distribution of the timing of mutation during early embryonic division. n=96.

DETAILED DESCRIPTION OF THE INVENTION

I. Definitions

Figure 1A:
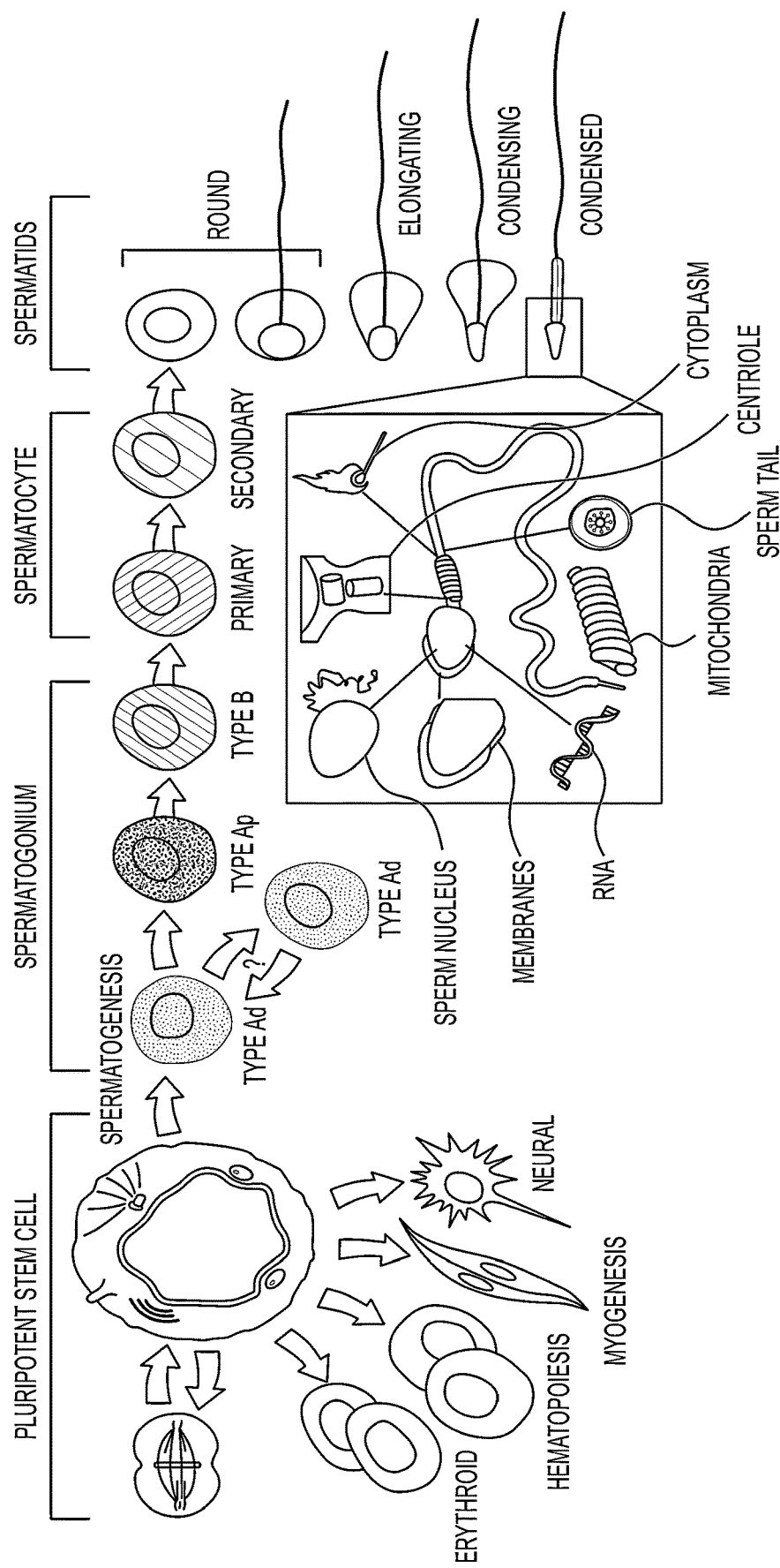
FIG. 1A is a schematic representing various stages of spermatogenesis that can be generated in vitro up to the elongating spermatid stage.
Figure 1B:
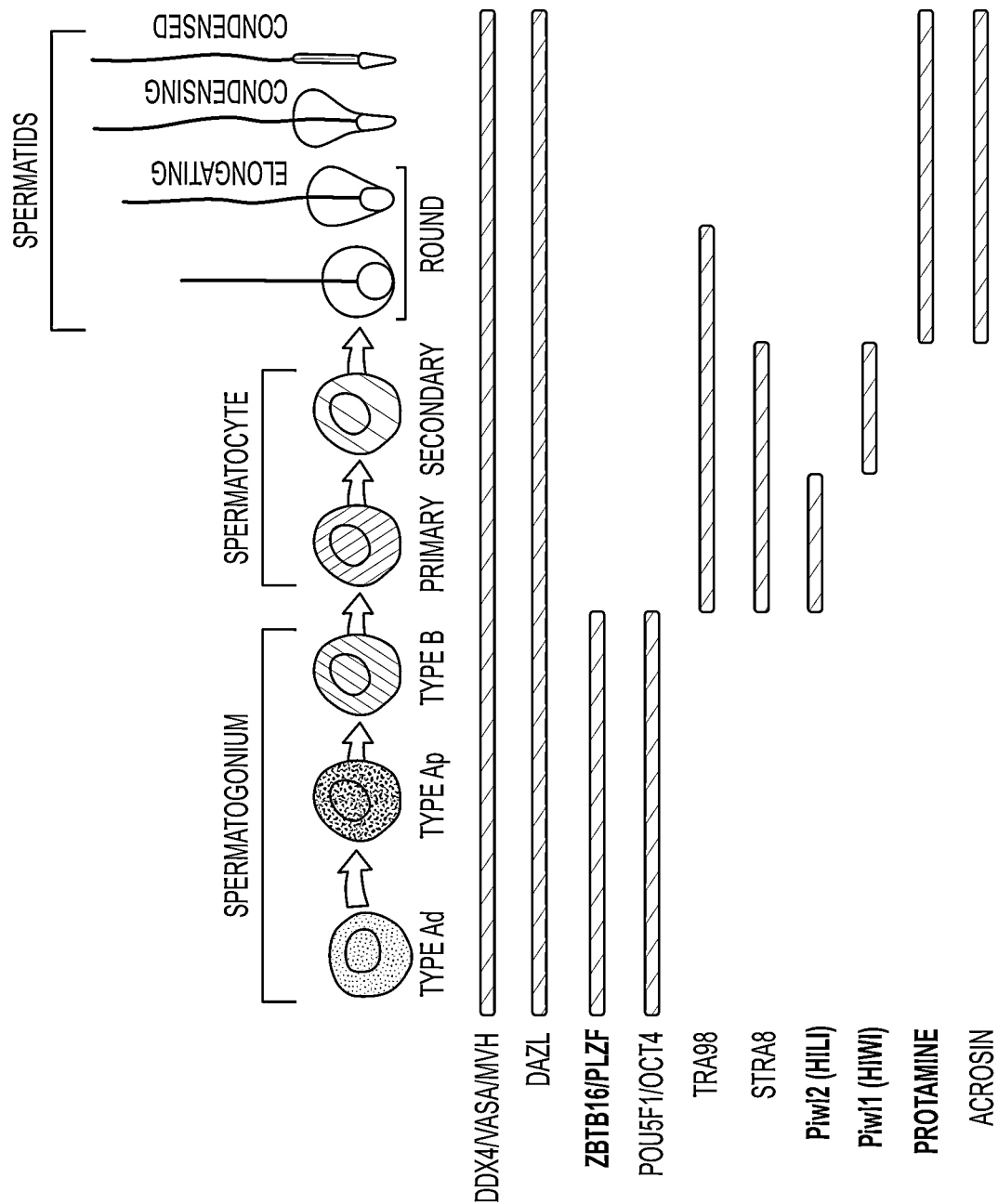
FIG. 1B is an illustration showing differentiating sperm cell markers: DDX4/VASA/: DEAD-Box Helicase 4; DAZL:Deleted in AZoospermia like; ZBTB16/PLZF: promyelocytic leukemia zinc finger; TRA98: Germ cell specific marker; STRA8: Stimulated BY Retinoic Acid 8; Piwil2: piwi like protein 2; Piwil1: Piwi-like protein 1; Protamine and Acrosine, and expression thereof during spermatogenesis.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, the term "identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, "treat" means to prevent, reduce, decrease, or ameliorate one or more symptoms, characteristics or comorbidities of an age-related disease, disorder or condition; to reverse the progression of one or more symptoms, characteristics or comorbidities of an age related disorder; to halt the progression of one or more symptoms, characteristics or comorbidities of an age-related disorder; to prevent the occurrence of one or more symptoms, characteristics or comorbidities of an age-related disorder; to inhibit the rate of development of one or more symptoms, characteristics or comorbidities or combinations thereof.

As used herein, the term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

As used herein, the term "vector" refers to a replicon, such as a plasmid, phage, or cosmid, into which another DNA segment may be inserted so as to bring about the replication of the inserted segment. The vectors can be expression vectors.

As used herein, the term "expression vector" refers to a vector that includes one or more expression control sequences.

As used herein, the term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein, the terms "transformed," "transgenic," "transfected" and "recombinant" refer to a host organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

II. Compositions and Methods of Increasing TET Bioavailability

Compositions and methods for treating male factor infertility, improving fertilization rates, and enhancing embryo development are provided. The disclosed compositions and methods can be used to enable infertile/sub-fertile/sterile men to father their own genetic offspring. The compositions and methods are particularly advantageous for male subjects including, but not limited to, those who do not produce mature spermatozoa. Additionally provided are strategies for using genome editing tools such as CRISPR technology to correct inherited mutations and perform thorough genetic assessments in subject-specific induced pluripotent stem cells prior to differentiation into spermatids, thus providing for production and selection of genetically corrected embryos. Any of the disclosed methods can be used alone or in any combination.

There are three TET family proteins, TET1, TET2, and TET3. TET proteins are large (~180- to 230-kDa) multidomain enzymes, each containing a conserved double-stranded β-helix (DSBH) domain, a cysteine-rich domain, and binding sites for the cofactors Fe(II) and 2-oxoglutarate (2-OG) that together form the core catalytic region in the C terminus (Rasmussen and Helin, *Genes Dev.*, 30(7): 733-750 (2016)). Structural studies indicate that the core catalytic region preferentially binds cytosines in a CpG context but does not interact with surrounding DNA bases and shows little or no specificity for flanking DNA sequences. In addition to their catalytic domain, TET1 and TET3 have an N-terminal CXXC (SEQ ID NO:11) zinc finger domain that can bind DNA (Long, et al., *Biochem Soc Trans.* 41(Pt 3): 727-740 (2013), Voo, et al., *Mol Cell Biol.*, 20(6): 2108-2121 (2000)).

TET proteins catalyze the successive oxidation of 5-methylcytosine (5mC) to 5-hydroxymethylcytosine (5hmC), 5-formylcytosine (5fC), and 5-carboxylcytosine (5caC). These 5mC oxidation products intermediates in the conversion of 5mC to unmodified cytosines, thus providing the first steps in a pathway for active DNA demethylation and indicating that DNA methylation patterns are not as static as initially assumed.

The erasure of methylated marks in zygotes shortly after fertilization, specifically in the male genome of in vitro derived spermatids, might have profound impact on zygotic genome activation (ZGA) and subsequent activation of the embryonic genome. Unlike rodent, rhesus macaque embryonic genome activation (EGA) occurred at the 8-cell stage instead of 2-cell stage in rodents (Chitwoord et al., *Biol Reprod*, 97:353-364, 2017). In mice, shortly after fertilization there is a global loss of 5mC in paternal genome with rapid conversion to 5hmC and its downstream oxidation products including 5fC and 5caC which were further catalyzed by the maternally stored Tet3 proteins (Shen et al., *Cell Stem Cell.* 2; 15(4):459-71 (2014)). In human, TET1-3 proteins are successively expressed during spermatogenesis. With TET2 expressed in the cytoplasm of late pachytene spermatocytes of Stage V, TET1 expressed in the nuclei of Step I round spermatids at Stage 1 and Tet3 started to express in nuclei of Step 3 spermatids at Stage III while 5hmC appears in Step 5 elongated spermatids (Ni et al., *Hum Reprod.*, 31(7); 1411-24, (2016)). The expression levels of TET enzymes are positively correlated with progressive sperm motility which is important for male fertility.

A report on de novo DNA methylation during rhesus pre-implantation development indicated that TET3 is expressed during the major wave of active demethylation in early embryos shortly after fertilization while TET1/2 started to express from 8-cell stage onward when EGA initiated (Gao et al., *Cell Res*, 27:526-539 (2017)).

A. Methods of Increasing TET Bioavailability

The results presented below are consistent with the conclusion that TET3 erases methylated marks shortly in spermatids, and demonstrate the importance of timing of TET3 activity or paternal demethylation during ZGA and subsequent EGA events. Compared to injecting sperm extract alone, co-injection of TET3-pDNA improved cleavage rate while co-injection with Tet3-mRNA further improve development up to 8 cell stage with development to 16 cell stage and morula at low rate. Co-injection with TET3 protein significantly improved cleavage rate with majority of embryo develop beyond 8-cell stage and with close to 12% reached to blastocyst stage. In addition, TET3 improved the morphology and development rate of preimplantation embryos, while reducing fragmentation.

Compositions and method for improving preimplantation embryos are provided. Typically, the methods typically include increasing the bioavailability of a ten eleven translocation (TET) family protein in a preimplantation embryo.

The compositions and methods can increase the number of fertilized oocytes that develop, for example, to the two-cell, four-cell, eight-cell, sixteen-cell, morula, and/or blastocyte stages following fertilization; increase the rate at which an individual embryo develops to the two-cell, four-cell, eight-cell, sixteen-cell, morula, and/or blastocyte stages following fertilization; or a combination thereof. Embryo morphology and reduced fragmentation can be used to measure improved viability. For example, in some embodiments, the rate of embryo cleavage is improved. Also, the development rate or advancement to each subsequent stage can also be used to measure improvement. For example, TET injected embryos show similar development time such as reaching blastocyst stage by Day 7 after fertilization, which is similar to those fertilized using normal spermatozoa.

The TET protein can be increased by, for example, injecting or otherwise delivering a compound that increases the bioavailability of a TET protein into a male gamete, e.g., a haploid spermatocytes, spermatid or spermatozoa; an oocyte; or fertilized embryo, particularly an early stage embryo e.g., a two-cell, four-cell, eight-cell, sixteen-cell, morula, and/or blastocyte stage embryo.

Preferred compounds are discussed in more detail below and include, but are not limited to TET protein; a nucleic acid encoding a TET protein, including but not limited to TET mRNA, or an expression vector encoding TET; or a combination thereof. Chemicals or small molecules that enhance TET expression, for example TET3, in haploid spermatids during in vitro differentiation can be used.

In preferred embodiments, the TET is TET3. A preferred method of increasing the presence of a TET protein such as TET3 includes co-injection a compound that increases bioavailability of a TET along with immature spermatids into oocytes at the time of intercytoplasmic sperm injection (ICSI) to improve preimplantation embryo development and blastocyst rates.

In some embodiments, the methods also include injection of sperm extract. The sperm extract can be prepared from ejaculated sperm as follows. Ejaculated sperm is washed with TH3 medium by centrifugation at 1500 rpm for 5 min. The supernatant is aspirated out the supernatant and the sperm concentration adjusted to $5-10 \times 10^{\wedge}8$ sperm/mL-.Sperm layer is then be pelleted and washed three times with modified intracellular buffer (ICB) by centrifugation at 1,400 rpm (Eppendorf benchtop centrifuge) for 5 min at RT. This is followed by Lysing by four freeze-thaw cycles. The lysed samples are then be spin at 100,000×g (e.g. 48,000 rpm of Beckman micro-ultracentrifuge) for 1 hour at 4 C. The supernatant is transferred to new clean Eppendorf tube, and kept on ice. It is then concentrated (~3-5 folds) by using centrocon-30 microfiltration membrane (Amicon Cat #4208) and centrifugation at 3000×g for 20 min Aliquoted 10 uL per vial and stored at −80° C.

TABLE 2

ICB buffer (pH 7.5)

| | Vender/Cat# | Final Conc. | | g/50 mL | g/100 mL |
|---|---|---|---|---|---|
| KCL | Sigma P5405 | 120 | mM | 0.44735 | 0.8947 |
| HEPES | Sigma H6147 | 20 | mM | 0.2833 | 0.5666 |
| EGTA | Sigma E3889 | 100 | μM | 0.0019 | 0.0038 |
| Sodium glycerophosphate | Sigma G-5422 FW = 216.04 <0.1% alpha-L-isomer | 10 | mM | 0.108 | 0.2160 |

In some embodiments, preimplantation embryos, particularly blastocysts, treated with a TET such as TET3 have improved morphology, an improved likelihood of development, reduced rate of fragmentation, or a combination thereof.

The compositions can also include trichostatin A (TSA), and methods can include administering TSA. TSA is an organic compound that selectively inhibits the class I and II mammalian histone deacetylase (HDAC) families of enzymes, but not class III HDACs (i.e., sirtuins). TSA can alter gene expression by interfering with the removal of acetyl groups from histones (histone deacetylases, HDAC), altering the ability of DNA transcription factors to access the DNA molecules inside chromatin.

B. Compounds for Increasing TET Bioavailability

Compounds for increasing the bioactivity of TET protein, and formulations formed therewith are provided. In some embodiments, the compound is a small molecule, a TET polypeptide or protein, a fusion protein including a TET polypeptide or protein, an isolated nucleic acid encoding a TET polypeptide or protein or TET fusion protein, or an agent such as a transcription factor that increases endogenous expression of a TET polypeptide or protein. The compound can increase the expression or bioavailability of a TET.

In some embodiments, the compound has at 70%, at least 75%, at least 80%, at least 85%, at least 90%, at least 95%, at least 98%, at least 99%, or more, sequence identity to TET1, TET2, or TET3, in particular human TET1, TET2, or TET3.

For example, in some embodiments, the compound is a human wildtype TET protein such as SEQ ID NOS:1, 9, or 10, or a functional fragment thereof, or a variant thereof with at least 50, 60, 70, 80, 85, 90, 95, 96, 97, 98, or 99% sequence identity to SEQ ID NOS:1, 9, or 10, including but not limited to human TET3 isoform 2, 3, or 4. In some embodiments, the compound is a TET protein such as SEQ ID NOS:13, or a functional fragment thereof, or a variant thereof with at least 50, 60, 70, 80, 85, 90, 95, 96, 97, 98, or 99% sequence identity to SEQ ID NOS:13.

In some embodiments, the compound is a nucleic acid encoding a human wildtype TET3 protein such as SEQ ID NO:2, or a functional fragment thereof, or a variant thereof with at least 50, 60, 70, 80, 85, 90, 95, 96, 97, 98, or 99% sequence identity to SEQ ID NO:2. In some embodiments, the compound includes a nucleic acid sequence such as SEQ ID NOS:12, or a functional fragment thereof, or a variant thereof with at least 50, 60, 70, 80, 85, 90, 95, 96, 97, 98, or 99% sequence identity to SEQ ID NOS:12.

In some embodiments, the compound is a fragment of a fully length TET protein. Such fragments usually encode proteins of at least 5 amino acids in length. In some embodiments, they may encode proteins of 6 to 10, 11 to 15, 16 to 25, 26 to 50, 51 to 75, 76 to 100 or 101 to 250 or 250 to 500, 500 to 1000, 1000 to 1500 or 1500 to 2000 amino acids. Fragments may include sequences with one or more amino acids removed, for example, C-terminus truncated protein, N-terminus truncated proteins, or a combination thereof. Fragments may also include nucleic acids that encode proteins with or without a particular domain, for example fragments where the CXXC (SEQ ID NO:11) (DNA-binding) domain, or catalytic domain is absent.

In some embodiments, the compound is one that increases bioactivity of an endogenous TET, e.g., endogenous TET3. Such compounds include factors that increase the expression, or increase the half-life, of an endogenous TET. Factors that increase expression of endogenous TET proteins include, for example, TET transcription factors. TET transcription factors can be provided as a recombinant polypeptide, or an isolated nucleic acid encoding the transcription factor.

1. TET Sequences

Protein and nucleic acid sequences for TET proteins are known in the art, and include, for example, Table 1, which provide Uniprot Database Accession numbers for human and rhesus macaque TET1, TET2, and TET3 proteins, the contents of each of which are specifically incorporated by reference in their entireties.

TABLE 1

Exemplary TET Accession Numbers

| Entry | Entry name | Protein names | Gene names | Organism | Length |
|---|---|---|---|---|---|
| Q8NFU7 | TET1_HUMAN | Methylcytosine dioxygenase TET1 | TET1 CXXC6, KIAA1676, LCX | Homo sapiens (Human) | 2,136 |
| F7EF05 | F7EF05_MACMU | Tet methylcytosine dioxygenase 1 | TET1 | Macaca mulatta (Rhesus macaque) | 2,043 |
| Q6N021 | TET2_HUMAN | Methylcytosine dioxygenase TET2 | TET2 KIAA1546, Nbla00191 | Homo sapiens (Human) | 2,002 |
| F7DR39 | F7DR39_MACMU | Tet methylcytosine dioxygenase 2 | TET2 | Macaca mulatta (Rhesus macaque) | 2,020 |
| O43151 | TET3_HUMAN | Methylcytosine dioxygenase TET3 | TET3 KIAA0401 | Homo sapiens (Human) | 1,660 |
| F7D294 | F7D294_MACMU | Tet methylcytosine dioxygenase 3 | TET3 | Macaca mulatta (Rhesus macaque) | 1,795 |
| H9FJH1 | H9FJH1_MACMU | Methylcytosine dioxygenase TET3 | TET3 | Macaca mulatta (Rhesus macaque) | 348 |

Sequences, fragments, and derivatives of TET family proteins are also described in U.S. Published Application Nos. 2011/0236894 and 2016/0186207.

In particularly preferred embodiments, the compound that increases TET bioavailability is a TET1, TET2, or TET3 polypeptide or protein, a fusion protein including a TET1, TET2, or TET3 polypeptide or protein, an isolated nucleic acid encoding a TET1, TET2, or TET3 polypeptide or protein or TET1, TET2, or TET3 fusion protein, or any combination thereof. The isolated nucleic acid can be, for example, TET1, TET2, or TET3 mRNA or an expression vector encoding TET1, TET2, or TET3. Variant polypeptides having at least 50%, 60%, 70%, 75%, 80%, 85%, 90%, 95%, or more sequence identity to the TET sequences provided herein by sequence or accession number are also provided.

An exemplary human TET3 amino acid sequence (i.e., 'canonical' isoform 1) is

MDSGPVYHGDSRQLSASGVPVNGAREPAGPSLLGTGGPWRVDQKPDWEAA

PGPAHTARLEDAHDLVAFSAVAEAVSSYGALSTRLYETFNREMSREAGNN

SRGPRPGPEGCSAGSEDLDTLQTALALARHGMKPPNCNCDGPECPDYLEW

LEGKIKSVVMEGGEERPRLPGPLPPGEAGLPAPSTRPLLSSEVPQISPQE

GLPLSQSALSIAKEKNISLQTAIAIEALTQLSSALPQPSHSTPQASCPLP

EALSPPAPFRSPQSYLRAPSWPVVPPEEHSSFAPDSSAFPPATPRTEFPE

AWGTDTPPATPRSSWPMPRPSPDPMAELEQLLGSASDYIQSVFKRPEALP

TKPKVKVEAPSSSPAPAPSPVLQREAPTPSSEPDTHQKAQTALQQHLKHK

RSLFLEQVHDTSFPAPSEPSAPGWWPPPSSPVPRLPDRPPKEKKKKLPTP

AGGPVGTEKAAPGIKPSVRKPIQIKKSRPREAQPLFPPVRQIVLEGLRSP

ASQEVQAHPPAPLPASQGSAVPLPPEPSLALFAPSPSRDSLLPPTQEMRS

PSPMTALQPGSTGPLPPADDKLEELIRQFEAEFGDSFGLPGPPSVPIQDP

ENQQTCLPAPESPFATRSPKQIKIESSGAVTVLSTTCFHSEEGGQEATPT

KAENPLTPTLSGFLESPLKYLDTPTKSLLDTPAKRAQAEFPTCDCVEQIV

EKDEGPYYTHLGSGPTVASIRELMEERYGEKGKAIRIEKVIYTGKEGKSS

RGCPIAKWVIRRHTLEEKLLCLVRHRAGHHCQNAVIVILILAWEGIPRSL

GDTLYQELTDTLRKYGNPTSRRCGLNDDRTCACQGKDPNTCGASFSFGCS

WSMYFNGCKYARSKTPRKFRLAGDNPKEEEVLRKSFQDLATEVAPLYKRL

APQAYQNQVTNEEIAIDCRLGLKEGRPFAGVTACMDFCAHAHKDQHMLYN

GCTVVCTLTKEDNRCVGKIPEDEQLHVLPLYKMANTDEFGSEENQNAKVG

SGAIQVLTAFPREVRRLPEPAKSCRQRQLEARKAAAEKKKIQKEKLSTPE

KIKQEALELAGITSDPGLSLKGGLSQQGLKPSLKVEPQNHFSSFKYSGNA

VVESYSVLGNCRPSDPYSMNSVYSHSYYAQPSLTSVNGFHSKYALPSFS

YYGFPSSMPVFPSQFLGPGAWGHSGSSGSFEKKPDLHALHNSLSPAYGGA

EFAELPSQAVPTDAHHPTPHHQQPAYPGPKEYLLPKAPLLHSVSRDPSPF

AQSSNCYNRSIKQEPVDPLTQAEPVPRDAGKMGKTPLSEVSQNGGPSHLW

GQYSGGPSMSPKRTNGVGGSWGVFSSGESPAIVPDKLSSFGASCLAPSHF

TDGQWGLFPGEGQQAASHSGGRLRGKPWSPCKFGNSTSALAGPSLTEKPW

ALGAGDFNSALKGSPGFQDKLWNPMKGEEGRIPAAGASQLDRAWQSFGLP

LGSSEKLFGALKSEEKLWDPFSLEEGPAEEPPSKGAVKEEKGGGGAEEEE

EELWSDSEHNFLDENIGGVAVAPAHGSILIECARRELHATTPLKKPNRCH

PTRISLVFYQHKNLNQPNHGLALWEAKMKQLAERARARQEEAARLGLGQQ

EAKLYGKKRKWGGTVVAEPQQKEKKGVVPTRQALAVPTDSAVTVSSYAYT

KVTGPYSRWI (SEQ ID NO: 1, UniProtKB-O43151 (TET3_HUMAN), which is specifically incorporated by reference herein in its entirety).

TET 3 Isoform 2 (identifier: O43151-21 differs from the canonical sequence as follows: 1440-1555: Missing.

TET3 Isoform 3 (identifier: O4315-1-3) differs from the canonical sequence as follows: 728-1660: Missing.

TET3 Isoform 4 (identifier: O43151-41 differs from the canonical sequence as follows: 1-1: M→

(SEQ ID NO: 3)
MSQFQVPLAVQPDLPGLYDFPQRQVMVGSFPGSGLSMAGSESQLRG

GGDGRKKRKRCGTCEPCRRLENCGACTSCTNRRTHQICKLRKCEVL

KKKVGLLKEVEIKAGEGAGPWGQGAAVKTGSELSPVDGPVPGQM.

A nucleic acid sequence encoding human TET3 is atgagccagtttcaggtgccctggccgtccagccggacctgccaggcct
ttatgacttccctcagcgccaggtgatggtagggagcttcccggggtctg
ggctctccatggctgggagtgagtcccaactccgaggggtggagatggt
cgaaagaaacggaaacggtgtggtacttgtgagccctgccggcggctgga
aaactgtggcgcttgcactagctgtaccaaccgccgcacgcaccagatct
gcaaactgcgaaaatgtgaggtgctgaagaaaaaagtagggcttctcaag
gaggtggaaataaaggctggtgaaggagccgggccgtggggacaaggagc
ggctgtcaagacaggctcagagctcagcccagttgatggacctgttccag
gtcagatggactcagggccagtgtaccatggggactcacggcagctaagc
gcctcagggtgccggtcaatggtgctagagagcccgctggacccagtct
gctggggactgggggtccttggcgggtagaccaaaagcccgactgggagg
ctgccccaggcccagctcatactgctcgcctggaagatgcccacgatctg
gtggccttttcggctgtggccgaagctgtgtcctcttatgggcccttag
cacccggctctatgaaaccttcaaccgtgagatgagtcgtgaggctggga
acaacagcagggaccccggccagggcctgagggctgctctgctggcagc
gaagaccttgacacactgcagacggccctggccctcgcgcggcatggtat
gaaaccaccaactgcaactgcgatgcccagaatgcctgactacctcg
agtggctggaggggaagatcaagtctgtggtcatggaaggaggggaggag
cggcccaggctcccaggcctctgcctcctggtgaggccggcctccagc
accaagcaccaggccactcctcagctcagaggtgccccagatctctcccc
aagagggcctgcccctgtcccagagtgccctgagcattgccaaggaaaaa
aacatcagcttgcagaccgccattgccattgaggccctcacacagctctc
ctctgccctcccgcagccttctcattccaccccccaggcttcttgccccc
ttcctgaggccttgtcacctcctgccccttcagatctccccagtcttac ctccgggctccctcatggcctgtggttcctcctgaagagcactcatcttt
tgctcctgatagctctgccttccctccagcaactcctagaactgagttcc
ctgaagcctggggcactgacacccctccagcaacgccccggagctcctgg
cccatgcctcgcccaagccccgatcccatggctgaactggagcagttgtt
gggcagcgccagtgattacatccagtcagtattcaagcggcctgaggccc
tgcctaccaagcccaaggtcaaggtggaggcaccctcttcctcccggcc
ccggccccatcccctgtacttcagagggaggctcccacgccatcctcgga
gcccgacacccaccagaaggcccagaccgccctgcagcagcacctccacc
acaagcgcagcctcttcctagaacaggtgcacgacacctccttccctgct
ccttcagagccttctgctcctggctggtggccccaccaagttcacctgt
cccacggcttccagacagaccacccaaggagaagaagaagaagctcccaa
caccagctggaggtcccgtgggaacggagaaagctgcccctgggatcaag
cccagtgtccgaaagcccattcagatcaagaagtccaggccccgggaagc
acagcccctcttcccacctgtccgacagattgtcctggaagggcttaggt
ccccagcctcccaggaagtgcaggctcatccaccggcccctctgcctgcc
tcacagggctctgctgtgcccctgccccagaaccttctcttgcgctatt
tgcacctagtccctccagggacagcctgctgcccctactcaggaaatga
ggtcccccagccccatgacagccttgcagccaggctccactggccctctt
ccccctgccgatgacaagctggaagagctcatccggcagtttgaggctga
atttggagatagctttgggcttcccggcccccttctgtgccattcagg
accccgagaaccagcaaacatgtctcccagccctgagagcccctttgct
acccgttcccccaagcaaatcaagattgagtcttcggggggctgtgactgt
gctctcaaccacctgcttccattcagaggagggaggacaggaggccacac
ccaccaaggctgagaacccactcacacccaccctcagtggcttcttggag
tcacctcttaagtacctggacacacccaccaagagtctgctggacacacc
tgccaagagagccaggccgagttccccaacctgcgattgcgtcgaacaaa
tagtggagaaagatgaaggtccatattatactcacttgggatctggcccc
acggtcgcctctatccgggaactcatggaggagcggtatggagagaaggg
gaaagccatccggatcgagaaggtcatctacacgggggaaggagggaaaga
gctcccgcggttgccccattgcaaagtaggtgatccgcaggcacacgctg
gaggagaagctactctgcctggtgcggcaccgggcaggccaccactgcca
gaacgctgtgatcgtcatcctcatcctggcctgggagggcattcccgta
gcctcggagacaccctctaccaggagctcaccgacaccctccggaagtat
gggaaccccaccagccggagatgcggcctcaacgatgaccggacctgcgc
ttgccaaggcaaagaccccaacacctgtggtgcctccttctcctttggtt
gttcctggagcatgtacttcaacggctgcaagtatgctcggagcaagaca
cctcgcaagttccgcctcgcagggacaatcccaaagaggaagaagtgct
ccggaagagtttccaggacctggccaccgaagtcgctcccctgtacaagc
gactggcccctcaggcctatcagaaccaggtgaccaacgaggaaatagcg
attgactgccgtctggggctgaaggaaggacggccttcgcgggggtcac -continued

```
ggcctgcatggacttctgtgcccacgccacaaggaccagcataacctct
acaatgggtgcaccgtggtctgcaccctgaccaaggaagacaatcgctgc
gtgggcaagattcccgaggatgagcagctgcatgttctcccctgtacaa
gatggccaacacggatgagtttggtagcgaggagaaccagaatgcaaagg
tgggcagcggagccatccaggtgctcaccgccttcccccgcgaggtccga
cgcctgcccgagcctgccaagtcctgccgccagcggcagctggaagccag
aaaggcagcagccgagaagaagaagattcagaaggagaagctgagcactc
cggagaagatcaagcaggaggccctggagctggcgggcattacgtcggac
ccaggcctgtctctgaagggtggattgtcccagcaaggcctgaagccctc
cctcaaggtggagccgcagaaccacttcagctccttcaagtacagcggca
acgcggtggtggagagctactcggtgctgggcaactgccggcctccgac
ccttacagcatgaacagcgtgtactcctaccactcctactatgcacagcc
cagcctgacctccgtcaatggcttccactccaagtacgctctcccgtctt
ttagctactatggctttccatccagcaacccgtcttcccctctcagttc
ctgggtcctggtgcctgggggcacagtggcagcagtggcagttttgagaa
gaagccagacctccacgctctgcacaacagcctgagcccggcctacggtg
gtgctgagtttgccgagctgcccagccaggctgttcccacagacgccac
cacccccactcctcaccaccagcagcctgcgtacccaggccccaaggagta
tctgcttcccaaggccccctactccactcagtgtccagggaccccctccc
cctttgcccagagctccaactgctacaacagatccatcaagcaagagcca
gtagacccgctgacccaggctgagcctgtgcccagagacgctggcaagat
gggcaagacacctctgtccgaggtgtctcagaatggaggacccagtcacc
tttggggacagtactcaggaggcccaagcatgtcccccaagaggactaac
ggtgtgggtggcagctggggtgtgttctcgtctggggagagtcctgccat
cgtccctgacaagctcagttcctttggggccagctgcctggcccctccc
acttcacagatggccagtggggctgttcccggtgaggggcagcaggca
gcttcccactctggaggacggctgcgaggcaaacgtggagcccctgcaa
gtttgggaacagcacctcggccttggctgggccagcctgactgagaagc
cgtgggcgctggggcaggggatttcaactcggccctgaaaggtagtcct
gggttccaagacaagctgtggaaccccatgaaggagaggagggcaggat
tccagccgcaggggccagccagctggacagggcctggcagtcctttggtc
tgcccctgggatccagcgagaagctgtttggggctctgaagtcagaggag
aagctgtgggacccttcagcctggaggaggggccggctgaggagccccc
cagcaagggagcggtgaaggaggagaagggcggtggtggtgcggaggagg
aagaggaggagctgtggtcggacagtgaacacaacttcctggacgagaac
atcggcggcgtggccgtggccccagcccacggctccatcctcatcgagtg
tgcccggcgggagctgcacgccaccacgccgcttaagaagcccaaccgct
gccaccccaccgcatctcgctggtcttctaccagcacaagaacctcaac
cagcccaaccacgggctggccctctgggaagccaagatgaagcagctggc
ggagagggcacgggcacggcaggaggaggctgcccggctgggcctgggcc
agcaggaggccaagctctacgggaagaagcgcaagtgggggggcactgtg
```

-continued

```
gttgctgagccccagcagaaagagaagaagggggtcgtcccaccggca
ggcactggctgtgcccacagactcggcggtcaccgtgtcctcctatgcct
acacgaaggtcactggccctacagccgctggatctag (SEQ ID
NO: 2, GenBank: HQ220209.1, Homo sapiens putative
methylcytosine dioxygenase (TET3) mRNA, complete
cds, which is specifically incorporated by
reference herein in its entirety).
```

An exemplary human TET2 amino acid sequence:

```
MEQDRTNHVE GNRLSPFLIP SPPICQTEPL
ATKLQNGSPL PERAHPEVNG
DTKWHSFKSY YGIPCMKGSQ NSRVSPDFTQ
ESRGYSKCLQ NGGIKRTVSE
PSLSGLLQIK KLKQDQKANG ERRNFGVSQE
RNPGESSQPN VSDLSDKKES
VSSVAQENAV KDFTSFSTHN CSGPENPELQ
ILNEQEGKSA NYHDKNIVLL
KNKAVLMPNG ATVSASSVEH THGELLEKTL
SQYYPDCVSI AVQKTTSHIN
AINSQATNEL SCEITHPSHT SGQINSAQTS
NSELPPKPAA VVSEACDADD
ADNASKLAAM LNTCSFQKPE QLQQQKSVFE
ICPSPAENNI QGTTKLASGE
EFCSGSSSNL QAPGGSSERY LKQNEMNGAY
FKQSSVFTKD SFSATTTPPP
PSQLLLSPPP PLPQVPQLPS EGKSTLNGGV
LEEHHHYPNQ SNTTLLREVK
IEGKPEAPPS QSPNPSTHVC SPSPMLSERP
QNNCVNRNDI QTAGTMTVPL
CSEKTRPMSE HLKHNPPIFG SSGELQDNCQ
QLMRNKEQEI LKGRDKEQTR
DLVPPTQHYL KPGWIELKAP RFHQAESHLK
RNEASLPSIL QYQPNLSNQM
TSKQYTGNSN MPGGLPRQAY TQKTTQLEHK
SQMYQVEMNQ GQSQGTVDQH
LQFQKPSHQV HFSKTDHLPK AHVQSLCGTR
FHFQQRADSQ TEKLMSPVLK
QHLNQQASET EPFSNSHLLQ HKPHKQAAQT
QPSQSSHLPQ NQQQQQKLQI
KNKEEILQTF PHPQSNNDQQ REGSFFGQTK
VEECFHGENQ YSKSSEFETH
```

NVQMGLEEVQ NINRRNSPYS QTMKSSACKI

QVSCSNNTHL VSENKEQTTH

PELFAGNKTQ NLHHMQYFPN NVIPKQDLLH

RCFQEQEQKS QQASVLQGYK

NRNQDMSGQQ AAQLAQQRYL IHNHANVFPV

PDQGGSHTQT PPQKDTQKHA

ALRWHLLQKQ EQQQTQQPQT ESCHSQMHRP

IKVEPGCKPH ACMHTAPPEN

KTWKKVTKQE NPPASCDNVQ QKSIIETMEQ

HLKQFHAKSL FDHKALTLKS

QKQVKVEMSG PVTVLTRQTT AAELDSHTPA

LEQQTTSSEK TPTKRTAASV

LNNFIESPSK LLDTPIKNLL DTPVKTQYDF

PSCRCVEQII EKDEGPFYTH

LGAGPNVAAI REIMEERFGQ KGKAIRIERV

IYTGKEGKSS QGCPIAKWVV

RRSSSEEKLL CLVRERAGHT CEAAVIVILI

LVWEGIPLSL ADKLYSELTE

TLRKYGTLTN RRCALNEERT CACQGLDPET

CGASFSFGCS WSMYYNGCKF

ARSKIPRKFK LLGDDPKEEE KLESHLQNLS

TLMAPTYKKL APDAYNNQIE

YEHRAPECRL GLKEGRPFSG VTACLDFCAH

AHRDLHNMQN GSTLVCTLTR

EDNREFGGKP EDEQLHVLPL YKVSDVDEFG

SVEAQEEKKR SGAIQVLSSF

RRKVRMLAEP VKTCRQRKLE AKKAAAEKLS

SLENSSNKNE KEKSAPSRTK

QTENASQAKQ LAELLRLSGP VMQQSQQPQP

LQKQPPQPQQ QQRPQQQQPH

HPQTESVNSY SASGSTNPYM RRPNPVSPYP

NSSHTSDIYG STSPMNFYST

SSQAAGSYLN SSNPMNPYPG LLNQNTQYPS

YQCNGNLSVD NCSPYLGSYS

PQSQPMDLYR YPSQDPLSKL SLPPIHTLYQ

PRFGNSQSFT SKYLGYGNQN

MQGDGFSSCT IRPNVHHVGK LPPYPTHEMD

GHFMGATSRL PPNLSNPNMD

YKNGEHHSPS HIIHNYSAAP GMFNSSLHAL

HLQNKENDML SHTANGLSKM

LPALNHDRTA CVQGGLHKLS DANGQEKQPL

ALVQGVASGA EDNDEVWSDS

EQSFLDPDIG GVAVAPTHGS ILIECAKREL

HATTPLKNPN RNHPTRISLV

FYQHKSMNEP KHGLALWEAK MAEKAREKEE

ECEKYGPDYV PQKSHGKKVK

REPAEPHETS EPTYLRFIKS LAERTMSVTT

DSTVTTSPYA FTRVTGPYNR YI (SEQ ID NO: 9, UniProtKB-Q6N021 (TET2_HUMAN), which is specifically incorporated by reference herein in its entirety).

An exemplary human TET1 amino acid sequence:

MSRSRHARPS RLVRKEDVNK KKKNSQLRKT

TKGANKNVAS VKTLSPGKLK

QLIQERDVKK KTEPKPPVPV RSLLTRAGAA

RMNLDRTEVL FQNPESLTCN

GFTMALRSTS LSRRLSQPPL VVAKSKKVPL

SKGLEKQHDC DYKILPALGV

KHSENDSVPM QDTQVLPDIE TLIGVQNPSL

LKGKSQETTQ FWSQRVEDSK

INIPTHSGPA AEILPGPLEG TRCGEGLFSE

ETLNDTSGSP KMFAQDTVCA

PFPQRATPKV TSQGNPSIQL EELGSRVESL

KLSDSYLDPI KSEHDCYPTS

SLNKVIPDLN LRNCLALGGS TSPTSVIKFL

LAGSKQATLG AKPDHQEAFE

ATANQQEVSD TTSFLGQAFG AIPHQWELPG

ADPVHGEALG ETPDLPEIPG

AIPVQGEVFG TILDQQETLG MSGSVVPDLP

VFLPVPPNPI ATFNAPSKWP

EPQSTVSYGL AVQGAIQILP LGSGHTPQSS

SNSEKNSLPP VMAISNVENE

KQVHISFLPA NTQGFPLAPE RGLFHASLGI

AQLSQAGPSK SDRGSSQVSV

TSTVHVVNTT VVTMPVPMVS TSSSSYTTLL

PTLEKKKRKR CGVCEPCQQK

TNCGECTYCK NRKNSHQICK KRKCEELKKK

PSVVVPLEVI KENKRPQREK

KPKVLKADFD NKPVNGPKSE SMDYSRCGHG

EEQKLELNPH TVENVTKNED

```
SMTGIEVEKW TQNKKSQLTD HVKGDFSANV
PEAEKSKNSE VDKKRTKSPK
LFVQTVRNGI KHVHCLPAET NVSFKKFNIE
EFGKTLENNS YKFLKDTANH
KNAMSSVATD MSCDHLKGRS NVLVFQQPGF
NCSSIPHSSH SIINHHASIH
NEGDQPKTPE NIPSKEPKDG SPVQPSLLSL
MKDRRLTLEQ VVAIEALTQL
SEAPSENSSP SKSEKDEESE QRTASLLNSC
KAILYTVRKD LQDPNLQGEP
PKLNHCPSLE KQSSCNTVVF NGQTTTLSNS
HINSATNQAS TKSHEYSKVT
NSLSLFIPKS NSSKIDTNKS IAQGIITLDN
CSNDLHQLPP RNNEVEYCNQ
LLDSSKKLDS DDLSCQDATH TQIEEDVATQ
LTQLASIIKI NYIKPEDKKV
ESTPTSLVTC NVQQKYNQEK GTIQQKPPSS
VHNNHGSSLT KQKNPTQKKT
KSTPSRDRRK KKPTVVSYQE NDRQKWEKLS
YMYGTICDIW IASKFQNFGQ
FCPHDFPTVF GKISSSTKIW KPLAQTRSIM
QPKTVFPPLT QIKLQRYPES
AEEKVKVEPL DSLSLFHLKT ESNGKAFTDK
AYNSQVQLTV NANQKAHPLT
QPSSPPNQCA NVMAGDDQIR FQQVVKEQLM
HQRLPTLPGI SHETPLPESA
LTLRNVNVVC SGGITVVSTK SEEEVCSSSF
GTSEFSTVDS AQKNFNDYAM
NFFTNPTKNL VSITKDSELP TCSCLDRVIQ
KDKGPYYTHL GAGPSVAAVR
EIMENRYGQK GNAIRIEIVV YTGKEGKSSH
GCPIAKWVLR RSSDEEKVLC
LVRQRTGHHC PTAVMVVLIM VWDGIPLPMA
DRLYTELTEN LKSYNGHPTD
RRCTLNENRT CTCQGIDPET CGASFSFGCS
WSMYFNGCKF GRSPSPRRFR
IDPSSPLHEK NLEDNLQSLA TRLAPIYKQY
APVAYQNQVE YENVARECRL
GSKEGRPFSG VTACLDFCAH PHRDIHNMNN
GSTVVCTLTR EDNRSLGVIP

QDEQLHVLPL YKLSDTDEFG SKEGMEAKIK
SGAIEVLAPR RKKRTCFTQP
VPRSGKKRAA MMTEVLAHKI RAVEKKPIPR
IKRKNNSTTT NNSKPSSLPT
LGSNTETVQP EVKSETEPHF ILKSSDNTKT
YSLMPSAPHP VKEASPGFSW
SPKTASATPA PLKNDATASC GFSERSSTPH
CTMPSGRLSG ANAAAADGPG
ISQLGEVAPL PTLSAPVMEP LINSEPSTGV
TEPLTPHQPN HQPSFLTSPQ
DLASSPMEED EQHSEADEPP SDEPLSDDPL
SPAEEKLPHI DEYWSDSEHI
FLDANIGGVA IAPAHGSVLI ECARRELHAT
TPVEHPNRNH PTRLSLVFYQ
HKNLNKPQHG FELNKIKFEA KEAKNKKMKA
SEQKDQAANE GPEQSSEVNE
LNQIPSHKAL TLTHDNVVTV SPYALTHVAG
PYNHWV (SEQ ID NO: 10, UniProtKB-Q8NFU7 (TET1_
HUMAN), which is specifically incorporated by
reference herein in its entirety).
```

2. Isolated Nucleic Acid Molecules

Isolated nucleic acid sequences encoding TET proteins, polypeptides, fusions fragments and variants thereof, and vectors and other expression constructs encoding the foregoing are also disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-TET proteins). The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

The nucleic acid sequences encoding TET polypeptides include genomic sequences. Also disclosed are mRNA sequences wherein the exons have been deleted. Other nucleic acid sequences encoding TET polypeptides, such polypeptides that include the above-identified amino acid sequences and fragments and variants thereof, are also disclosed. Nucleic acids encoding TET polypeptides may be optimized for expression in the expression host of choice. Codons may be substituted with alternative codons encoding the same amino acid to account for differences in codon usage between the organism from which the TET nucleic acid sequence is derived and the expression host. In this manner, the nucleic acids may be synthesized using expression host-preferred codons.

Nucleic acids can be in sense or antisense orientation, or can be complementary to a reference sequence encoding a TET polypeptide. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Common modifications are discussed in more detail below.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

a. Vectors and Host Cells

Vectors encoding TET polypeptides, and fusion proteins, fragments, and variants thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen Life Technologies (Carlsbad, CA).

An expression vector can include a tag sequence. Tag sequences are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, CT), maltose E binding protein and protein A.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the TET polypeptides or fusion polypeptides described herein.

The vectors can be used to express TET in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

Nucleic acid molecules encoding polypeptides or fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

Physical means well-known in the art can be used for direct transfer of DNA, including administration of plasmid DNA and particle-bombardment mediated gene transfer.

b. Oligonucleotide Composition

The disclosed nucleic acids nucleic acids can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides include uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

i. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

ii. Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i-1 phosphate in the purine strand of the duplex.

In some embodiments, the nucleic acid is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

iii. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., *Organic. Chem.*, 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., *Chem. Biol.*, 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are composed of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the nucleic acid can be single stranded or double stranded.

C. Methods of Treatment

The disclosed methods typically include injecting or otherwise delivering a compound that increases TET bioavailability into a male gamete preferably, spermatids or haploid spermatogenic cells, oocyte, fertilized egg, or early stage embryo. In some embodiments, the compound is delivered in combination with a male gamete during, for example, intracytoplasmic sperm injection (ICSI). Thus, as used herein, ICSI refers to intracytoplasmic injection of not only sperm, but additionally or alternatively spermatids and other male gametes.

Methods for ICSI are known in the art. ICSI is an in vitro fertilization (IVF) procedure in which a single male gamete is injected directly into the cytoplasm of an egg. ICSI needs only one male gamete per oocyte, while IVF typically utilizes more than fifty thousand. By delivering the male gamete directly into the oocyte, ICSI avoids the acrosome reaction-mediated sperm entry into an oocyte that typically needs thousands of sperm.

ICSI typically utilizes a laminar flow cabinet, inverted microscope, micromanipulators, microinjectors and anti-vibration table. The procedure is done under a microscope using multiple micromanipulation devices (micromanipulator, microinjectors and micropipettes). A holding pipette stabilizes the mature oocyte with gentle suction applied by a microinjector. The microinjector is typically a hermetic syringe filled with mineral oil, controlled by micromanipulators, and connected to the microinjection pipettes (to aspirate and inject the spermatozoa) by a flexible tube.

From the opposite side a thin, hollow glass micropipette is used to collect a single sperm by applying negative pressure using a microinjector. The sperm has typically been immobilized by pressing its tail with the point of the micropipette. The oocyte is pierced through the oolemma and the sperm is delivered into the cytoplasm of the oocyte. Preferably, the polar body is positioned at the 12 or 6 o'clock position, to ensure that the inserted micropipette does not disrupt the spindle inside the egg. Next, the oocyte is cultured and checked on the following day for signs of fertilization. The method optionally includes an activation step using sperm extract and chemical activation. Sperm extract is co-injected with Tet3 and haploid round spermatids fuding ICSI. Following ICSI, reconstructed oocytes are activated by culturing five minutes in 5 μM ionomycin in TALP-Hepes medium, followed by incubation in 2 mM 6-Dimethylaminopurine (6-DMAP) in HECM-9 for five hours in a humidified atmosphere of 5% $CO_2$, 5% $O_2$ and 90% $N_2$ at 37° C.

In additional or alternative to microinjection, electroporation can be used to deliver TET proteins and/or nucleic acids (e.g., TET3 protein or nucleic acids) into oocyte. In some embodiments, this method of delivering TET constructs is used in combination with classical IVF. Thus, in some embodiments, the procedure can be carried out without an injection step, reducing mechanical damage during the procedure.

The procedure before and after insemination by classical IVF and ICSI are generally the same. For example, once fertilized, the egg is transformed into a proembryo, cultured for about 2-6 days, and transferred to the uterus.

Although compounds for increasing TET bioavailability are particularly advantageous for use with an ICSI-based gamete delivery, the disclosed methods can also be used in combination with classical IVF procedures. In such embodiments, the compound for increasing TET bioavailability may be delivered to the oocyte before or after classical in vitro fertilization, (e.g., before or after the egg is contacted with sperm). In other embodiments, the compound for increasing TET bioavailability may be delivered to a male gamete such as spermatids or haploid spermatogenic cells prior to ICSI or IVF.

Live birth rates are significantly higher with progesterone to assist implantation in ICSI cycles. Also, addition of a GNRH agonist has been estimated to increase success rates. Thus, theses additional compositions and methods can be included in the treatment.

Additionally or alternatively, in some embodiments, the method includes ultra-high magnification sperm injection (IMSI). IMSI includes a selection step referred to as motile sperm organelle morphology examination (MSOME) and the spermatozoa are selected under high magnification (over 6000×) prior to ICSI.

Sperm selection for ICSI can also include testing for binding to hyaluronan, the main constituent of the gel layer (*Cumulus oophorus*) surrounding the oocyte. In an exemplary method, a device (e.g., a PICSI® device) provides microscopic droplets of hyaluronan hydrogel attached to the culture dish. The practitioner places the prepared sperm on the microdot, selects and captures sperm that bind to the dot. Basic research on the maturation of sperm shows that hyaluronan-binding sperm are more mature and show fewer DNA strand breaks and significantly lower levels of aneuploidy than the sperm population from which they were selected.

In some embodiments, the gametes are treated with the compound during differentiation, for example in vitro differentiation.

The disclosed compounds are typically administered into the gamete or embryo in a carrier, preferably a pharmaceutically acceptable carrier. In a preferred embodiment, the compositions are suspended in a suitable sperm extract buffer suitable for injection into oocytes (Simerly et al., (2003) *Cloning and Stem Cells* 5(4) 319-331; Swann (1990) *Development* 110, 1295-1302; Stice et al., (1988) *Biol Reprod* 39,657-664), for example, KCL (Sigma P4505), HEPES (Sigma H6147), EGTA (Sigma E3889), and sodium glycerophoaste (Sigma G-5422). An exemplary buffer formulation is shown in the Table 2.

D. Sources of Gametes

Female gametes are called ova, oocytes, or egg cells. Male gametes are called sperm, however it will be appreciated that male gametes as used herein include both mature sperm, and immature sperm, for example, round spermatids, elongating spermatids, condensing spermatids, or condensed spermatids. Gametes are haploid cells, and each cell carries only one copy of each chromosome.

Like classical IVF, ICSI is generally performed following a transvaginal oocyte retrieval procedure to extract one to several oocytes from a woman or laporascopic aspiration in nonhuman primates. Additional techniques that are routinely used in IVF, and thus can be included as part of the disclosed methods, include ovarian hyperstimulation to generate multiple eggs or ultrasound-guided transvaginal oocyte retrieval directly from the ovaries; after which the ova and sperm are prepared, as well as culture and selection of resultant embryos before embryo transfer into a uterus.

Male gametes for use in the disclosed methods can be obtained in a variety of ways. Sperm can be isolated from a donor subject. For example, a male partner or a donor can provide a sperm sample (e.g., on the same day when the eggs are collected). If no sperm is present in the sample, doctors can extract sperm from the epididymis or testicle. The extraction of sperm from epididymides is also known as percutaneous epidydimal sperm aspiration (PESA) and extraction of sperm from testicles is also known as testicular sperm aspiration (TESA).

Many infertile men produce immature spermatids (round spermatids) in their testes. Testis biopsies are standard procedures for obtaining immature spermatids, but the success rates of fertilizing their partner's eggs is typically extremely low. However, it is believed that increasing TET bioavailability will improve fertilize rates and/or viable embryos derived therefrom. Thus, in some embodiments, the male gametes are immature spermatids.

Furthermore, human and non-human primate embryonic (ESCs) and induced pluripotent stem cells (iPSCs) can be induced to differentiate directly into advanced male germ cell lineages including post-meiotic, spermatid-like cells in vitro without genetic manipulation. Such methods are discussed in more detail below.

III. Methods of Making Gametes

Methods of making male gametes in vitro are also provided. The methods can be used alone or in combination with the disclosed methods of increasing TET bioavailability and/or correcting genomic mutations.

Human and non-human primate embryonic (ESCs) and induced pluripotent stem cells (iPSCs) can be induced to differentiate directly into advanced male germ cell lineages. See, e.g., the working Examples below and Easley I V, et al., *Cell Rep.* 2(3): 440-446 (2012) doi:10.1016/j.celrep.2012.07.015, which along with all of its supplementary material, is specifically incorporated by reference in its entirety. The Examples below show that such spermatid-like cells can be used as a source of male gametes for ICSI, which leads to a fertilized egg and subsequent development through the blastocyst stage.

Briefly, Easley I V, supra, describes that ESCs and iPSCs can be differentiated into spermatid-like cells over 10 days in mouse spermatogonial stem cell (SSC) medium which generally contains some or all of the following: MEMalpha, Bovine Serum Albumin, insulin, transferrin, putrescine, L-glutamine, β-mercaptoethanol, hbFGF (human basic fibroblast growth factor), 20 ng/ml GDNF (glial-derived neurotrophic factor), sodium selenite, palmitic acid, palmitoleic acid, stearic acid, oleic acid, linoleic acid, linolenic acid, HEPES, and penicillin/streptomycin. Spermatid-like cells can be selected from other cells (e.g., undifferentiated), using FACS, morphological analysis, marker expression, or a combination thereof. Post-meiotic, sperm markers include, for example, acrosin, protamine 1, and transition protein 1.

In some preferred embodiments, the culture conditions for differentiation do not include feeder cells for example, mouse STO feeder cells. Preferably, ESCs/iPSCs cells are cultured in hESC conditions for 2-5 days prior to culturing in differentiation medium. In order to compile with Good Manufacturing Practice (GMP), all animal derived products and cells need to be eliminated for clinical application. Therefore, a differentiation protocol which does not rely on the support of the STO feeder cells is highly desirable.

Source of ESCs and iPSCs are known in the art. For example, embryonic stem cells are generally derived from embryos that are three to five days old. Any somatic cell may a source for reprogramming into an iPSC. Preferred sources and basic methods of reprogramming are known in the art, see, e.g., Raab, et al., Stem Cells International, Volume 2014, Article ID 768391, 12 pages, (2014) doi: 10.1155/ 2014/768391. Exemplary sources include, but are not limited to, fibroblasts, the most commonly used primary somatic cell type for the generation of induced pluripotent stem cells, as well as peripheral blood, umbilical cord blood, cells from urine, multipotent stem cells, cells of hematological origin, cells of embryonic origin, skin derived cells, adipose cells, epithelial cells, endothelial cells, parenchymal cells, neurological cells, and connective tissue. Specific examples include exfoliated renal epithelial cells, keratinocytes, stratified squamous epithelium, multipotent mesenchymal stem cells (MSCs), hepatocytes, synovial cells, mesenchymal stromal cells, adult stem cells, and amniotic epithelial cells.

There are certain infertile male patients who do not produce any gametes but possess spermatogonia stem cells, which are stem cells that in normal patients produce sperm after puberty. For these patients, spermatogonial stem cells can be isolated from their testis tissue and differentiated as disclosed herein to produce spermatids.

IV. Methods of Correcting Mutations

Compositions and methods of correcting genomic mutations are also provided for use alone or in combination with other compositions and methods disclosed herein. Some embodiments include steps of correcting mutations or otherwise modifying the genome of male gamete progenitor cells before they are differentiated into spermatids. For example, in some embodiments somatic cells such as ESCs, iPSCs, or iPSCs source cells (e.g., fibroblasts, etc.) prior to reprogramming can be subjected to a genome editing. Generally, the cells are contacted (e.g., transformed) with an effective amount of a gene editing composition ex vivo to induce a specific genomic modification therein.

Advantageously, the cells can be screened for targeted genetic modification prior to differentiation to spermatids. For example, PCR, whole genome sequencing, or other art-recognized methods can be used to analyze the genetically modified cells prior to the creation of spermatids or embryos to ensure to precise genetics of offspring prior to clinical use. The resulting embryos and offspring are constituted by parental genome contributed through male and female germ cells, thus all resulting offspring will not be a mosaic.

In some embodiments, a fertilized egg or early stage embryo (e.g., a blastocyte) is contacted (e.g, transformed, injected, etc.) with an effective amount of a gene editing composition ex vivo to induce a specific genomic modification therein. In some embodiments, the gene editing composition is delivered to the oocyte in combination with the male gamete and optionally in further combination with a compound that increases TET bioavailability (e.g., by injection during ICSI).

A. Gene Editing Compositions

Gene editing compositions can include nucleic acids that encode an element or elements that induce a single or a double strand break in the target cell's genome, and optionally a polynucleotide. The compositions can be used, for example, to correct disease causing mutations including, but not limited to, those described below.

1. Strand Break Inducing Elements a. CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science*, 15:339(6121):819-823 (2013) and Jinek, et al., *Science*, 337(6096):816-21 (2012)). By transfecting a cell with the required elements including a Cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science*, 15:339(6121):819-823 (2013) and Jinek, et al., *Science*, 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

In some embodiments, one or more elements of a CRISPR system is derived from a type I, type II, or type III CRISPR system. In some embodiments, one or more elements of a CRISPR system is derived from a particular organism including an endogenous CRISPR system, such as *Streptococcus pyogenes*.

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence can be any polynucleotide, such as DNA or RNA polynucleotides. In some embodiments, a target sequence is located in the nucleus or cytoplasm of a cell.

In the target nucleic acid, each protospacer is associated with a protospacer adjacent motif (PAM) whose recognition is specific to individual CRISPR systems. In the *Streptococcus pyogenes* CRISPR/Cas system, the PAM is the nucleotide sequence NGG. In the *Streptococcus* thermophiles CRISPR/Cas system, the PAM is the nucleotide sequence is NNAGAAW. The tracrRNA duplex directs Cas to the DNA target consisting of the protospacer and the requisite PAM via heteroduplex formation between the spacer region of the crRNA and the protospacer DNA.

Typically, in the context of an endogenous CRISPR system, formation of a CRISPR complex (including a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. All or a portion of the tracr sequence may also form part of a CRISPR complex, such as by hybridization to all or a portion of a tracr mate sequence that is operably linked to the guide sequence.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites.

For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element can be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector includes one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector includes an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector includes two or more insertion sites, each insertion site being located between two tracr mate sequences so as to allow insertion of a guide sequence at each site. In such an arrangement, the two or more guide sequences can include two or more copies of a single guide sequence, two or more different guide sequences, or combinations of these. When multiple different guide sequences are used, a single expression construct may be used to target CRISPR activity to multiple different, corresponding target sequences within a cell. For example, a single vector can include about or more than about 1, 2, 3, 4, 5, 6, 7, 8, 9, 10, 15, 20 guide sequences. In some embodiments, about or more than about 1, 2, 3, 4, 5, 6, 7, 8, 9, 10, such guide-sequence-containing vectors may be provided, and optionally delivered to a cell.

In some embodiments, a vector includes a regulatory element operably linked to an enzyme-coding sequence encoding a CRISPR enzyme, such as a Cas protein.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III) can be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%>, 1%>, 0.1%>, 0.01%, or lower with respect to its non-mutated form.

In some embodiments, an enzyme coding sequence encoding a CRISPR enzyme is codon optimized for expression in particular cells, such as eukaryotic cells. The eukaryotic cells can be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules.

The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al., *Nucl. Acids Res.,* 28:292 (2000). Computer algorithms for codon optimizing a particular sequence for expression in a particular host cell, for example Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme including one or more nuclear localization sequences (NLSs). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors.

Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In some embodiments, one or more of the elements of CRISPR system are under the control of an inducible promoter, which can include inducible Cas, such as Cas9.

Cong, *Science*, 15:339(6121):819-823 (2013) reported heterologous expression of Cas9, tracrRNA, pre-crRNA (or Cas9 and sgRNA) can achieve targeted cleavage of mammalian chromosomes. Therefore, CRISPR system utilized in the methods disclosed herein can be encoded within a vector system which can include one or more vectors which can include a first regulatory element operably linked to a CRISPR/Cas system chimeric RNA (chiRNA) polynucleotide sequence, wherein the polynucleotide sequence includes (a) a guide sequence capable of hybridizing to a target sequence in a eukaryotic cell, (b) a tracr mate sequence, and (c) a tracr sequence; and a second regulatory element operably linked to an enzyme-coding sequence encoding a CRISPR enzyme which can optionally include at least one or more nuclear localization sequences. Elements (a), (b) and (c) can arranged in a 5' to 3 orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex can include the CRISPR enzyme complexed with (1) the guide sequence that is hybridized to the target sequence, and (2) the tracr mate sequence that is hybridized to the tracr sequence, wherein the enzyme coding sequence encoding the CRISPR enzyme further encodes a heterologous functional domain. In some embodiment, one or more of the vectors encodes also encodes a suitable Cas enzyme, for example, Cas9. The different genetic elements can be under the control of the same or different promoters.

While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

b. Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fold. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31, 978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

c. Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, *Nucl. Acids Res.* 1-11 (2011). US Published Application No. 2011/0145940, which discloses TAL effectors and methods of using them to modify DNA. Miller et al. *Nature Biotechnol* 29: 143 (2011) reported making TALENs for site-specific nuclease architecture by linking TAL truncation variants to the catalytic domain of FokI nuclease. The resulting TALENs were shown to induce gene modification in immortalized human cells. General design principles for TALE binding domains can be found in, for example, WO 2011/072246.

2. Gene Altering Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Thus, the subject methods can be used to knock out a gene (resulting in complete lack of transcription or altered transcription) or to knock in genetic material into a locus of choice in the target DNA.

Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

Donor sequences can also include a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence can include certain sequence differences as compared to the genomic sequence, e.g., restriction sites, nucleotide polymorphisms, selectable markers (e.g., drug resistance genes, fluorescent proteins, enzymes etc.), etc., which can be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence can be a single-stranded DNA, single-stranded RNA, double-stranded DNA, or double-stranded RNA. It can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. *Proc. Natl. Acad. Sci. USA* 84:4959-4963 (1987); Nehls et al. *Science* 272:886-889 (1996). Additional methods for protecting exogenous polynucleotides from degradation include, but are not limited to, addition of terminal amino group(s) and the use of modified internucleotide linkages such as, for example, phosphorothioates, phosphor amidates, and O-methyl ribose or deoxyribose residues.

As an alternative to protecting the termini of a linear donor sequence, additional lengths of sequence can be included outside of the regions of homology that can be degraded without impacting recombination. A donor sequence can be introduced into a cell as part of a vector molecule having additional sequences such as, for example, replication origins, promoters and genes encoding antibiotic resistance.

B. Target Diseases

The disclosed methods of gene editing can be used to treat a variety of genetic diseases and disorders. Embodiments in which the treated cells are ESCs, iPSCs, or male gametes (e.g., spermatids cells), are particularly beneficial for correcting paternally inherited dominant genetic diseases and recessive genetic diseases (e.g., that need two mutated copies of parental alleles). By permanently correcting paternal mutations, the genetic anomaly causing the problem can be diluted and ultimately eradicated over future generations.

Exemplary inherited dominant genetic disorders include, but are not limited to, Huntington's Disease, Spinocerebellar Ataxia (SCA), Fragile-X syndrome etc. Exemplary recessive genetic diseases include, but are not limited to, cystic fibrosis, sickle cell anemia, Tay-Sachs etc.

In some embodiments, the disease is a monogenic disease. Monogenic diseases for which the disease genotype is known include, but are not limited to, achondroplasia, adrenoleukodystrophy, alpha thalassaemia, alpha-1-antitrypsin deficiency, alport syndrome, amyotrophic lateral sclerosis, beta thalassemia, Charcot-Marie-Tooth, congenital disorder of glycosylation type 1a, crouzon syndrome, cystic fibrosis, Duchenne and Becker muscular dystrophy, dystonia 1, torsion, Emery-Dreifuss muscular dystrophy, facioscapulohumeral dystrophy, familial adenomatous polyposis, familial amyloidotic polyneuropathy, familial dysautonomia, fanconi anaemia, fragile x, glutaric aciduria type 1, haemophilia a and b, hemophagocytic lymphohistiocytosis, holt-oram syndrome, Huntington's disease, hyperinsulinemic hypoglycemia, hypokalaemic periodic paralysis, incontinentia pigmenti, lynch syndrome, marfan syndrome, menkes disease, metachromatic leukodystrophy, mucopolysaccharidosis type II (Hunter syndrome), multiple endocrine neoplasia (MEN2), multiple exostosis, myotonic dystrophy, neurofibromatosis type i and ii, non-syndromic sensorineural deafness, Norrie syndrome, osteogenesis imperfecta (brittle bone disease), polycystic kidney—autosomal dominant, polycystic kidney—autosomal recessive, Pompe's syndrome, sickle cell anaemia, Smith-Lemli-Opitz syndrome, spastic paraplegia 4, spinal and bulbar muscular atrophy, spinal muscular atrophy, spinocerebellar ataxia 1, 2 and 3, spondylometaphyseal dysplasia (schmidt), Tay-Sachs disease, Treacher Collins, tuberous sclerosis, and Von Hippel-Lindau syndrome. In some embodiments, a gene editing composition that can correct a mutation or genetic anomaly is delivered (e.g., transfection, injection, etc.) into ESCs, iPSCs, male gametes (e.g., spermatids cells), a fertilized egg, or early stage embryo in an effective amount to correct the mutation or genetic anomaly. In some embodiments, the disease is an autistic spectrum disorder (ASD), and gene editing composition targets one or more mutations or genetic anomalies associated therewith. There are currently no cures for ASD, and treatments are only available for particular symptoms pertaining to a child's development. It is a devastating disorder that has significant social and economic impact as the number of children affected increases. The diagnosis of ASD is primarily based on deficits in all of the following: reciprocal social interaction, communication and stereotyped behaviors. In populations of diagnosed children, 15-70% exhibit intellectual impairments. The fundamental diagnosis for ASD is homogeneous, based on the criteria listed above; however, ASD can also co-exist in patients with syndromes such as Fragile X or neurofibromatosis.

Genetic studies of ASD have yielded an intriguing list of select genomic targets with several of the genes directly linked to the regulation of critical synaptic functions, including FMR1, MECP2, PTEN, UBE3A, NLGN1-NLGN4, NRXN1 and SHANK3. Moreover, some of the candidates, such as SHANK3, are associated to ASD in a gene-dosage-dependent manner SHANK3, a gene integral to the glutamatergic pathway, is a binding partner for the neuroligins NLGN3 and NLGN4, which themselves bind neurexins, all of which are genetically associated with ASD progression. Additionally, mutations in genes downstream of SHANK3 signaling, such as DIAPH3, have also been linked to ASD. Consequently, disruption of SHANK3-mediated glutamatergic transmission appears to play a pivotal role in ASD pathogenesis. Moreover, the chromosomal location of SHANK3 at 22q13 is linked to considerable human pathology due to genetic deletions which result in SHANK3 haploinsufficiency and strong phenotypes of developmental and language delays.

C. Genetic Testing and Selection

Some embodiments include a step of genetic testing and/or selection of edited cells. Such techniques are known in the art. For example, cells and embryos can be screened using genetic sequencing and/or PCR-based methods for detection of mutations (or correction thereof) and FISH for chromosomal abnormalities. Protocols include, for example, prenatal diagnosis, pre-implantation genetic diagnosis, pre-implantation genetic screening (PGS), oocyte selection, sperm selection, etc.

V. Non-Clinical Applications

Although generally described herein with respect to methods of treatment, the disclosed compositions and methods also have applications outside the clinic. For example, disclosed methods can be used to generate functional spermatids from rare or endangered animals-species preservation, or otherwise improve methods of assisted reproduction thereof. Spermatids can be generated from male animals that are unable to breed or have gone sterile due to age, thus allowing the preservation of rare or endangered mammals.

The disclosed methods can also be used to prepare gene targeted haploid spermatids for the creation of hemizygotic or semi-cloned embryos by fertilizing mature oocytes (e.g. monkeys), which is an ideal method to create animal models of haploinsufficiency-associated diseases such as Mendelian susceptibility to mycobacterial disease (MSMS) and Ehlers-Danlos syndrome etc. Thus, in some embodiments (and as in the working example below), the gene editing methods are used to induce a disease or dysfunction-causing mutation to, for example, further its study.

In some embodiments, an oocyte activation approach is used to improve somatic cell nuclear transplantation (SCNT), parthenogenic embryos and improve ICSI and ROSI efficiency. Synthetic TET3 or another TET gene family protein treatment could potentially improve efficiency of all of the above applications.

In some embodiments, the compositions and methods are used too improve the making of patient-specific stem cell lines for therapeutic approaches. These stem cells can be used, for example, in combination with somatic cell nuclear transfer (SCNT) for generating patient-specific stem cells.

EXAMPLES

Figure 2A:
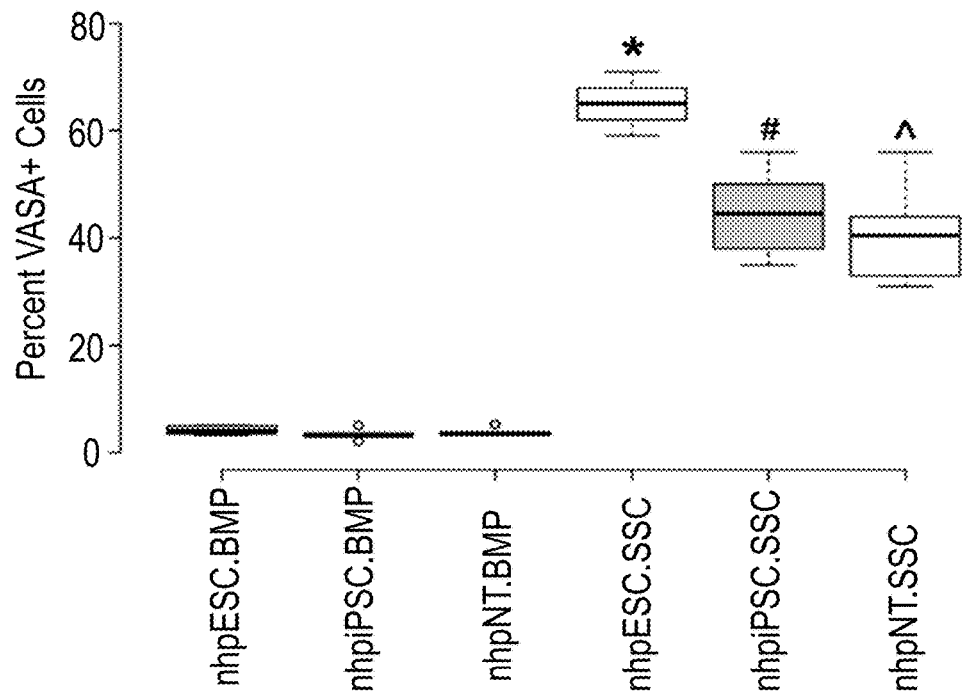
FIG. 2A is a graph showing VASA protein expression in nhpESCs, nhpiPSCs, and nhpNT-ESCs (nuclear transfer derived ESCs) cultured in mouse SSC culture conditions for 10 days compared to cells differentiated for 14 days using a BMP cocktail. *, #, and ^all represent statistical significance $p<0.01$.

Example 1: In Vitro Differentiated Spermatids can Fertilize Oocytes, Divide and Form Blastocysts in Culture Materials and Methods
NHP Embryonic Stem Cell Differentiation.
Male Rhesus macaque embryonic stem cell line (Navara et al., Stem Cells 25, 2695-2704, doi:2007-0286 [pii] 10.1634/stemcells.2007-0286 (2007)) stably transduced with H2B-GFP was differentiated as previously described (Easley et al., Cell Rep 2, 440-446, doi:10.1016/j.celrep.2012.07.015 (2012)). For FIG. 2A, the same non-transduced line was used in addition to a rhesus induced pluripotent stem cell (nhpiPSC) line and a somatic cell nuclear transfer embryonic stem cell (nhpNT) line (Byrne et al., Nature 450, 497-502, doi:10.1038/nature06357 (2007)). Briefly, nhp pluripotent stem cell lines were cultured for 10 days on STO-feeder cells in mouse spermatogonial stem cell (SSC) medium containing the following: MEMalpha (Thermofisher), 0.2% Bovine Serum Albumin (Sigma), 5 µg/ml insulin (Sigma), 10 µg/ml transferrin (Sigma), 60 µM putrescine (Sigma), 2 mM L-glutamine (Invitrogen), 50 µM β-mercaptoethanol (Sigma), 1 ng/ml hbFGF (human basic fibroblast growth factor, R&D Systems), 20 ng/ml GDNF (glial-derived neurotrophic factor, R&D Systems), 30 nM sodium selenite (Sigma), 2.36 µM palmitic acid (Sigma), 0.21 µM palmitoleic acid (Sigma), 0.88 µM stearic acid (Sigma), 1.02 µM oleic acid (Sigma), 2.71 µM linoleic acid (Sigma), 0.43 µM linolenic acid (Sigma), 10 mM HEPES (Sigma), and 0.5× penicillin/streptomycin (Thermofisher). Cells were refed with fresh medium every other day and SSC medium was gassed with a blood gas mixture (5% $CO_2$, 5% $O_2$, 90% nitrogen gas) prior to use. For comparison in FIG. 2A, nhpESC H2B-GFP cells were differentiated with a BMP mixture as described (Kee et al., Nature 462, 222-225, doi:nature08562 [pii]10.1038/nature08562 (2009)) without the addition of DAZL, DAZ, and BOULE.

Haploid Cell Isolation, Cell Cycle Profiling, Fluorescence in situ Hybridization (FISH).
To isolate haploid cells during fluorescence-activated cell sorting (FACS), differentiated H2B-GFP nhpESCs were trypsinized and stained with RedDot1 DNA stain (Biotium) as per manufacturer's instructions in the SSC medium listed above. Haploid cells were then cultured on poly-d-lysine-coated coverslips and fixed with 4% para-formaldehyde prior to immunostaining (see below).

For cell cycle profiling, differentiated cultures were trypsinized and stained using the Cell Cycle Kit for the Millipore MUSE cell analyzer as per manufacturer's instructions (EMD Millipore).

To determine diploidy and haploidy on interphase cells, hPSCs or isolated haploid cells were attached to microscope slides by cytospin at 180×g for 6 minutes. Slides were then fixed in Carnoy's fixative (3:1 methanol to glacial acetic acid) for 5 minutes at room temperature and then air-dried. Slides were dehydrated by successive ice-cold ethanol treatments for 2 minutes each (100%, 80% and 70%) and then air-dried. Cytogenetic preparations were then denatured at 75° C. in 70% formamide for 5 minutes while the custom LNA probe against satellite DNA on chromosomes 1 and Y (Exiqon) was simultaneously denatured at 75° C. in hybridization buffer (50% formamide/2×SSC, pH 7.0/10% dextran sulfate) for 5 minutes. LNA probe was hybridized onto samples overnight at 37° C. Following hybridization, slides were washed in 0.25×SSC for 5 minutes at 60° C. followed by a second wash in 2×SSC/0.1% Tween-20 for 5 minutes at 60° C. Samples were then mounted with Vectashield with DAPI and imaged.

Immunostaining and RT-PCR.
nhpESCs cultured in conditions described above were fixed in 4% paraformaldehyde (Sigma) for 15 minutes and then blocked with buffer containing 1× Phosphate-buffered Saline Solution (PBS) (Thermofisher), 0.25% Triton X (Sigma), 5% bovine serum albumin (BSA) (Fisher Scientific) and 5% normal goat serum (NGS) or donkey serum (Sigma) overnight at 4° C. Primary antibody incubation occurred overnight at 4° C. in blocking buffer followed by 3 washes in 1×PBS with 0.25% Triton-X for 10 minutes each at room temperature. Secondary antibody (Thermofisher 1:2000 dilution) incubation was performed at room temperature for 2 hours followed by 3 washes as described above. Samples were co-stained with Hoechst. For FACS-obtained haploid cells, isolated cells were seeded onto poly-d-lysine coated coverslips for 10 minutes at 37° C. Coverslips were then fixed in 4% paraformaldehyde and stained as described above. Additionally, rhesus testis cell suspensions were seeded onto poly-d-lysine coated coverslips for 10 minutes at 37° C. VASA, UTF1, and PLZF antibodies were from R&D Systems. PIWIL1 and PIWIL2 antibodies were from Abcam. Acrosin, Protamine 1, and Transition Protein 1 were from Santa Cruz Biotechnology. Acetylated tubulin antibody was from Thermofisher. All fluorescent secondary antibodies were from Thermofisher. All images shown are representative of at least 5 separate immunostaining experiments. For VASA+ counts, 5000 cells were counted for each differentiation and each differentiation was performed 5 times (n=5). Percentages of total cell counts were calculated and averaged for the 5 trials.

For RT-PCR, custom PrimePCR arrays (Bio-Rad) were designed with validated PCR primers to primate genes DAZL, DDX4, GFRA1, GPR125, PIWIL1, PIWIL2, ZBTB16, SYCP3, THY1, CKIT, ACR, PRM1, PRM2, GAPDH, ACTB, and TNP1. Assays were run according to manufacturer's instructions. For each plate, there were 2 replicates and 3 plates were run representing 3 separate and distinct biological replicates. Normalized fold change (2^δCT) is shown.

Genomic Imprint Analyses for H19 and SNRPN.
Genomic DNA from diploid nhpESCs and haploid cells obtained from FACS were obtained using the DNeasy Blood and Tissue kit from Qiagen following manufacturer's instructions. Samples were prepared for imprint control region methylation analyses with the Epitect Methyl DNA Restriction Kit (Qiagen) as per manufacturer's instructions. For qPCR-based analyses of imprint control region methylation for H19 and SNRPN for each sample, the following Epitect qPCR Methyl Promoter Primers were used: H19-catalog number: 335002 EPHS102101-1A, SNRPN-335002 EPHS104389-1A. % Methylation for H19 and SNRPN imprint control regions were calculated for each sample as per manufacturer's instructions (Qiagen).

Round Spermatid Isolation, Oocyte Collection, and Intracytoplasmic Sperm(atid) Injection (ICSI).

Hyperstimulation of female rhesus monkeys exhibiting regular menstrual cycles was induced with exogenous gonadotropins. Beginning at menses, females were given recombinant human FSH (r-hFSH; Organon Inc., West Orange, NJ; 35 IU, i.m.) for six days, administered twice daily, followed by one-to-three days of r-hFSH+r-hLH (r-hLH; Ares Serono; 30 IU each, i.m.), twice daily, and subcutaneous injections of a GnRH antagonist (Acyline; NICHD/NIH; 75 mg/kg body weight), once daily. Ultrasonography was performed on day seven of the stimulation to confirm adequate follicular response. When there were follicles 3-4 mm in diameter, an i.m. injection of 1500 IU r-hCG (Serono, Randolph, MA) was administered for ovulation and metaphase II (MII) oocytes were retrieved at ~35 hours post-r-hCG injection for intracytoplasmic spermatid injection (ICSI) (Arthur Chang, & Chan, *Methods Mol Biol* 770, 337-363, doi:10.1007/978-1-61779-210-6_13 (2011)).

After 10 day differentiations, round spermatids were isolated by trypsinizing cultures and spotting cells into ICSI injection medium. Round spermatids were picked for ICSI using morphological characteristics outlined by Tanaka et al. (Tanaka et al., *Proc Natl Acad Sci USA* 112, 14629-14634, doi:10.1073/pnas.1517466112 (2015), Tanaka et al., *Fertil Steril* 110, 443-451, doi:10.1016/j.fertnstert.2018.04.033 (2018)). In a vertical array, round spermatids were resuspended in 5 µl drop of SSC differentiation medium and placed onto a petri dish. A second 5 µl drop contain a mixture 1 µl (TET3 protein), 1 µl of TET3 plasmid DNA (~1 ng/µl) and 3 µl of sperm cytoplasmic factor (SCF) (Simerly & Navara, *Cloning Stem Cells*, 5, 319-331, doi:10.1089/153623003772032826 (2003)). The third 5 µl drop of TL-HEPES was placed at the bottom where oocytes were placed for ICSI. A ICSI micropipette (~9 µm inner diameter) was used to aspirate round spermatids, washed in TET3-SCF mixture, followed by cytoplamic injection into MII oocytes at position 90 degree away from the first polar body. After ICSI, fertilized oocytes were placed into HECM-9 culture medium with 10 nM of Trichostatin A (TSA; Sigma T1952) for 10 hours followed by thorough wash and placed in HECM-9 media for in vitro culture.

In vitro fertilization using spermatids is similar to intracytoplasmic sperm injection (ICSI). In brief, sorted haploid round spermatids can be co-injected with sperm extract and Tet3 protein into mature oocyte followed by in vitro culture using established assisted reproduction protocols. Preimplantation embryos can be in vitro cultured until blastocyst for developmental assessment.

Statistics.

2-tailed, unequal variance t-tests were performed to establish significance for various experiments within this study. Significance was determined as p<0.5. Graphical analyses shown are indicative of average values+/−standard deviation. For all experiments, greater than 3 trials were performed, and data are representative of all trials.

Results

Human pluripotent stem cells (hPSCs) have been differentiated, including into human embryonic (hESCs) and induced pluripotent stem cells (hiPSCs), into germ cell lineages (Easley et al., *Cell Rep* 2, 440-446, doi:10.1016/j.celrep.2012.07.015 (2012), Hayashi et al., *Cell* 146, 1-14, doi:10.1016/j.cell.2011.06.052 (2011), Kee et al., *Nature* 462, 222-225, doi:nature08562 [pii]10.1038/nature08562 (2009), Panula et al., *Hum Mol Genet* 20, 752-762, doi: ddq520 [pii]10.1093/hmg/ddq520 (2011), Zhao et al., *Stem Cell Reports* 10, 509-523, doi:10.1016/j.stemcr.2018.01.001 (2018)). In some cases, production of spermatogonia-like cells, primary and secondary spermatocyte-like cells, and haploid spermatid-like cells were shown (Easley et al., *Cell Rep* 2, 440-446, doi:10.1016/j.celrep.2012.07.015 (2012), Zhao et al., *Stem Cell Reports* 10, 509-523, doi:10.1016/j.stemcr.2018.01.001 (2018)). However, in these studies the "Gold Standard" (Handel et al., *Cell* 157, 1257-1261, doi: 10.1016/j.cell.2014.05.019 (2014)) for producing functional gametes that could fertilize an oocyte was not assessed. Work in rodents has demonstrated the ability to produce live offspring from sperm cells generated by testicular grafts of in vitro differentiated mouse precursor germ cells (Hayashi et al., *Cell* 146, 1-14, doi:10.1016/j.cell.2011.06.052 (2011)). Additionally, complete meiosis from differentiating mouse embryonic stem cells has been achieved (Zhou, et al., *Cell Stem Cell*, 18, 330-340, doi:10.1016/j.stem.2016.01.017 (2016)). Yet there are distinct biological and kinetic differences between rodents and humans (Ehmcke et al., *Hum Reprod Update* 12, 275-282, doi: 10.1093/humupd/dmk001 (2006), Fayomi & Orwig, *Stem Cell Res* 29, 207-214, doi:10.1016/j.scr.2018.04.009 (2018)). Additionally, functional male gametes have not been derived completely in vitro from rodent pluripotent stem cells.

To test whether functional gametes can be derived completely in vitro from pluripotent stem cells, a model more relevant to humans was used: a non-human primate (NHP), rhesus macaque model. Unlike rodents, NHP such as rhesus macaque share similar biological mechanisms to human spermatogenesis, fertilization, early embryo and fetal development (Ehmcke et al., *Hum Reprod Update* 12, 275-282, doi:10.1093/humupd/dmk001 (2006), Fayomi & Orwig, *Stem Cell Res* 29, 207-214, doi:10.1016/j.scr.2018.04.009 (2018)). Spermatogenesis in NHPs is more kinetically similar to humans than rodents. Fertilization is also different in rodents versus primates in that successful fertilization requires paternal centriole inheritance in both nonhuman primates and humans but not in rodents (Navara, *Reprod Fertil Dev* 7, 747-754 (1995), Schatten & Simerly, *EMBO reports* 16, 1052-1054, doi:10.15252/embr.201540875 (2015), Simerly et al., *Nat Med* 1, 47-52 (1995)). Taken together, NHP models of spermatogenesis are more similar to humans than rodent models and thus represent an ideal and necessary model for exploring stem cell-based therapies for male infertility prior to clinical use.

Figure 2B:
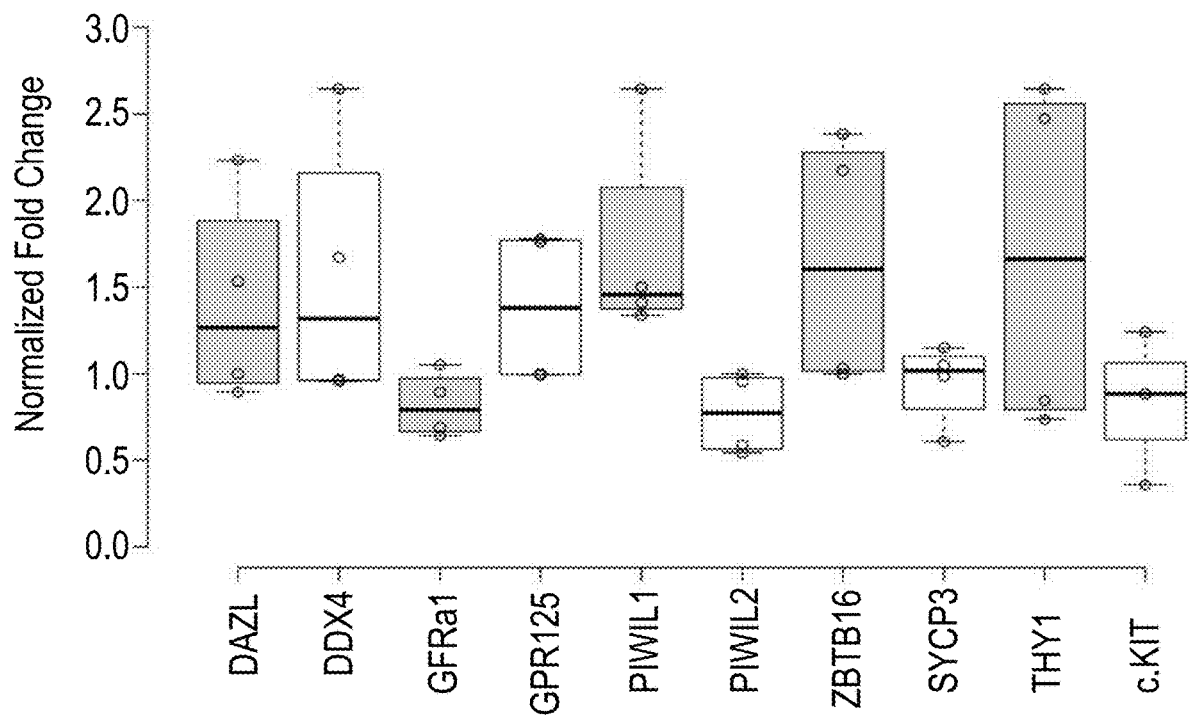
FIG. 2B is a graph showing normalized fold change ($2^{\char`\^} \delta CT$) for germline-related genes (DAZL, DDX4, GFRa1, GPR125, PIWILL PIWIL2, ZBTB16, SYCP3, THY1, cKit) in nhpESC H2B-GFP cells differentiated for 10 days in SSC conditions.
Figure 2C:
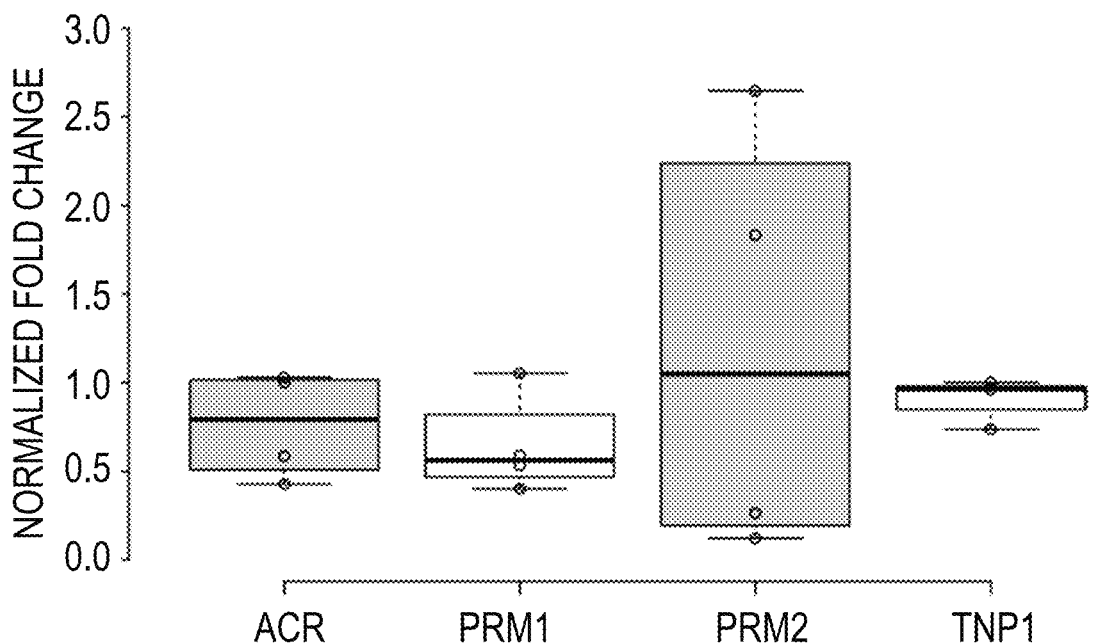
FIG. 2C is a graph showing normalized fold change ($2^{\char`\^} \delta CT$) for haploid spermatid-related genes (ACR, PRM1, PRM2, THP1) in nhpESC H2B-GFP cells differentiated for 10 days in SSC conditions.
Figure 2D:
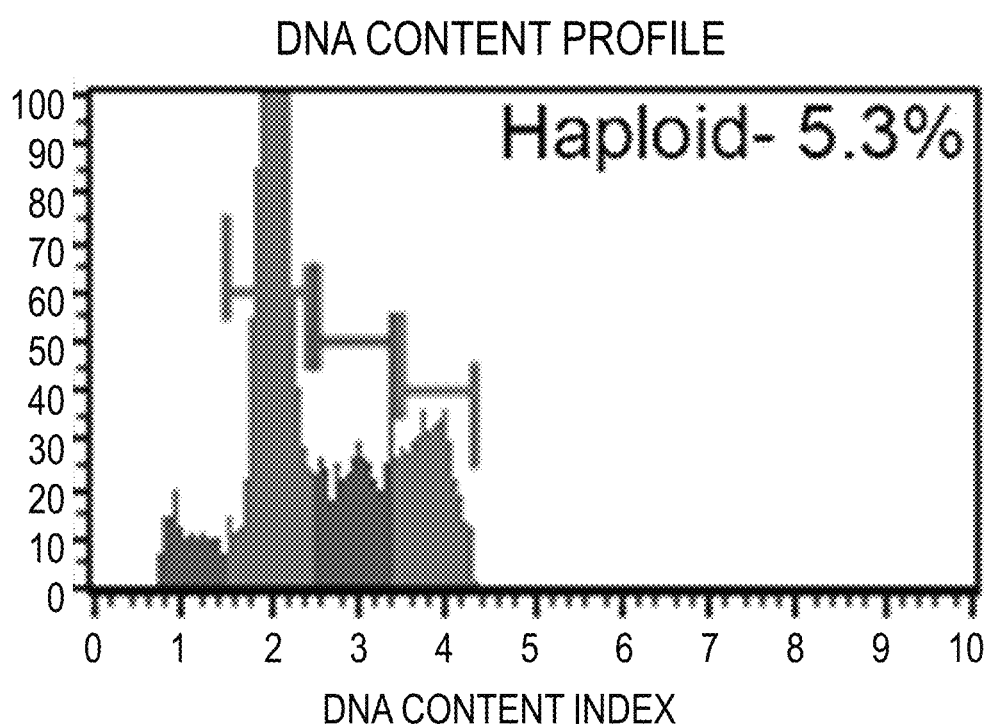
FIG. 2D is a histogram showing a representative cell cycle flow cytometry profile of nhpESC H2B GFP cells differentiated in SSC conditions for 10 days. The first peak represents the 1N peak, the second peak represents the 2N peak, the third peak represents S phase, and the fourth peak represents the 4N peak. Fluorescence in situ hybridization (FISH) confirmed haploidy of round spermatid like cells.
Figure 3A:
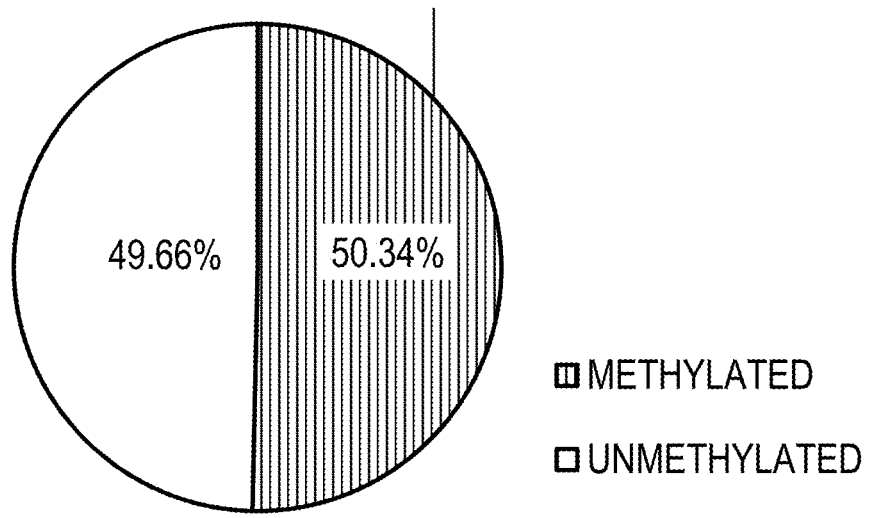
FIGS. 3A-3D are pie graphs comparing DNA methylation on imprint control regions (ICRs) for H19 (paternally silenced) and SNRPN (paternally expressed) in haploid spermatids and diploid cells. Diploid parent nhpESC H2B-GFP cells show ~50% methylation for both H19 (3A) and SNRPN (3B) whereas haploid round spermatid-like cells show high levels of DNA methylation on the paternally silenced ICR H19 (3C) and low levels of DNA methylation on the paternally expressed ICR SNRPN (3D) similar to rhesus sperm.
Figure 3B:
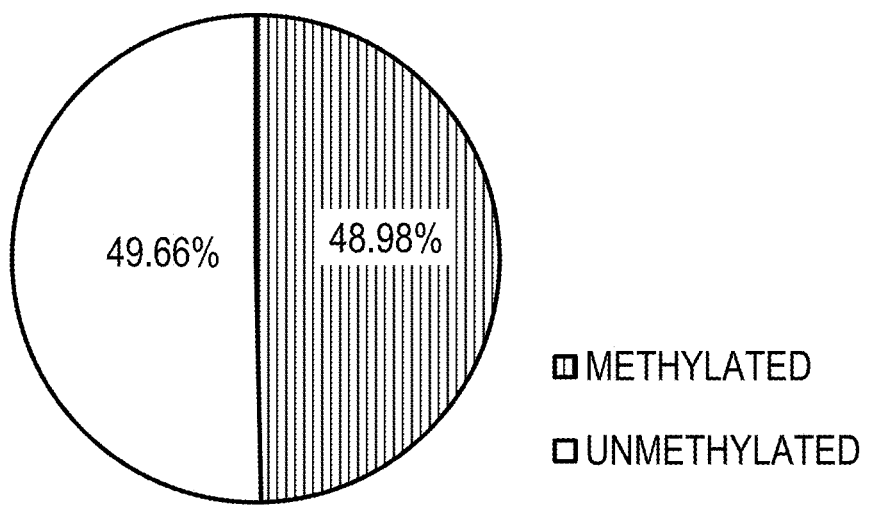
Figure 3C:
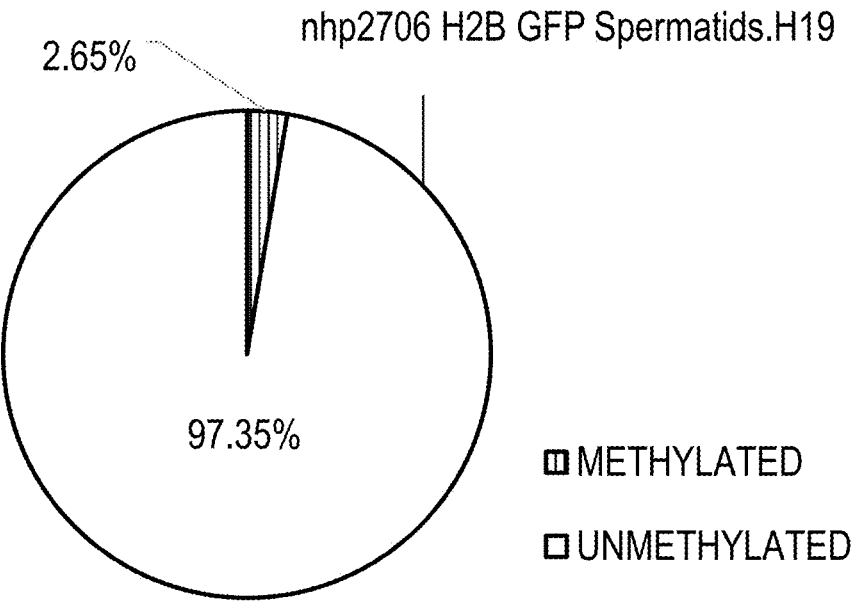
Figure 3D:
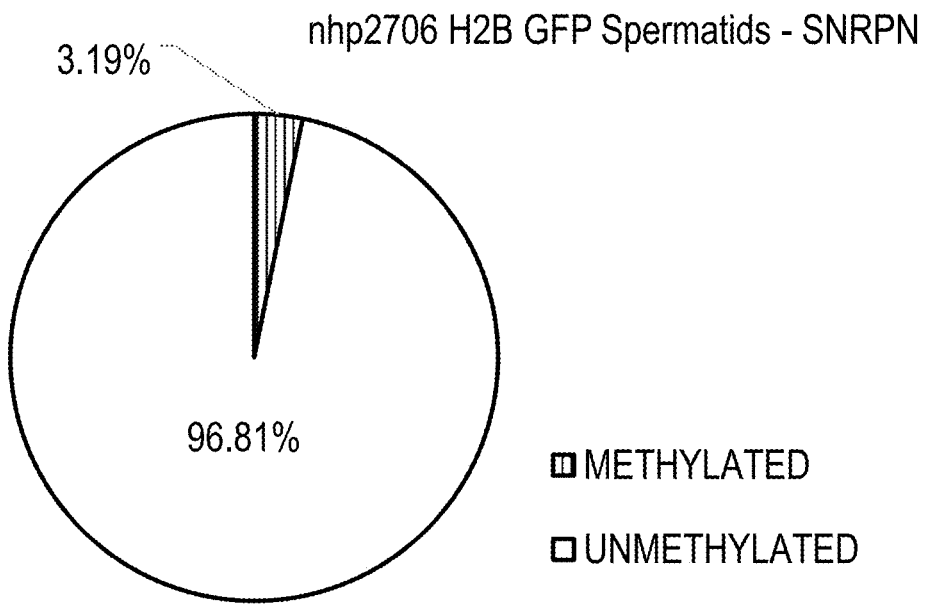

To first determine whether nhpESCs differentiate into spermatogenic cells similar to hESCs and hiPSCs, nhpESCs were first differentiated in a spermatogonial stem cell (SSC) differentiation protocol as previously described (Easley et al., *Cell Rep* 2, 440-446, doi:10.1016/j.celrep.2012.07.015 (2012), Zhao et al., *Stem Cell Reports* 10, 509-523, doi: 10.1016/j.stemcr.2018.01.001 (2018), Easley et al., *Stem Cell Res* 14, 347-355, doi:10.1016/j.scr.2015.03.002 (2015), Steves et al., *iScience* 3, 161-176, doi:10.1016/j.isci.2018.04.014 (2018), Steves et al., *Syst Biol Reprod Med* 64, 225-239, doi:10.1080/19396368.2018.1481465 (2018)). A Histone 2B-GFP nhpESC (nhpESC H2B-GFP) line was chosen for downstream analyses, but all lines tested (FIG. 2A) differentiated in spermatogonia-like cells, primary and secondary spermatocyte-like cells, and haploid spermatid-like similarly to differentiations using hESCs and hiPSCs (FIGS. 2B-2D). Moreover, haploid spermatid-like cells produced by the differentiation protocol demonstrated expression of acrosin, protamine 1, and transition protein 1 (FIG. 2C); showed morphological similarities to endogenous NHP round spermatids; and showed proper imprint establishment on two confirmed parent-of-origin imprints in NHPs (Fujimoto et al., *Mol Hum Reprod* 11, 413-422, doi:10.1093/molehr/gah180 (2005), Fujimoto et al., *Stem Cells* 24, 595-603, doi:10.1634/stemcells.2005-0301 (2006)) (FIGS. 3A-3D). Confirmation of haploidy by fluorescence in situ hybridization demonstrated that both X and Y round spermatid-like cells were produced (FIG. 2D).

Figure 4A:
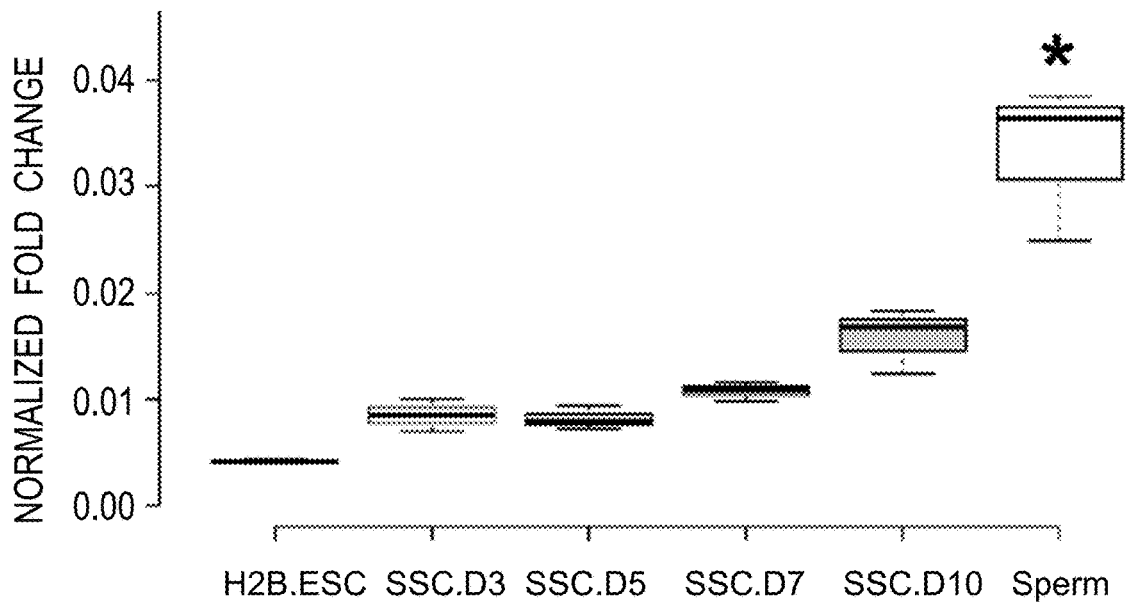
FIG. 4A is a graph illustrating the expression of Tet3 in embryonic stem cells (ESCs), differentiating sperm cells at Day 3, 5, 7 and 10 of in vitro SSC differentiation, and mature spermatozoa collected from rhesus macaque. While progressive increased expression of Tet3 was observed as ESCs differentiated to haploid spermatids on Day 10, a significantly lower expression compared to mature spermatozoa was observed. Normalized fold change ($2^{\char`\^} \delta CT$) for TET3 is shown. * $p<0.001$.
Figure 4B:
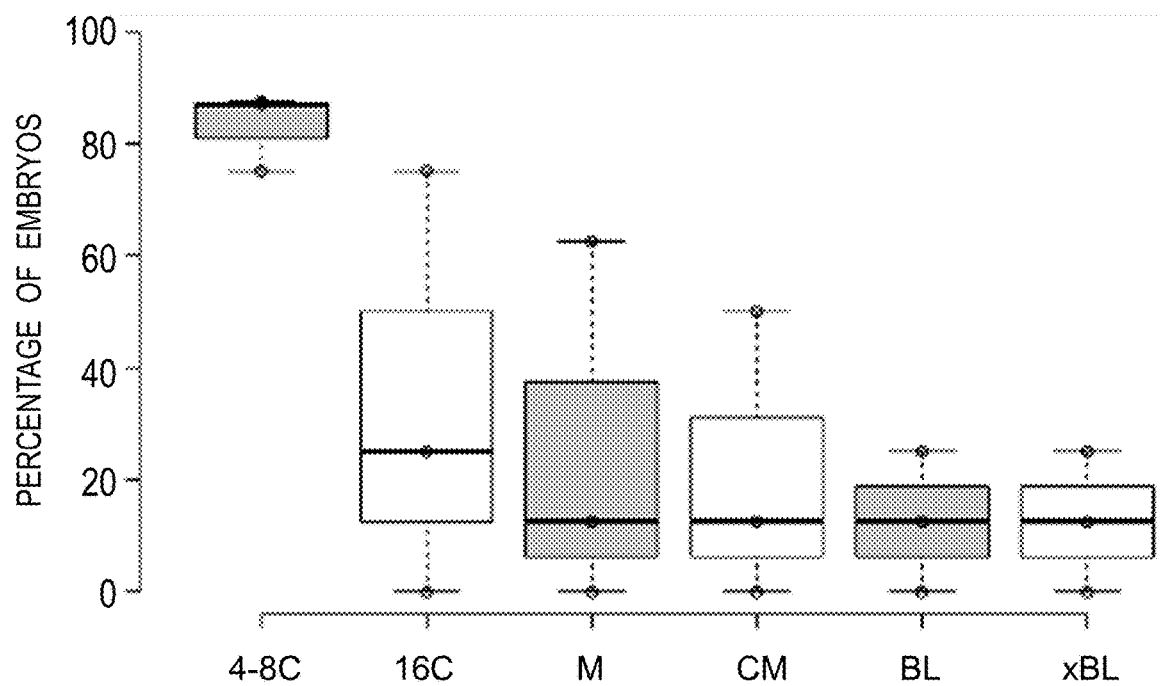
FIGS. 4B-4G are graphs of the percentage of embryos that reach each developmental/post fertilization stage including the 4-8 cell stage (4-8C), 16 cell stage (16C), morula (M), compacted morula (CM), early blastocyst (BL), and expanded blastocyst (xBL) stages when in vitro-derived round spermatid-like cells are co-injected with TET3 protein and activated by sperm cell factor (SCF) (4B), ococyte activation by DMAP/ionomycin treatment (4C), oocyte activation by sperm cell factor (SCF) (4D), SCF plus TET3 plasmid DNA (4E), SCF plus TET3 plasmid DNA plus TET3 mRNA (4F), fertilization by ICSI with rhesus sperm (4G).
Figure 4C:
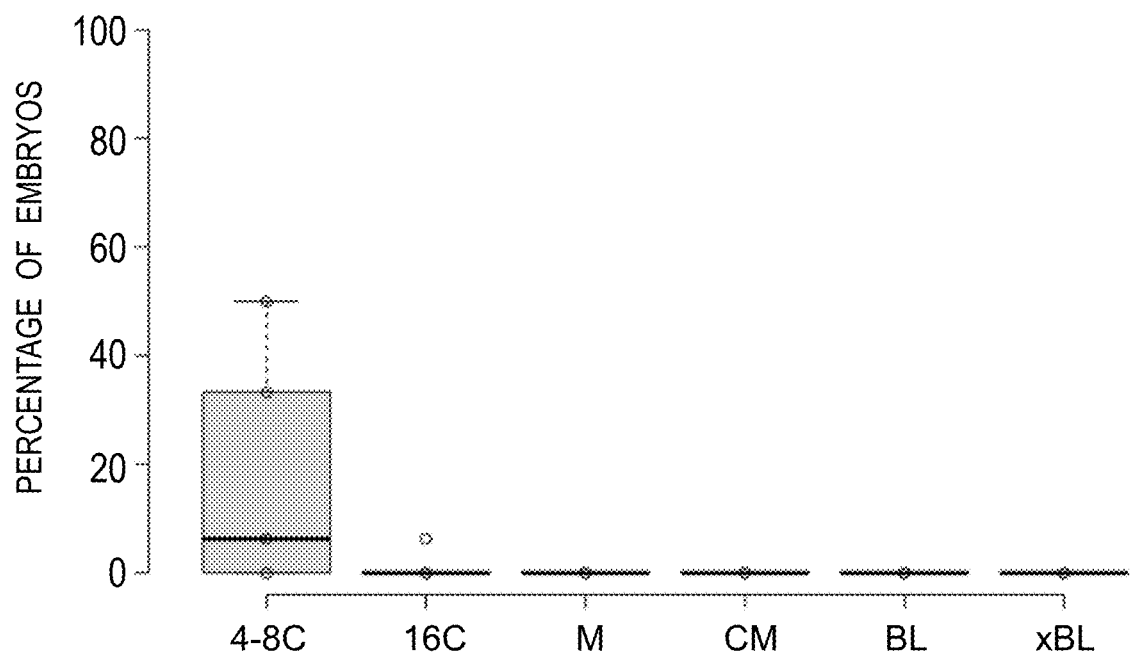
Figure 4D:
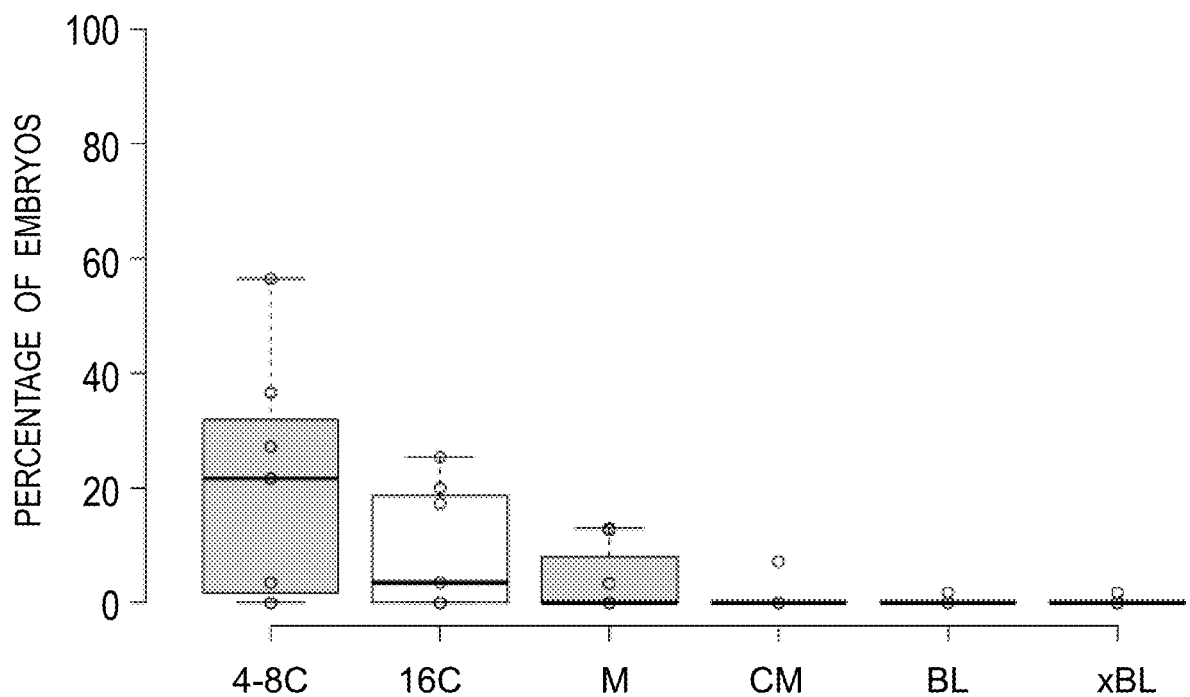
Figure 4E:
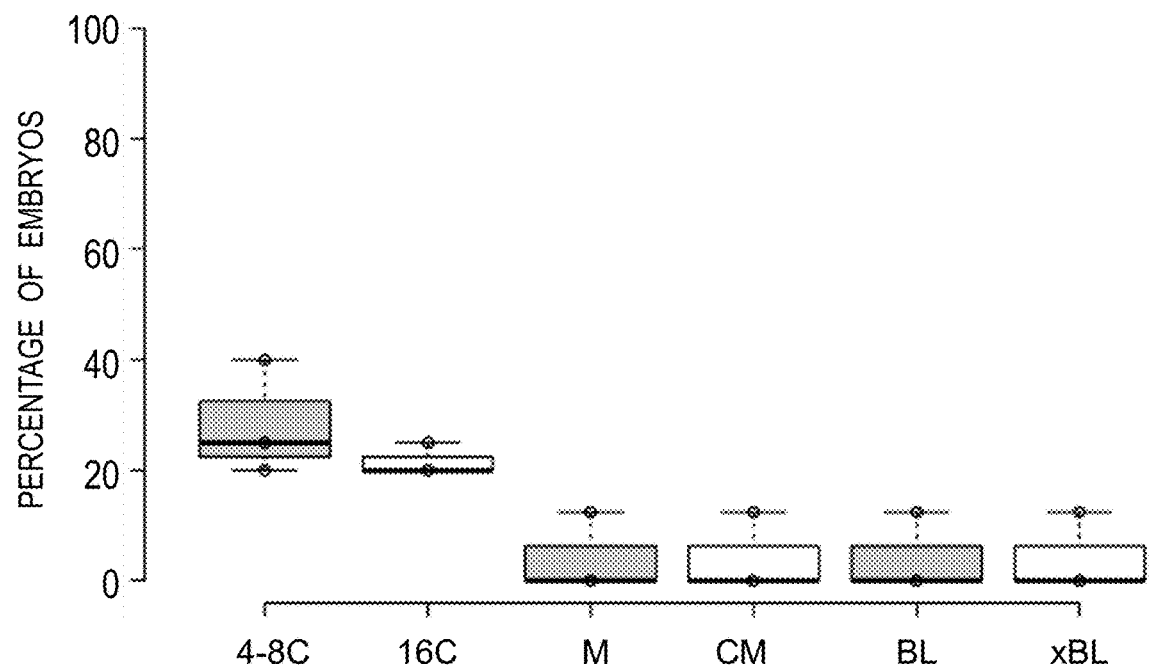
Figure 4F:
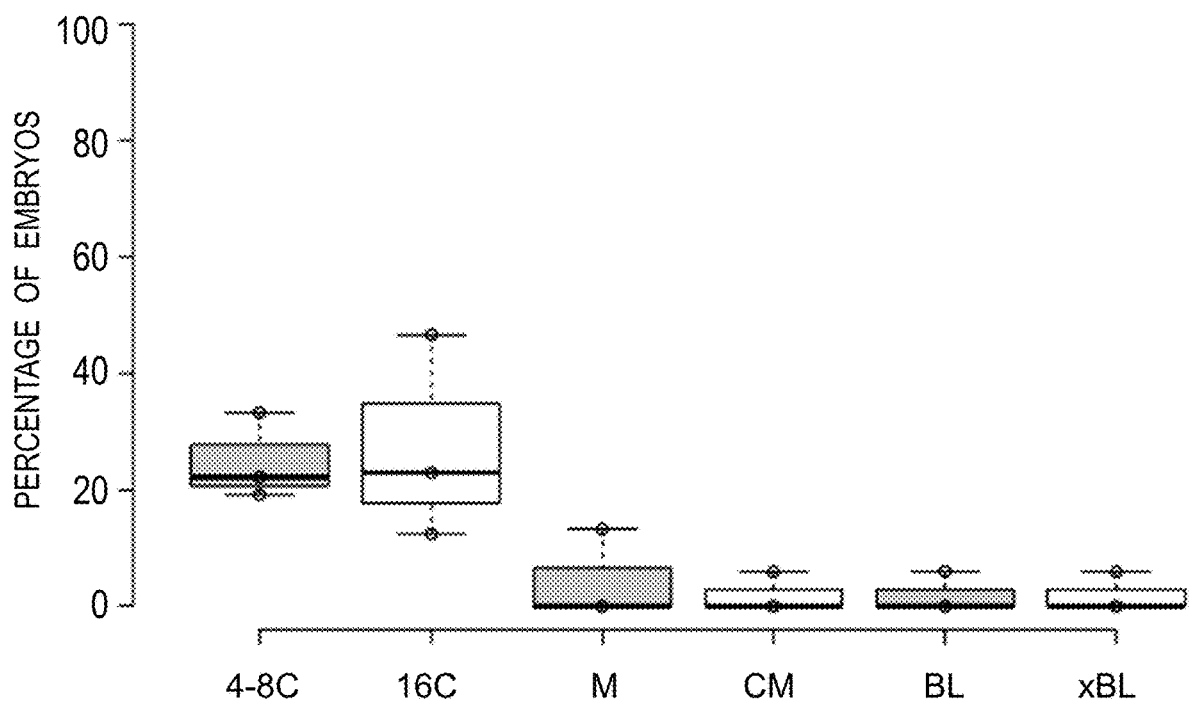
Figures 4G, 5A:
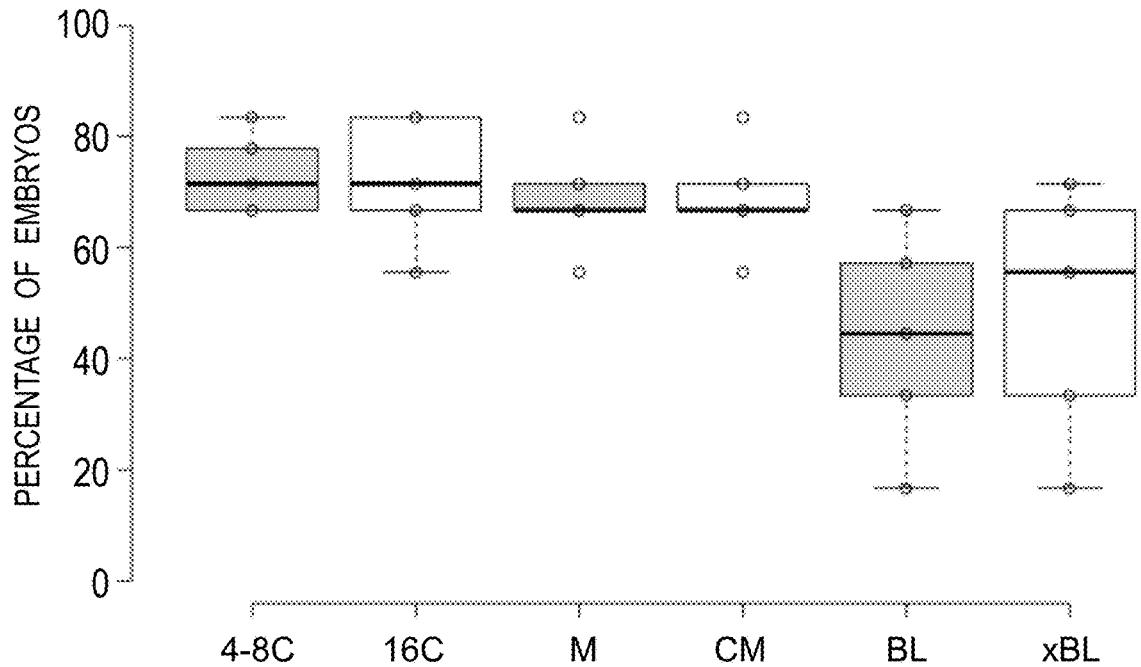
FIG. 5A is an illustration of SHANK3 target sequences (SEQ ID NOS:4 and 5) and an exemplary gRNA (SEQ ID NO:6).

Similar to hESCs and hiPSCs (Easley et al., *Cell Rep* 2, 440-446, doi:10.1016/j.celrep.2012.07.015 (2012)), nhpESC-derived spermatogenic cells, including round spermatid-like cells, exhibited many of the hallmarks of the "Gold Standards" of in vitro-derived gametes. To explore whether NHP in vitro-derived round spermatid-like cells (rSLCs) have functional gamete ability, rhesus oocytes were fertilized by intracytoplasmic sperm injection (ICSI). Like clinical ART applications using endogenous round spermatids, in vitro derived round spermatid-like cells could not activate oocytes for in vitro development, but these round spermatid-like cells did undergo DNA decondensation and pronucleus formation, generally arresting at the 4-8 cell developmental stage (FIGS. 4A and 4B). Upon oocyte activation using a crude sperm extract (Meng & Wolf, *Hum Reprod* 12, 1062-1068, doi:10.1093/humrep/12.5.1062 (1997)), ICSI of rSLCs induced further development DNA decondensation, male and female pronuclei formation, and cleavage. While most embryos arrested at the 8-16 cell stage, the stage where non-human primates undergo maternal to zygotic transcription control, some did progress to the blastocyst stage (FIGS. 4A and 4B). GFP-H2B expression in the nuclei of cells throughout the developing embryo demonstrate that the male genome from the nhpESC-derived rSLCs contributed to the developing embryo.

Example 2: Tet3 Enhances the Morphology and Development Rate of Preimplantation Embryos Materials and Methods TET3 Gene Expression and in vitro Transcription/Translation of TET3.

TET3 Gene Expression and in vitro Transcription/Translation of TET3. Full length human TET3 (FH-TET-pEF; Addgene #49446, the sequence of which is specifically incorporated by reference herein in its entirety) plasmid DNA was used to generate TET3 protein supplements for ICSI. TET3 protein was generated using the Promega TnT (Transcription and Translation) kit as per manufacturer's instructions. Following generation of TET3 protein, TET3 was immunopurifed from the reticulocyte lysate using the Dynabeads Protein A Immunoprecipitation kit (Thermofisher) per manufacturer's instructions using an immunoprecipitating-capable TET3 antibody (Abcam) with the following modification: immunoprecipitation was incubated overnight at 4° C. Following elution from Dynabeads, purified TET3 protein was diluted in ICB buffer (KCL 120 mM, HEPES 20 mM, EGTA 100 µM, Sodium glycerophosphate 10 mM; pH 7.5)36 compatible with ICSI.

TET3 RNA levels were measured in nhpESCs, Day 3, Day 5, Day 7, Day 10 differentiation cultures, and in mature wild-type sperm. RNA from all samples listed above was isolated by RNeasy RNA isolation kit (Qiagen) per manufacturer's instructions. cDNA was generated as described above using iScript Reverse Transcription Supermix for RT-qPCR (Bio-Rad) per manufacturer's instructions. 3 distinct biological replicates were used for analyses with average Normalized fold change (2^ δCT) shown. PCR primer sequences for TET3: Forward-5' CCCAAAGAG-GAAGAAGTG 3' (SEQ ID NO:14); Reverse-5' GCAGT-CAATCGCTATTTC 3' (SEQ ID NO:15).

Addgene #49446 provides a nucleic acid sequence insert:

(SEQ ID NO: 12)
```
atggactacaaggacgacgatgacaagctcgatggaggataccctacgac gtgcccgactacgccggaggactcgacagccagtttcaggtgccctggcc gtccagccggacctgccaggcctttatgacttccctcagcgccaggtgatg gtagggagcttcccggggtctgggctctccatggctgggagtgagtcccaa ctccgaggggtggagatggtcgaaagaaacggaaacggtgtggtacttgt gagccctgccggcggctggaaaactgtggcgcttgcactagctgtaccaac cgccgcacgcaccagatctgcaaactgcgaaaatgtgaggtgctgaagaaa aaagtagggcttctcaaggaggtggaaataaaggctggtgaaggagccggg ccgtggggacaaggagcggctgtcaagacaggctcagagctcagcccagtt gatggacctgttccaggtcagatggactcagggccagtgtaccatgggggac tcacggcagctaagcgcctcaggggtgccggtcaatggtgctagagagccc gctggaccccagtctgctggggactgggggtccttggcgggtagaccaaaag cccgactgggaggctgcccaggcccagctcatactgctcgcctggaagat gcccacgatctggtggccttttcggctgtggccgaagctgtgtcctcttat ggggcccttagcacccggctctatgaaaccttcaaccgtgagatgagtcgt gaggctgggaacaacagcaggggaccccggccagggcctgagggctgctct gctggcagcgaagaccttgacacactgcagacggccctggccctcgcgcgg catggtatgaaaccacccaactgcaactgcgatggcccagaatgccctgac tacctcgagtggctggaggggaagatcaagtctgtggtcatggaaggaggg gaggagcggcccaggctcccagggcctctgcctcctggtgaggccggcctc ccagcaccaagcaccaggccactcctcagctcagaggtgcccagatctct ccccaagagggcctgcccctgtcccagagtgccctgagcattgccaaggaa aaaaacatcagcttgcagaccgccattgccattgaggccctcacacagctc tcctctgccctcccgcagccttctcattccaccccccaggcttcttgcccc cttcctgaggccttgtcacctcctgccccctttcagatctccccagtcttac ctccgggctccctcatggcctgtggttcctcctgaagagcactcatctttt gctcctgatagctctgccttccctccagcaactcctagaactgagttccct gaagctggggcactgacacccctccagcaacgccccggagctcctggccc atgcctcgcccaagccccgatccatggctgaactggagcagttgttgggc agcgccagtgattacatccagtcagtattcaagcggcctgaggccctgcct accaagcccaaggtcaaggtggaggcaccctcttcctccccggcccggcc ccatcccctgtacttcagagggaggctcccacgccatcctcggagcccgac acccaccagaaggcccagaccgccctgcagcagcacctccaccacaagcgc agcctcttcctagaacaggtgcacgacacctccttccctgctccttcagag ccttctgctcctggctggtggcccccaccaagttcacctgtcccacggctt ccagacagaccacccaaggagaagaagaagctcccaacaccagctgga ggtcccgtgggaacggagaaagctgccctgggatcaagcccagtgtccga aagcccattcagatcaagaagtccaggccccgggaagcacagccctcttc ccacctgtccgacagattgtcctggaagggcttaggtccccagcctcccag
```

-continued

```
gaagtgcaggctcatccaccggcccctctgcctgcctcacagggctctgct
gtgcccctgccccagaaccttctcttgcgctatttgcacctagtccctcc
agggacagcctgctgcccctactcaggaaatgaggtccccagcccatg
acagccttgcagccaggctccactggccctcttcccctgccgatgacaag
ctggaagagctcatccggcagtttgaggctgaatttggagatagctttggg
cttcccggcccccttctgtgcccattcaggaccccgagaaccagcaaaca
tgtctcccagccctgagagccctttgctacccgttcccccaagcaaatc
aagattgagtcttcgggggctgtgactgtgctctcaaccacctgcttccat
tcagaggaggaggacaggaggccacacccaccaaggctgagaacccactc
acacccaccctcagtggcttcttggagtcacctcttaagtacctggacaca
cccaccaagagtctgctggacacacctgccaagagagcccaggccgagttc
cccacctgcgattgcgtcgaacaaatagtggagaaagatgaaggtccatat
tatactcacttgggatctggcccacggtcgcctctatccgggaactcatg
gaggagcggtatggagagaaggggaaagccatccggatcgagaaggtcatc
tacacggggaaggagggaaagagctcccgcggttgccccattgcaaagtgg
gtgatccgcaggcacacgctggaggagaagctactctgcctggtgcggcac
cgggcaggccaccactgccagaacgctgtgatcgtcatcctcatcctggcc
tgggagggcattccccgtagcctcggagacaccctctaccaggagctcacc
gacaccctccggaagtatgggaaccccaccagccggagatgcggcctcaac
gatgaccggacctcgcgcttgccaaggcaaagaccccaacacctgtggtgcc
tccttctcctttggttgttcctggagcatgtacttcaacggctgcaagtat
gctcggagcaagacacctcgcaagttccgcctcgcagggacaatcccaaa
gaggaagaagtgctccggaagagtttccaggacctggccaccgaagtcgct
cccctgtacaagcgactggcccctcaggcctatcagaaccaggtgaccaac
gaggaaatagcgattgactgccgtctggggctgaaggaaggacgccccttc
gcgggggtcacggcctgcatggacttctgtgcccacgcccacaaggaccag
cataacctctacaatgggtgcaccgtggtctgcaccctgaccaaggaagac
aatcgctgcgtgggcaagattcccgaggatgagcagctgcatgttctcccc
ctgtacaagatggccaacacggatgagtttggtagcgaggagaaccagaat
gcaaaggtgggcagcggagccatccaggtgctcaccgccttcccccgcgag
gtccgacgcctgcccgagcctgccaagtcctgccgccagcggcagctggaa
gccagaaaggcagcagccgagaagaagaagattcagaaggagaagctgagc
actccggagaagatcaagcaggaggccctggagctggcgggcattacgtcg
gacccaggcctgtctctgaagggtggattgtcccagcaaggcctgaagccc
tccctcaaggtggagccgcagaaccacttcagctccttcaagtacagcggc
aacgcggtggtggagagctactcggtgctgggcaactgccggccctccgac
ccttacagcatgaacagcgtgtactcctaccactcctactatgcacagccc
agcctgacctccgtcaatgcttccactccaagtacgctctcccgtctttt
agctactatggcttccatccagcaacccgtcttcccctctcagttcctg
ggtcctggtgcctgggggcatagtggcagcagtggcagttttgagaagaag
```

-continued

```
ccagacctccacgctctgcacaacagcctgagcccggcctacggtggtgct
gagtttgccgagctgcccagccaggctgttcccacagacgccaccacccc
actcctcaccaccagcagcctgcgtacccaggccccaaggagtatctgctt
cccaaggcccccctactccactcagtgtccagggaccctccccccttgcc
cagagctccaactgctacaacagatccatcaagaagagccagtagacccg
ctgacccaggctgagcctgtgcccagagacgctggcaagatgggcaagaca
cctctgtccgaggtgtctcagaatggaggacccagtcacctttggggacag
tactcaggaggcccaagcatgtcccccaagaggactaacggtgtgggtggc
agctgggggtgtgttctcgtctggggagagtcctgccatcgtccctgacaag
ctcagttcctttggggccagctgcctggccccttcccacttcacagatggc
cagtgggggctgttccccggtgaggggcagcaggcagcttcccactctgga
ggacggctgcgaggcaaaccgtggagcccctgcaagtttgggaacagcacc
tcggccttggctgggcccagcctgactgagaagccgtgggcgctgggggca
ggggatttcaactcggccctgaaaggtagtcctgggttccaagacaagctg
tggaaccccatgaaaggagaggagggcaggattccagccgcaggggccagc
cagctggacagggcctggcagtcctttggtctgcccctgggatccagcgag
aagctgtttggggctctgaagtcagaggagaagctgtggaccccttcagc
ctggaggaggggccggctgaggagcccccagcaagggagcggtgaaggag
gagaagggcggtggtggtgcggaggaggaagaggaggagctgtggtcggac
agtgaacacaacttcctggacgagaacatcggcggcgtggccgtggcccca
gcccacggctccatcctcatcgagtgtgcccggcgggagctgcacgccacc
acgccgcttaagaagcccaaccgctgccaccccacccgcatctcgctggtc
ttctaccagcacaagaacctcaaccagcccaaccacgggctggccctctgg
gaagccaagatgaagcagctggcggagagggcacgggcacggcaggaggag
gctgcccggctgggcctgggccagcaggaggccaagctctacgggaagaag
cgcaagtgggggggcactgtggttgctgagccccagcagaaagagaagaag
ggggtcgtccccacccggcaggcactggctgtgcccacagactcggcggtc
accgtgtcctcctatgcctacacgaaggtcactggcccctacagccgctgg
atctagtctaga
```

SEQ ID NO:12 encodes the open reading frame:

(SEQ ID NO: 13)
MDYKDDDDKLDGGYPYDVPDYAGGLDSQFQVPLAVQPDLPGLYDFPQRQVM
VGSFPGSGLSMAGSESQLRGGGDGRKKRKRCGTCEPCRRLENCGACTSCTN
RRTHQICKLRKCEVLKKKVGLLKEVEIKAGEGAGPWGQAAVKTGSELSPV
DGPVPGQMDSGPVYHGDSRQLSASGVPVNGAREPAGPSLLGTGGPWRVDQK
PDWEAAPGPAHTARLEDAHDLVAFSAVAEAVSSYGALSTRLYETFNREMSR
EAGNNSRGPRPGPEGCSAGSEDLDTLQTALALARHGMKPPNCNCDGPECPD
YLEWLEGKIKSVVMEGGEERPRLPGPLPPGEAGLPAPSTRPLLSSEVPQIS
PQEGLPLSQSALSIAKEKNISLQTAIAIEALTQLSSALPQPSHSTPQASCP
LPEALSPPAPFRSPQSYLRAPSWPVVPPEEHSSFAPDSSAFPPATPRTEFP

```
EAWGTDTPPATPRSSWPMPRPSPDPMAELEQLLGSASDYIQSVFKRPEALP

TKPKVKVEAPSSSPAPAPSPVLQREAPTPSSEPDTHQKAQTALQQHLHHKR

SLFLEQVHDTSFPAPSEPSAPGWWPPPSSPVPRLPDRPPKEKKKKLPTPAG

GPVGTEKAAPGIKPSVRKPIQIKKSRPREAQPLFPPVRQIVLEGLRSPASQ

EVQAHPPAPLPASQGSAVPLPPEPSLALFAPSPSRDSLLPPTQEMRSPSPM

TALQPGSTGPLPPADDKLEELIRQFEAEFGDSFGLPGPPSVPIQDPENQQT

CLPAPESPFATRSPKQIKIESSGAVTVLSTTCFHSEEGGQEATPTKAENPL

TPTLSGFLESPLKYLDTPTKSLLDTPAKRAQAEFPTCDCVEQIVEKDEGPY

YTHLGSGPTVASIRELMEERYGEKGKAIRIEKVIYTGKEGKSSRGCPIAKW

VIRRHTLEEKLLCLVRHRAGHHCQNAVIVILILAWEGIPRSLGDTLYQELT

DTLRKYGNPTSRRCGLNDDRTCACQGKDPNTCGASFSFGCSWSMYFNGCKY

ARSKTPRKFRLAGDNPKEEEVLRKSFQDLATEVAPLYKRLAPQAYQNQVTN

EEIAIDCRLGLKEGRPFAGVTACMDFCAHAHKDQHNLYNGCTVVCTLTKED

NRCVGKIPEDEQLHVLPLYKMANTDEFGSEENQNAKVGSGAIQVLTAFPRE

VRRLPEPAKSCRQRQLEARKAAAEKKKIQKEKLSTPEKIKQEALELAGITS

DPGLSLKGGLSQQGLKPSLKVEPQNHFSSFKYSGNAVVESYSVLGNCRPSD

PYSMNSVYSYHSYYAQPSLTSVNGFHSKYALPSFSYYGFPSSNPVFPSQFL

GPGAWGHSGSSGSFEKKPDLHALHNSLSPAYGGAEFAELPSQAVPTDAHHP

TPHHQQPAYPGPKEYLLPKAPLLHSVSRDPSPFAQSSNCYNRSIKQEPVDP

LTQAEPVPRDAGKMGKTPLSEVSQNGGPSHLWGQYSGGPSMSPKRTNGVGG

SWGVFSSGESPAIVPDKLSSFGASCLAPSHFTDGQWGLFPGEGQQAASHSG

GRLRGKPWSPCKFGNSTSALAGPSLTEKPWALGAGDFNSALKGSPGFQDKL

WNPMKGEEGRIPAAGASQLDRAWQSFGLPLGSSEKLFGALKSEEKLWDPFS

LEEGPAEEPPSKGAVKEEKGGGGAEEEEEELWSDSEHNFLDENIGGVAVAP

AHGSILIECARRELHATTPLKKPNRCHPTRISLVFYQHKNLNQPNHGLALW

EAKMKQLAERARARQEEAARLGLGQQEAKLYGKKRKWGGTVVAEPQQKEKK

GVVPTRQALAVPTDSAVTVSSYAYTKVTGPYSRWI
```

Embryo Development Assessments.

Fertilized embryos were cultured in HECM-9 media (Arthur Chang & Chan, *Methods Mol Biol,* 770, 337-363, doi:10.1007/978-1-61779-210-6_13 (2011)) and were monitored daily until Day 7-8 when blastocysts were formed. To minimize the exposure of fluorescent light that might affect embryo development, selected embryos were used for fluorescent imaging. Embryo development rates were calculated based on fertilized embryos that had achieved the first division, 4-8 cells, 16 cells, morula, compacted morula, blastocyst, and expanded blastocyst stages.

Intracytoplasmic Spermatid Injection (ICSI) of Spermatids, Sperm Extract and Tet3 into Mature Rhesus Macaque Oocyte.

Sperm extract and Tet3 protein can be mixed while spermatids are prepared in a separate microdrop in a petri-dish covered with sterile mineral oil. MII mature rhesus oocytes can be placed in a separate drop on the same petri-dish. For ICSI, a micropipette mounted onto a micromanipulator and connected with a microinjector can be used to aspirate spermatids followed by the aspiration of Tet3 and sperm extract. The mixture of spermatids, Tet3 and sperm extract can then be injected into the cytoplasm of each oocyte. Following ICSI, oocytes can be activated by culturing five minutes in 5 μM ionomycin in TALP-Hepes medium, followed by incubation in 2 mM 6-Dimethylaminopurine (6-DMAP) in HECM-9 for five hours in a humidified atmosphere of 5% $CO_2$, 5% $O_2$ and 90% $N_2$ at 37° C.

In-Vitro Culture of NHP Embryo.

Oocytes are washed in equilibrated TALP and returned to culture in 100 μl HECM-9, monkey embryo culture medium, under oil. Fertilization is assessed within 3-6 h by detection of the second polar body using Hoffmann Modulation Contrast optics. The number of pronuclei is assessed between 12-16 h post injection. After completion of the second cleavage division, 4-8 cell embryos are co-cultured in HECM-9+10% FCS Preparation of Monkey Sperm Extract.
1. Ejaculated sperm is washed with TH3 medium by centrifugation at 1500 rpm for 5 min. The supernatant is aspirated out the supernatant and the sperm concentration adjusted to 5-10×10^8 sperm/mL.
2. Sperm layer is then be pelleted and washed three times with modified intracellular buffer (ICB) by centrifugation at 1,400 rpm (Eppendorf benchtop centrifuge) for 5 min at RT.
3. This is followed by Lysing by four freeze-thaw cycles.
4. The lysed samples are then be spin at 100,000×g (e.g. 48,000 rpm of Beckman micro-ultracentrifuge) for 1 hour at 4 C.
5. The supernatant is transferred to new clean Eppendorf tube, and kept on ice.
6. It is then concentrated (~3-5 folds) by using centrocon-30 microfiltration membrane (Amicon Cat #4208) and centrifugation at 3000×g for 20 min.
7. Aliquoted 10 uL per vial and stored at −80° C.

ICB buffer (pH 7.5) is shown in Table 2 (above).

Results

Most of the embryos arrested at the 8-16 cell stage when the embryonic genome engages. TET3 expression (ten-eleven translocation 3) was examined. TET3 is an enzyme responsible for DNA demethylation, which is an important step in early fertilization (Guo et al., *Cell Stem Cell* 15, 447-459, doi:10.1016/j.stem.2014.08.003 (2014), Navara et al., *Stem Cells* 25, 2695-2704, doi:2007-0286 [pii]10.1634/stemcells.2007-0286 (2007)).

Experiments were designed to determine if Tet3 is responsible for prompt erasure of methylated marks shortly after injection of the spermatids. Like endogenous round spermatids, and unlike mature sperm, in vitro-derived rSLCs show reduced TET3 expression (FIG. 4A). Addition of purified TET3 protein and trichostatin A (TSA) at the time of rSLC injection resulted in improved fertilization rates, higher quality of embryos based on improved embryo morphology (i.e. low fragmentation), and improved development rates (e.g., elevated blastocyst rates) compared to TET3 cDNA+TSA, TET3 cDNA+mRNA+TSA, or oocyte activation alone (FIG. 4B-4H).

Figure 4H:
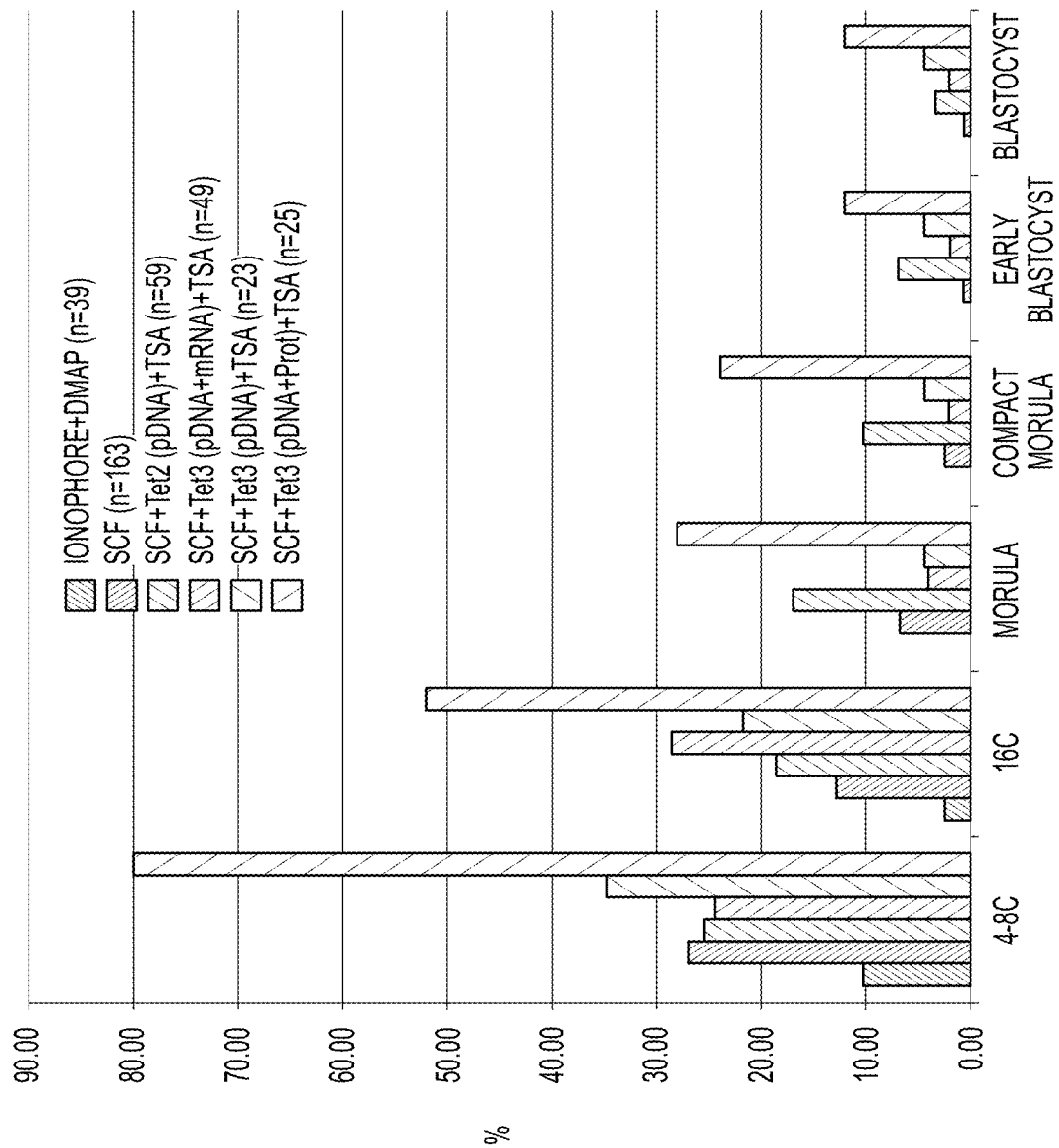
FIG. 4H is a bar graph showing the effect of various factors on in vitro procreated embryo development. Each cluster of bars (e.g., 4-8 cell, 16 cell, morula, compact morula, early blastocyst, blastocyst) represents, from left-to-right: ionophore+DMAP, SCF, SCF+Tet2 (pDNA)+TSA, SCF+Tet3 (pDNA+mRNA)+TSA, SCF+Tet3 (pDNA)+TSA, and SCF+Tet3 (pDNA+Protein)+TSA.

Co-injection of sperm extract and in vitro derived spermatids with Tet3 plasmid DNA (Tet3-pDNA), Tet3 mRNA, or Tet3 protein indicated the importance on timing of Tet3 activity or paternal demethylation during ZGA and subsequent EGA events (FIGS. 4A-4H). Compared to injecting sperm extract alone, co-injection of Tet3-pDNA improved cleavage rate while co-injection with Tet3-mRNA further improve development up to 8 cell stage with development to 16 cell stage and morula at low rate. Co-injection with Tet3 protein significantly improved cleavage rate with majority of embryo develop beyond 8-cell stage and close to 12% reached to blastocyst stage (FIG. 4H).

In addition, morphology and development rate of preimplantation embryos in Tet3 protein group was comparable to normal embryos fertilized with ejaculated spermatozoa, while high level of fragmentation was observed in all other treatment groups which indicates abnormal development in such embryos (see, e.g., Stone et al., *Am J Obstet Gynecol.,* 192(6):2014-9 (2005)). Although fragmentation is commonly seen in natural conception, the degree of fragmentation was also used as guideline for determining embryo quality and predictor of pregnancy (Stone et al., 2005).

These experiments are believed to represent the first report to generate functional male gametes from non-human primate pluripotent stem cells. While complete in vitro spermatogenesis resulting in mature spermatozoa has not been accomplished in any species, these results are the first to show that functional haploid spermatids can be generated completely in vitro. Spermatids derived from the protocol are immature and not capable of activating oocytes on their own. However, the addition of activation factors coupled with TET3 augmentation (e.g., purified TET3 protein) increased the efficiency of generating healthy embryos. These results support feasibility of regenerative medicine-based therapies whereby patient-specific pluripotent stem cells are differentiated into functional gametes for patients unable to produce their own gametes, particularly where such gametes are needed for managing their infertility through ART.

Example 3: CRISPR/Cas9 Efficiently and Specifically Modifies a Target Gene in Pre-Implantation Embryos In Vitro Materials and Methods Gene targeting will be achieved in pluripotent stem cells or skin fibroblast followed by reprogramming to pluripotent state or induced pluripotent stem cells (iPSCs). In brief, gRNA that target a specific target gene will be transfected into aforementioned cell types either in the form of RNA or plasmid DNA that express the gRNA. Cas9 mRNA or protein or expression vector that express Cas9 will be co-transfected with gRNA into aforementioned cell types. Successful targeting will be confirmed in clonal cell line by sequencing and identified for in vitro production of haploid spermatids for fertilization. To further confirm on- and off-target effect, whole genome sequencing can be performed on the selected cell lines prior to the derivation of haploid spermatids for fertilization, embryo production or production of offspring.

Intracytoplasmic Spermatid Injection (ICSI) of Spermatids, Sperm Extract and Tet3 into Mature Rhesus Macaque Oocyte:

Sperm extract and Tet3 protein will be mixed while spermatids will be prepared in a separate microdrop in a petri-dish covered with sterile mineral oil. MII mature rhesus oocytes will be placed in a separate drop on the same petri-dish. For ICSI, a micropipette mounted onto a micromanipulator and connected with a microinjector will be used to aspirate spermatids followed by the aspiration of Tet3 and sperm extract. The mixture of spermatids, Tet3 and sperm extract will then be injected into the cytoplasm of each oocyte. Following ICSI, oocytes will then be activated by culturing five minutes in 5 µM ionomycin in TALP-Hepes medium, followed by incubation in 2 mM 6-Dimethylaminopurine (6-DMAP) in HECM-9 for five hours in a humidified atmosphere of 5% $CO_2$, 5% $O_2$ and 90% $N_2$ at 37° C.

In-vitro Culture of NHP Embryo:

Oocytes are washed in equilibrated TALP and returned to culture in 100 µl HECM-9, monkey embryo culture medium, under oil. Fertilization is assessed within 3-6 h by detection of the second polar body using Hoffmann Modulation Contrast optics. The number of pronuclei is assessed between 12-16 h post injection. After completion of the second cleavage division, 4-8 cell embryos are co-cultured in HECM-9+10% FCS (Hyclone Laboratories, Inc., Logan, UT).

Results

All gene targeted embryos generated from gene targeted pluripotent stem cells derived spermatids are expected to carry the same genetic modification. If the gene target is genetic mutation linked to inherited genetic disease such as Huntington's disease, genetically corrected embryos can be generated with no off-target effect.

There are currently no cures for Autistic Spectrum Disorders (ASD), and treatments are only available for particular symptoms pertaining to a child's development. It is a devastating disorder that has significant social and economic impact as the number of children affected increases. An estimated lifetime cost for an individual with an ASD is $3.2 million, which is largely attributable to loss of productivity and the cost of adult care. The diagnosis of ASD is primarily based on deficits in all of the following: reciprocal social interaction, communication and stereotyped behaviors. In populations of diagnosed children, 15-70% exhibit intellectual impairments. The fundamental diagnosis for ASD is homogeneous, based on the criteria listed above; however, ASD can also co-exist in patients with syndromes such as Fragile X or neurofibromatosis.

Genetic studies of ASD have yielded an intriguing list of select genomic targets with several of the genes directly linked to the regulation of critical synaptic functions, including FMR1, MECP2, PTEN, UBE3A, NLGN1-NLGN4, NRXN1 and SHANK3. Moreover, some of the candidates, such as SHANK3, are associated to ASD in a gene-dosage-dependent manner SHANK3, a gene integral to the glutamatergic pathway, is a binding partner for the neuroligins NLGN3 and NLGN4, which themselves bind neurexins, all of which are genetically associated with ASD progression. Additionally, mutations in genes downstream of SHANK3 signaling, such as DIAPH3, have also been linked to ASD. Consequently, disruption of SHANK3-mediated glutamatergic transmission appears to play a pivotal role in ASD pathogenesis. Moreover, the chromosomal location of SHANK3 at 22q13 is linked to considerable human pathology due to genetic deletions which result in SHANK3 haploinsufficiency and strong phenotypes of developmental and language delays. Because of the dose dependent nature (or haploinsufficiency) of SHANK3, it is an ideal target to test CRISPR/Cas as means for inducing genetic changes in pre-implantation embryos.

Figures 5B, 5C:
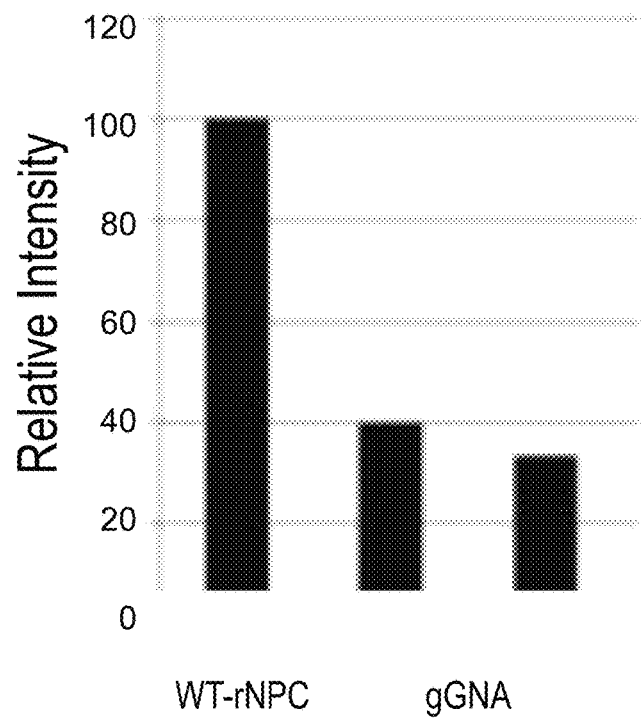
FIG. 5B is a bar graph illustrating the results of Western blot analysis of SHANK3 protein.
FIG. 5C is an illustration of the sequence of mutant cells showing deletion at the target site (SEQ ID NO:8) relative to wildtype (SEQ ID NO:7).

First, an in vitro approach was used to evaluate targeting efficiency and specificity of the SHANK3-gRNA/Cas9 systems in rhesus neural progenitor cells (NPCs). The SHANK3-gRNA-Cas9 plasmid (FIG. 5A) was transfected into NPCs and was recovered at 72 hours post-transfection for western blot (FIG. 5B) and sequence analyses (FIG. 5C). SHANK3-gRNA can effectively reduce the expression of SHANK3 in rhesus NPCs with at least 60% reduction to close to 70% loss of SHANK3 protein which was determined by using SHANK3 specific antibody in western blot analysis. This result indicates the SHANK3 gene was successfully targeted by SHANK3-gRNA, and SHANK3 protein was significantly reduced.

Figure 6B:
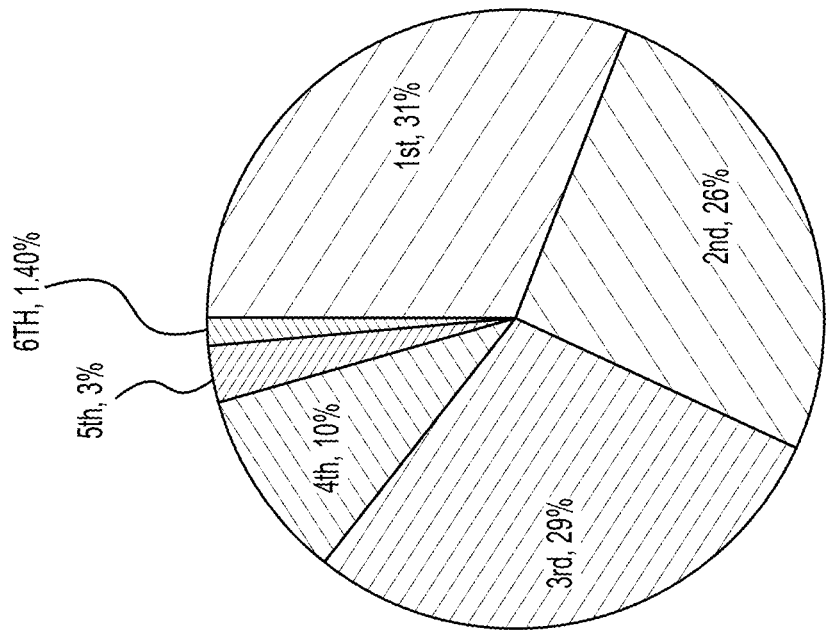
FIGS. 6A and 6B are pie charts showing sequencing analysis of gene targeted embryo and estimated timing of mutation at 1st to 6th cell division after fertilization.
Figure 6A:
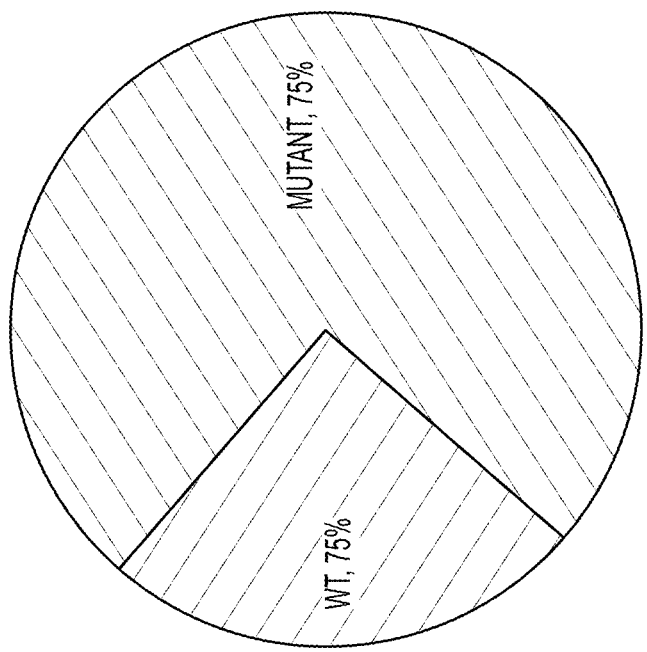

To evaluate targeting efficiency of SHANK3-gRNA in rhesus macaque pre-implantation embryos, rhesus one-cell embryos (zygotes) were co-injected with both SHANK3-gRNA and Cas9 mRNA into the cytoplasm followed by in vitro culture. A total of 96 pre-implantation embryos were analyzed for indel mutations by Genescan analysis. Earlier embryos (1-2 cell stages) were analyzed up to later stages (blastocyst) to determine gene targeting rate and time (FIG. 6A-6B). Among a total of 96 embryos screened, 72 embryos had a mutation (75%) (FIG. 6A).

CRISP-ID and TIDE were used to decompose the sequencing data and delineate the timing of when mutation might have occurred. The timing of the mutation was deduced based on the percentage of the WT-allele in the sequencing data: 0-50% (1st cell division), 51-75% (2nd cell division), 76-87.5% ($3^{rd}$ cell division), 88.5-93.75% ($4^{th}$ cell division), 94.75-96.875% ($5^{th}$ cell division), and >97.875% ($6^{th}$ cell division). Among 72 embryos with mutant allele, 31% had mutation occurring at the $1^{st}$ cell division, 26% at the $2^{nd}$ cell division, 29% at the $3^{rd}$ cell division, 10% at the $4^{th}$ cell division, 3% at the $5^{th}$ cell division and 1.4% at the $6^{th}$ cell division or later (FIG. 6B).

Figure 7:
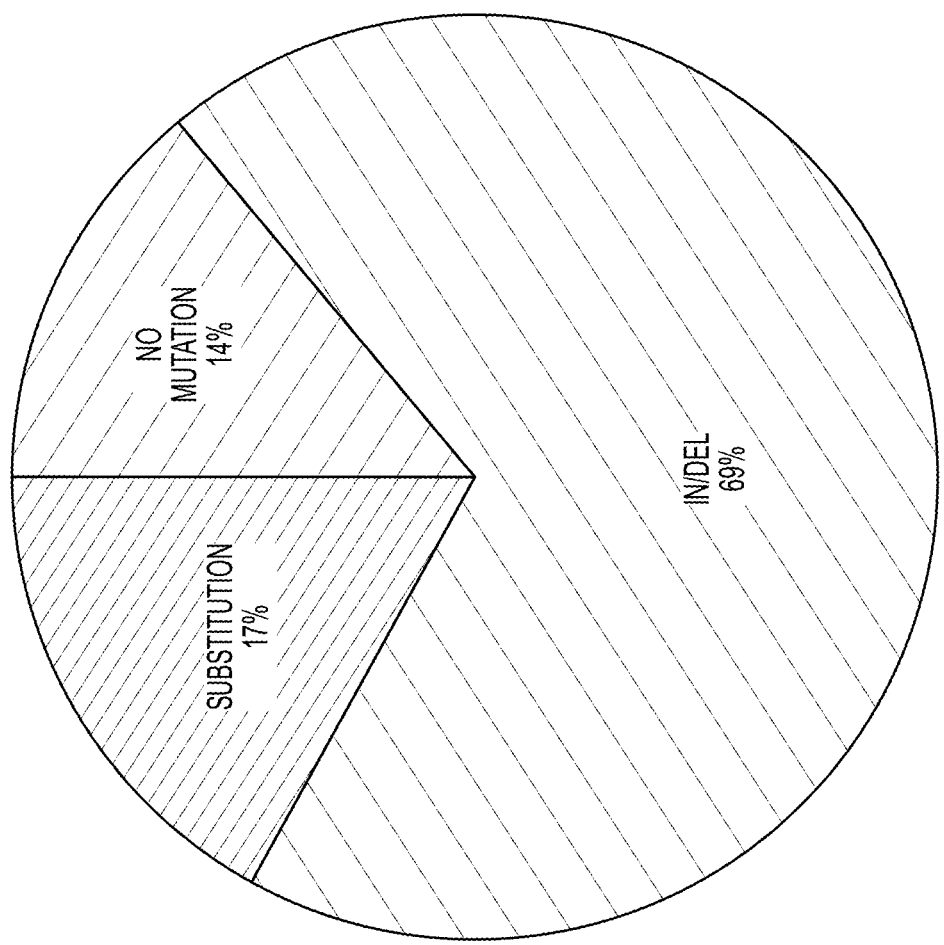
FIG. 7 is a pie chart showing the break down of types of mutations (substitutions, insertion/deletions, or no mutation) that occurred by SHANK3 CRISPR-Cas9-mediated gene editing. n=96.

As CRISPR-Cas9 induces double strand break (DSB), the main mode of mutation is through non-homologous end joining (NHEJ). NHEJ typically introduces insertions/deletions (InDels) to the sequences. The most common mutation was In/Dels (69%) (FIG. 7). Also, imperfect repair can introduce base-pair substitutions, and 17% substitutions were found in this data (FIG. 7).

Collectively, these results show that that SHANK3 can be successfully targeted in rhesus embryo using CRISPR/Cas9 efficiently and with no significant impact on early embryo development compared to WT-embryo control.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of improving embryo development comprising administering into an oocyte or male gamete, or a fertilized embryo an effective amount of a compound that increases bioavailability of a TET protein and a sperm extract to improve development of the fertilized embryo, or a subsequent embryo resulting from fertilization of the oocyte by the male gamete.

2. The method of claim 1, wherein the method comprises administering the compound that increases bioavailability of a TET protein and the sperm extract into an oocyte, and wherein the compound and the sperm extract are administered into the oocyte before, during, or after fertilization.

3. The method of claim 1, wherein the compound and the sperm extract are administered by injection.

4. The method of claim 1, wherein the compound and the sperm extract are administered by intracytoplasmic injection.

5. The method of claim 4, wherein the compound, the sperm extract, and the male gamete are administered into an oocyte in combination by intracytoplasmic sperm injection (ICSI).

6. The method of claim 1, wherein the TET protein is TET1, TET2, TET3, or a combination thereof.

7. The method of claim 1, wherein the compound is a small molecule, a TET polypeptide or protein, a fusion protein including a TET polypeptide or protein, an isolated nucleic acid encoding a TET polypeptide or protein or TET fusion protein, or an agent that increases endogenous expression of a TET polypeptide or protein.

8. The method of claim 7, wherein the compound increases bioavailability of TET3.

9. The method of claim 8, wherein the compound is a TET3 polypeptide or protein, a fusion protein including a TET3 polypeptide or protein, an isolated nucleic acid encoding a TET3 polypeptide or protein or TET3 fusion protein, or an agent that increases endogenous expression of a TET3 polypeptide or protein.

10. The method of claim 9, wherein the TET3 polypeptide or protein is full-length TET3.

11. The method of claim 9, wherein the TET3 polypeptide or protein is human TET3 or a variant thereof comprising at least 85% sequence identity to human TET3.

12. The method of claim 1, wherein the method comprises administering the compound that increases bioavailability of a TET protein and the sperm extract into a male gamete, and wherein the male gamete is a round spermatid, elongating spermatid, condensing spermatid, or condensed spermatid.

13. The method of claim 1, wherein the method comprises administering the compound that increases bioavailability of a TET protein and the sperm extract into a male gamete, and wherein the male gamete is prepared by differentiating an embryonic stem cell, induced pluripotent stem cell, or spermatogonia stem cell.

14. The method of claim 1, wherein the oocyte, the male gamete, or the fertilized embryo comprises a gene mutation or anomaly in the genome thereof, and the method further comprises administering into the oocyte, the male gamete, or the fertilized embryo comprising a gene mutation or anomaly in the genome thereof an effective amount of a gene editing composition to correct the gene mutation or anomaly.

15. The method of claim 14, wherein the gene editing composition comprises a CRISPR/Cas system, a zinc finger nuclease, or a transcription activator-like effector nuclease and optionally, a donor polynucleotide.

16. The method of claim 1, wherein the method comprises administering the compound that increases bioavailability of a TET protein and the sperm extract into a male gamete, and wherein the male gamete is prepared by a method of differentiating a cell selected from the group consisting of an embryonic stem cell, induced pluripotent stem cell, or spermatogonia stem cell into a round spermatid, elongating spermatid, condensing spermatid, or condensed spermatid.

17. The method of claim 16, wherein the method of differentiating the cell does not include feeder cells.

18. The method of claim 1, further comprising administering into the oocyte, male gamete, or fertilized embryo trichostatin A (TSA).

19. A composition comprising a sperm extract and a compound that increases bioavailability of a TET protein to improve development of a fertilized embryo, or a subsequent embryo resulting from fertilization of an oocyte by a male gamete.

20. A method of improving embryo development comprising administering into a male gamete or a fertilized embryo an effective amount of a compound that increases bioavailability of a TET protein to improve development of the fertilized embryo, or a subsequent embryo resulting from fertilization of an oocyte by the male gamete,
wherein the male gamete is prepared by a method of differentiating a cell selected from the group consisting of an embryonic stem cell, induced pluripotent stem cell, or spermatogonia stem cell into a round spermatid, elongating spermatid, condensing spermatid, or condensed spermatid.

* * * * *

SEQUENCE LISTING

<160> NUMBER OF SEQ ID NOS: 15

<210> SEQ ID NO 1
<211> LENGTH: 1660
<212> TYPE: PRT
<213> ORGANISM: Homo sapiens

<400> SEQUENCE: 1

```
Met Asp Ser Gly Pro Val Tyr His Gly Asp Ser Arg Gln Leu Ser Ala
1               5                   10                  15

Ser Gly Val Pro Val Asn Gly Ala Arg Glu Pro Ala Gly Pro Ser Leu
            20                  25                  30

Leu Gly Thr Gly Gly Pro Trp Arg Val Asp Gln Lys Pro Asp Trp Glu
        35                  40                  45

Ala Ala Pro Gly Pro Ala His Thr Ala Arg Leu Glu Asp Ala His Asp
    50                  55                  60

Leu Val Ala Phe Ser Ala Val Ala Glu Ala Val Ser Ser Tyr Gly Ala
65                  70                  75                  80

Leu Ser Thr Arg Leu Tyr Glu Thr Phe Asn Arg Glu Met Ser Arg Glu
                85                  90                  95

Ala Gly Asn Asn Ser Arg Gly Pro Arg Pro Gly Pro Glu Gly Cys Ser
            100                 105                 110

Ala Gly Ser Glu Asp Leu Asp Thr Leu Gln Thr Ala Leu Ala Leu Ala
        115                 120                 125

Arg His Gly Met Lys Pro Pro Asn Cys Asn Cys Asp Gly Pro Glu Cys
    130                 135                 140

Pro Asp Tyr Leu Glu Trp Leu Glu Gly Lys Ile Lys Ser Val Val Met
145                 150                 155                 160

Glu Gly Gly Glu Glu Arg Pro Arg Leu Pro Gly Pro Leu Pro Pro Gly
                165                 170                 175

Glu Ala Gly Leu Pro Ala Pro Ser Thr Arg Pro Leu Leu Ser Ser Glu
            180                 185                 190

Val Pro Gln Ile Ser Pro Gln Glu Gly Leu Pro Leu Ser Gln Ser Ala
        195                 200                 205

Leu Ser Ile Ala Lys Glu Lys Asn Ile Ser Leu Gln Thr Ala Ile Ala
    210                 215                 220
```

-continued

Ile Glu Ala Leu Thr Gln Leu Ser Ser Ala Leu Pro Gln Pro Ser His
225                 230                 235                 240

Ser Thr Pro Gln Ala Ser Cys Pro Leu Pro Glu Ala Leu Ser Pro Pro
            245                 250                 255

Ala Pro Phe Arg Ser Pro Gln Ser Tyr Leu Arg Ala Pro Ser Trp Pro
            260                 265                 270

Val Val Pro Pro Glu His Ser Ser Phe Ala Pro Asp Ser Ser Ala
        275                 280                 285

Phe Pro Pro Ala Thr Pro Arg Thr Glu Phe Pro Glu Ala Trp Gly Thr
290                 295                 300

Asp Thr Pro Pro Ala Thr Pro Arg Ser Ser Trp Pro Met Pro Arg Pro
305                 310                 315                 320

Ser Pro Asp Pro Met Ala Glu Leu Glu Gln Leu Leu Gly Ser Ala Ser
                325                 330                 335

Asp Tyr Ile Gln Ser Val Phe Lys Arg Pro Glu Ala Leu Pro Thr Lys
            340                 345                 350

Pro Lys Val Lys Val Glu Ala Pro Ser Ser Pro Ala Pro Ala Pro
        355                 360                 365

Ser Pro Val Leu Gln Arg Glu Ala Pro Thr Pro Ser Ser Glu Pro Asp
370                 375                 380

Thr His Gln Lys Ala Gln Thr Ala Leu Gln Gln His Leu His His Lys
385                 390                 395                 400

Arg Ser Leu Phe Leu Glu Gln Val His Asp Thr Ser Phe Pro Ala Pro
                405                 410                 415

Ser Glu Pro Ser Ala Pro Gly Trp Trp Pro Pro Ser Pro Val
            420                 425                 430

Pro Arg Leu Pro Asp Arg Pro Pro Lys Glu Lys Lys Lys Leu Pro
            435                 440                 445

Thr Pro Ala Gly Gly Pro Val Gly Thr Glu Lys Ala Ala Pro Gly Ile
450                 455                 460

Lys Pro Ser Val Arg Lys Pro Ile Gln Ile Lys Lys Ser Arg Pro Arg
465                 470                 475                 480

Glu Ala Gln Pro Leu Phe Pro Pro Val Arg Gln Ile Val Leu Glu Gly
                485                 490                 495

Leu Arg Ser Pro Ala Ser Gln Glu Val Gln Ala His Pro Pro Ala Pro
            500                 505                 510

Leu Pro Ala Ser Gln Gly Ser Ala Val Pro Leu Pro Glu Pro Ser
            515                 520                 525

Leu Ala Leu Phe Ala Pro Ser Pro Ser Arg Asp Ser Leu Leu Pro Pro
530                 535                 540

Thr Gln Glu Met Arg Ser Pro Ser Pro Met Thr Ala Leu Gln Pro Gly
545                 550                 555                 560

Ser Thr Gly Pro Leu Pro Pro Ala Asp Asp Lys Leu Glu Glu Leu Ile
                565                 570                 575

Arg Gln Phe Glu Ala Glu Phe Gly Asp Ser Phe Gly Leu Pro Gly Pro
            580                 585                 590

Pro Ser Val Pro Ile Gln Asp Pro Glu Asn Gln Gln Thr Cys Leu Pro
            595                 600                 605

Ala Pro Glu Ser Pro Phe Ala Thr Arg Ser Pro Lys Gln Ile Lys Ile
            610                 615                 620

Glu Ser Ser Gly Ala Val Thr Val Leu Ser Thr Thr Cys Phe His Ser
625                 630                 635                 640

-continued

Glu Glu Gly Gly Gln Glu Ala Thr Pro Thr Lys Ala Glu Asn Pro Leu
                645                 650                 655

Thr Pro Thr Leu Ser Gly Phe Leu Glu Ser Pro Leu Lys Tyr Leu Asp
        660                 665                 670

Thr Pro Thr Lys Ser Leu Leu Asp Thr Pro Ala Lys Arg Ala Gln Ala
        675                 680                 685

Glu Phe Pro Thr Cys Asp Cys Val Glu Gln Ile Val Glu Lys Asp Glu
        690                 695                 700

Gly Pro Tyr Tyr Thr His Leu Gly Ser Gly Pro Thr Val Ala Ser Ile
705                 710                 715                 720

Arg Glu Leu Met Glu Glu Arg Tyr Gly Glu Lys Gly Lys Ala Ile Arg
                725                 730                 735

Ile Glu Lys Val Ile Tyr Thr Gly Lys Glu Gly Lys Ser Ser Arg Gly
                740                 745                 750

Cys Pro Ile Ala Lys Trp Val Ile Arg Arg His Thr Leu Glu Glu Lys
            755                 760                 765

Leu Leu Cys Leu Val Arg His Arg Ala Gly His His Cys Gln Asn Ala
        770                 775                 780

Val Ile Val Ile Leu Ile Leu Ala Trp Glu Gly Ile Pro Arg Ser Leu
785                 790                 795                 800

Gly Asp Thr Leu Tyr Gln Glu Leu Thr Asp Thr Leu Arg Lys Tyr Gly
                805                 810                 815

Asn Pro Thr Ser Arg Arg Cys Gly Leu Asn Asp Asp Arg Thr Cys Ala
                820                 825                 830

Cys Gln Gly Lys Asp Pro Asn Thr Cys Gly Ala Ser Phe Ser Phe Gly
        835                 840                 845

Cys Ser Trp Ser Met Tyr Phe Asn Gly Cys Lys Tyr Ala Arg Ser Lys
    850                 855                 860

Thr Pro Arg Lys Phe Arg Leu Ala Gly Asp Asn Pro Lys Glu Glu Glu
865                 870                 875                 880

Val Leu Arg Lys Ser Phe Gln Asp Leu Ala Thr Glu Val Ala Pro Leu
                885                 890                 895

Tyr Lys Arg Leu Ala Pro Gln Ala Tyr Gln Asn Gln Val Thr Asn Glu
            900                 905                 910

Glu Ile Ala Ile Asp Cys Arg Leu Gly Leu Lys Glu Gly Arg Pro Phe
        915                 920                 925

Ala Gly Val Thr Ala Cys Met Asp Phe Cys Ala His Ala His Lys Asp
        930                 935                 940

Gln His Asn Leu Tyr Asn Gly Cys Thr Val Val Cys Thr Leu Thr Lys
945                 950                 955                 960

Glu Asp Asn Arg Cys Val Gly Lys Ile Pro Glu Asp Glu Gln Leu His
                965                 970                 975

Val Leu Pro Leu Tyr Lys Met Ala Asn Thr Asp Glu Phe Gly Ser Glu
            980                 985                 990

Glu Asn Gln Asn Ala Lys Val Gly Ser Gly Ala Ile Gln Val Leu Thr
            995                 1000                1005

Ala Phe Pro Arg Glu Val Arg Arg Leu Pro Glu Pro Ala Lys Ser
    1010                1015                1020

Cys Arg Gln Arg Gln Leu Glu Ala Arg Lys Ala Ala Ala Glu Lys
    1025                1030                1035

Lys Lys Ile Gln Lys Glu Lys Leu Ser Thr Pro Glu Lys Ile Lys
    1040                1045                1050

Gln Glu Ala Leu Glu Leu Ala Gly Ile Thr Ser Asp Pro Gly Leu

-continued

|   |   |   | 1055 |   |   |   |   | 1060 |   |   |   |   | 1065 |   |   |
|---|---|---|------|---|---|---|---|------|---|---|---|---|------|---|---|

Ser Leu Lys Gly Gly Leu Ser Gln Gln Gly Leu Lys Pro Ser Leu
        1070                1075                1080

Lys Val Glu Pro Gln Asn His Phe Ser Ser Phe Lys Tyr Ser Gly
1085                1090                1095

Asn Ala Val Val Glu Ser Tyr Ser Val Leu Gly Asn Cys Arg Pro
1100                1105                1110

Ser Asp Pro Tyr Ser Met Asn Ser Val Tyr Ser Tyr His Ser Tyr
1115                1120                1125

Tyr Ala Gln Pro Ser Leu Thr Ser Val Asn Gly Phe His Ser Lys
1130                1135                1140

Tyr Ala Leu Pro Ser Phe Ser Tyr Tyr Gly Phe Pro Ser Ser Asn
1145                1150                1155

Pro Val Phe Pro Ser Gln Phe Leu Gly Pro Gly Ala Trp Gly His
1160                1165                1170

Ser Gly Ser Ser Gly Ser Phe Glu Lys Lys Pro Asp Leu His Ala
1175                1180                1185

Leu His Asn Ser Leu Ser Pro Ala Tyr Gly Gly Ala Glu Phe Ala
1190                1195                1200

Glu Leu Pro Ser Gln Ala Val Pro Thr Asp Ala His His Pro Thr
1205                1210                1215

Pro His His Gln Gln Pro Ala Tyr Pro Gly Pro Lys Glu Tyr Leu
1220                1225                1230

Leu Pro Lys Ala Pro Leu Leu His Ser Val Ser Arg Asp Pro Ser
1235                1240                1245

Pro Phe Ala Gln Ser Ser Asn Cys Tyr Asn Arg Ser Ile Lys Gln
1250                1255                1260

Glu Pro Val Asp Pro Leu Thr Gln Ala Glu Pro Val Pro Arg Asp
1265                1270                1275

Ala Gly Lys Met Gly Lys Thr Pro Leu Ser Glu Val Ser Gln Asn
1280                1285                1290

Gly Gly Pro Ser His Leu Trp Gly Gln Tyr Ser Gly Gly Pro Ser
1295                1300                1305

Met Ser Pro Lys Arg Thr Asn Gly Val Gly Gly Ser Trp Gly Val
1310                1315                1320

Phe Ser Ser Gly Glu Ser Pro Ala Ile Val Pro Asp Lys Leu Ser
1325                1330                1335

Ser Phe Gly Ala Ser Cys Leu Ala Pro Ser His Phe Thr Asp Gly
1340                1345                1350

Gln Trp Gly Leu Phe Pro Gly Glu Gly Gln Gln Ala Ala Ser His
1355                1360                1365

Ser Gly Gly Arg Leu Arg Gly Lys Pro Trp Ser Pro Cys Lys Phe
1370                1375                1380

Gly Asn Ser Thr Ser Ala Leu Ala Gly Pro Ser Leu Thr Glu Lys
1385                1390                1395

Pro Trp Ala Leu Gly Ala Gly Asp Phe Asn Ser Ala Leu Lys Gly
1400                1405                1410

Ser Pro Gly Phe Gln Asp Lys Leu Trp Asn Pro Met Lys Gly Glu
1415                1420                1425

Glu Gly Arg Ile Pro Ala Ala Gly Ala Ser Gln Leu Asp Arg Ala
1430                1435                1440

Trp Gln Ser Phe Gly Leu Pro Leu Gly Ser Ser Glu Lys Leu Phe
1445                1450                1455

-continued

| | | | | | | | | | | |
|---|---|---|---|---|---|---|---|---|---|---|
|Gly|Ala|Leu|Lys|Ser|Glu|Glu|Lys|Leu|Trp|Asp|Pro|Phe|Ser|Leu|
| |1460| | | |1465| | | |1470| | | | | |

Gly Ala Leu Lys Ser Glu Glu Lys Leu Trp Asp Pro Phe Ser Leu
        1460                1465                1470

Glu Glu Gly Pro Ala Glu Glu Pro Pro Ser Lys Gly Ala Val Lys
    1475                1480                1485

Glu Glu Lys Gly Gly Gly Ala Glu Glu Glu Glu Glu Leu
    1490                1495                1500

Trp Ser Asp Ser Glu His Asn Phe Leu Asp Glu Asn Ile Gly Gly
    1505                1510                1515

Val Ala Val Ala Pro Ala His Gly Ser Ile Leu Ile Glu Cys Ala
    1520                1525                1530

Arg Arg Glu Leu His Ala Thr Thr Pro Leu Lys Lys Pro Asn Arg
    1535                1540                1545

Cys His Pro Thr Arg Ile Ser Leu Val Phe Tyr Gln His Lys Asn
    1550                1555                1560

Leu Asn Gln Pro Asn His Gly Leu Ala Leu Trp Glu Ala Lys Met
    1565                1570                1575

Lys Gln Leu Ala Glu Arg Ala Arg Ala Arg Gln Glu Glu Ala Ala
    1580                1585                1590

Arg Leu Gly Leu Gly Gln Gln Glu Ala Lys Leu Tyr Gly Lys Lys
    1595                1600                1605

Arg Lys Trp Gly Gly Thr Val Val Ala Glu Pro Gln Gln Lys Glu
    1610                1615                1620

Lys Lys Gly Val Val Pro Thr Arg Gln Ala Leu Ala Val Pro Thr
    1625                1630                1635

Asp Ser Ala Val Thr Val Ser Ser Tyr Ala Tyr Thr Lys Val Thr
    1640                1645                1650

Gly Pro Tyr Ser Arg Trp Ile
    1655                1660

<210> SEQ ID NO 2
<211> LENGTH: 5388
<212> TYPE: DNA
<213> ORGANISM: Homo sapiens

<400> SEQUENCE: 2

```
atgagccagt tcaggtgcc cctggccgtc cagccggacc tgccaggcct ttatgacttc      60
cctcagcgcc aggtgatggt agggagcttc ccggggtctg ggctctccat ggctgggagt     120
gagtcccaac tccagggggg tggagatggt cgaaagaaac ggaaacggtg tggtacttgt     180
gagccctgcc ggcggctgga aaactgtggc gcttgcacta gctgtaccaa cgccgcacg     240 caccagatct gcaaactgcg aaaatgtgag gtgctgaaga aaaagtagg gcttctcaag     300 gaggtggaaa taaggctgg tgaaggagcc gggccgtggg acaaggagc ggctgtcaag     360 acaggctcag agctcagccc agttgatgga cctgttccag gtcagatgga ctcagggcca    420
gtgtaccatg gggactcacg gcagctaagc gcctcagggg tgccggtcaa tggtgctaga    480
gagcccgctg acccagtctg ctggggact ggggtcctt ggcgggtaga ccaaaagccc      540
gactgggagg ctgccccagg cccagctcat actgctcgcc tggaagatgc ccacgatctg    600 gtggccttt cggctgtggc cgaagctgtg tcctcttatg ggcccttag cacccggctc    660 tatgaaacct caaccgtga tgagtcgt gaggctggga caacagcag ggaccccgg         720 ccagggcctg aggctgctc tgctggcagc gaagaccttg acacactgca gacgccctg      780 gccctcgcgc ggcatggtat gaaaccaccc aactgcaact gcgatggccc agaatgccct    840
```

```
gactacctcg agtggctgga ggggaagatc aagtctgtgg tcatggaagg aggggaggag    900
cggcccaggc tcccagggcc tctgcctcct ggtgaggccg gcctcccagc accaagcacc    960
aggccactcc tcagctcaga ggtgccccag atctctcccc aagagggcct gcccctgtcc   1020
cagagtgccc tgagcattgc caaggaaaaa aacatcagct tgcagaccgc cattgccatt   1080
gaggccctca cacagctctc ctctgccctc ccgcagcctt ctcattccac cccccaggct   1140
tcttgccccc ttcctgaggc cttgtcacct cctgccccctt tcagatctcc ccagtcttac   1200
ctccgggctc cctcatggcc tgtggttcct cctgaagagc actcatcttt tgctcctgat   1260
agctctgcct tccctccagc aactcctaga actgagttcc ctgaagcctg ggcactgac    1320
acccctccag caacgccccg gagctcctgg cccatgcctc gcccaagccc cgatcccatg   1380
gctgaactgg agcagttgtt gggcagcgcc agtgattaca tccagtcagt attcaagcgg   1440
cctgaggccc tgcctaccaa gcccaaggtc aaggtggagg caccctcttc ctccccggcc   1500
ccggccccat cccctgtact tcagagggag gctcccacgc catcctcgga gccccgacacc   1560
caccagaagg cccagaccgc cctgcagcag cacctccacc acaagcgcag cctcttccta   1620
gaacaggtgc acgacacctc cttccctgct ccttcagagc cttctgctcc tggctggtgg   1680
cccccaccaa gttcacctgt cccacggctt ccagacagac cacccaagga gaagaagaag   1740
aagctcccaa caccagctgg aggtcccgtg ggaacggaga agctgcccc tgggatcaag    1800
cccagtgtcc gaaagcccat tcagatcaag aagtccaggc ccgggaagc acagcccctc    1860
ttcccacctg tccgacagat tgtcctggaa gggcttaggt ccccagcctc caggaagtg    1920
caggctcatc caccggcccc tctgcctgcc tcacagggct ctgctgtgcc cctgcccca    1980
gaaccttctc ttgcgctatt tgcacctagt ccctccaggg acagcctgct gcccctact    2040
caggaaatga ggtcccccag ccccatgaca gccttgcagc caggctccac tggccctctt   2100
ccccctgccg atgacaagct ggaagagctc atccggcagt ttgaggctga atttggagat   2160
agctttgggc ttcccggccc ccttctgtg cccattcagg accccgagaa ccagcaaaca    2220
tgtctcccag cccctgagag ccccttttgct acccgttccc ccaagcaaat caagattgag   2280
tcttcggggc tgtgactgt gctctcaacc acctgcttcc attcagagga gggaggacag    2340
gaggccacac ccaccaaggc tgagaaccca ctcacaccca ccctcagtgg cttcttggag   2400
tcacctctta agtacctgga cacacccacc aagagtctgc tggacacacc tgccaagaga   2460
gcccaggccg agttccccac ctgcgattgc gtcgaacaaa tagtggagaa agatgaaggt   2520
ccatattata ctcacttggg atctggcccc acggtcgcct ctatccggga actcatggag   2580
gagcggtatg agagaagggg gaaagccatc cggatcgaga aggtcatcta cacggggaag   2640
gagggaaaga gctcccgcgg ttgccccatt gcaaagtggg tgatccgcag gcacacgctg   2700
gaggagaagc tactctgcct ggtgcggcac cgggcaggcc accactgcca gaacgctgtg   2760
atcgtcatcc tcatcctggc ctgggagggc attccccgta gcctcggaga cccctctac    2820
caggagctca ccgacaccct ccggaagtat gggaaccccca ccagccggag atgcggcctc   2880
aacgatgacc ggacctgcgc ttgccaaggc aaagaccccca acacctgtgg tgcctccttc   2940
tcctttggtt gttcctggag catgtacttc aacggctgca agtatgctcg gagcaagaca   3000
cctcgcaagt tccgcctcgc aggggacaat cccaaagagg aagaagtgct ccggaagagt   3060
ttccaggacc tggccaccga agtcgctccc ctgtacaagc gactggcccc tcaggcctat   3120
cagaaccagt gaccaacga ggaaatagcg attgactgcc gtctggggct gaaggaagga   3180
cggcccttcg cggggtcac ggcctgcatg gacttctgtg cccacgccca caggaccag    3240
```

```
cataacctct acaatgggtg caccgtggtc tgcaccctga ccaaggaaga caatcgctgc    3300
gtgggcaaga ttcccgagga tgagcagctg catgttctcc cctgtacaa gatggccaac     3360 acggatgagt ttggtagcga ggagaaccag aatgcaaagg tgggcagcgg agccatccag    3420
gtgctcaccg ccttcccccg cgaggtccga cgcctgcccg agcctgccaa gtcctgccgc    3480
cagcggcagc tggaagccag aaaggcagca gccgagaaga agaagattca gaaggagaag    3540
ctgagcactc cggagaagat caagcaggag ccctgagc tggcgggcat acgtcggac       3600 ccaggcctgt ctctgaaggg tggattgtcc cagcaaggcc tgaagccctc cctcaaggtg    3660
gagccgcaga accacttcag ctccttcaag tacagcggca cgcggtggt ggagagctac     3720 tcggtgctgg gcaactgccg gccctccgac ccttacagca tgaacagcgt gtactcctac    3780
cactcctact atgcacagcc cagcctgacc tccgtcaatg gcttccactc caagtacgct    3840
ctcccgtctt ttagctacta tggctttcca tccagcaacc ccgtcttccc ctctcagttc    3900
ctgggtcctg gtgcctgggg gcacagtggc agcagtggca gttttgagaa gaagccagac    3960
ctccacgctc tgcacaacag cctgagcccg gcctacggtg gtgctgagtt tgccgagctg    4020
cccagccagg ctgttcccac agacgcccac caccccactc ctcaccacca gcagcctgcg    4080
tacccaggcc ccaaggagta tctgcttccc aaggcccccc tactccactc agtgtccagg    4140 gaccctcc cctttgccca gagctccaac tgctacaaca gatccatcaa gcaagagcca     4200
gtagacccgc tgacccaggc tgagcctgtg cccagagacg ctggcaagat gggcaagaca    4260
cctctgtccg aggtgtctca gaatggagga cccagtcacc tttggggaca gtactcagga    4320
ggcccaagca tgtcccccaa gaggactaac ggtgtgggtg gcagctgggg tgtgttctcg    4380
tctggggaga gtcctgccat cgtccctgac aagctcagtt cctttgggc cagctgcctg    4440 gcccccttccc acttcacaga tggccagtgg gggctgttcc ccggtgaggg gcagcaggca    4500
gcttcccact ctggaggacg gctgcgaggc aaaccgtgga gccctgcaa gtttgggaac    4560 agcacctcgg ccttggctgg gcccagcctg actgagaagc cgtgggcgct gggggcaggg    4620
gatttcaact cggccctgaa aggtagtcct gggttccaag acaagctgtg gaaccccatg    4680
aaaggagagg agggcaggat ccagccgca ggggccagcc agctggacag ggcctggcag    4740
tcctttggtc tgcccctggg atccagcgag aagctgtttg gggctctgaa gtcagaggag    4800
aagctgtggg acccctttcag cctggaggag gggccggctg aggagccccc cagcaaggga    4860
gcggtgaagg aggagaaggg cggtggtggt gcggaggagg aagaggagga gctgtggtcg    4920
gacagtgaac acaacttcct ggacgagaac atcggcggcg tggccgtggc cccagcccac    4980
ggctccatcc tcatcgagtg tgcccggcgg gagctgcacg ccaccacgcc gcttaagaag    5040
cccaaccgct gccaccccac ccgcatctcg ctggtcttct accagcacaa gaacctcaac    5100
cagcccaacc acgggctggc cctctgggaa gccaagatga gcagctggc ggagagggca    5160 cgggcacggc aggaggaggc tgcccggctg gcctgggcc agcaggaggc caagctctac    5220
gggaagaagc gcaagtgggg gggcactgtg gttgctgagc cccagcagaa agagaagaag    5280
ggggtcgtcc ccacccggca ggcactggct gtgcccacag actcggcggt caccgtgtcc    5340
tcctatgcct acacgaaggt cactggcccc tacagccgct ggatctag              5388
```

<210> SEQ ID NO 3
<211> LENGTH: 136
<212> TYPE: PRT
<213> ORGANISM: Artificial Sequence
<220> FEATURE:

<223> OTHER INFORMATION: synthetic polypeptide

<400> SEQUENCE: 3

Met Ser Gln Phe Gln Val Pro Leu Ala Val Gln Pro Asp Leu Pro Gly
1               5                   10                  15

Leu Tyr Asp Phe Pro Gln Arg Gln Val Met Val Gly Ser Phe Pro Gly
            20                  25                  30

Ser Gly Leu Ser Met Ala Gly Ser Glu Ser Gln Leu Arg Gly Gly Gly
        35                  40                  45

Asp Gly Arg Lys Lys Arg Lys Arg Cys Gly Thr Cys Glu Pro Cys Arg
    50                  55                  60

Arg Leu Glu Asn Cys Gly Ala Cys Thr Ser Cys Thr Asn Arg Arg Thr
65                  70                  75                  80

His Gln Ile Cys Lys Leu Arg Lys Cys Glu Val Leu Lys Lys Lys Val
                85                  90                  95

Gly Leu Leu Lys Glu Val Glu Ile Lys Ala Gly Glu Gly Ala Gly Pro
            100                 105                 110

Trp Gly Gln Gly Ala Ala Val Lys Thr Gly Ser Glu Leu Ser Pro Val
        115                 120                 125

Asp Gly Pro Val Pro Gly Gln Met
    130                 135

<210> SEQ ID NO 4
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 4
cctgcagaaa cgggaccacg aggg                                           24

<210> SEQ ID NO 5
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 5
cctgcagaaa cgggaccatg aggg                                           24

<210> SEQ ID NO 6
<211> LENGTH: 23
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (21)..(21)
<223> OTHER INFORMATION: n is a, c, g, or t

<400> SEQUENCE: 6
gctgcagaaa cgggaccacg ngg                                            23

<210> SEQ ID NO 7
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 7
cctgcagaaa cgggaccatg agggctttgg ttttg                                  35

<210> SEQ ID NO 8
<211> LENGTH: 29
<212> TYPE: DNA
<213> ORGANISM: Artificial Sequence
<220> FEATURE:
<223> OTHER INFORMATION: synthetic polynucleotide

<400> SEQUENCE: 8
cctgcagaaa cgggaccatt ttggttttg                                         29

<210> SEQ ID NO 9
<211> LENGTH: 2002
<212> TYPE: PRT
<213> ORGANISM: Homo sapiens

<400> SEQUENCE: 9

```
Met Glu Gln Asp Arg Thr Asn His Val Glu Gly Asn Arg Leu Ser Pro
1               5                   10                  15

Phe Leu Ile Pro Ser Pro Pro Ile Cys Gln Thr Glu Pro Leu Ala Thr
            20                  25                  30

Lys Leu Gln Asn Gly Ser Pro Leu Pro Glu Arg Ala His Pro Glu Val
        35                  40                  45

Asn Gly Asp Thr Lys Trp His Ser Phe Lys Ser Tyr Tyr Gly Ile Pro
    50                  55                  60

Cys Met Lys Gly Ser Gln Asn Ser Arg Val Ser Pro Asp Phe Thr Gln
65                  70                  75                  80

Glu Ser Arg Gly Tyr Ser Lys Cys Leu Gln Asn Gly Gly Ile Lys Arg
                85                  90                  95

Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205

Asn Gly Ala Thr Val Ser Ala Ser Ser Val Glu His Thr His Gly Glu
    210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
            260                 265                 270

Gln Ile Asn Ser Ala Gln Thr Ser Asn Ser Glu Leu Pro Pro Lys Pro
        275                 280                 285

Ala Ala Val Val Ser Glu Ala Cys Asp Ala Asp Asp Ala Asp Asn Ala
```

```
              290                 295                 300
Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
                    325                 330                 335

Glu Asn Asn Ile Gln Gly Thr Thr Lys Leu Ala Ser Gly Glu Glu Phe
                340                 345                 350

Cys Ser Gly Ser Ser Ser Asn Leu Gln Ala Pro Gly Gly Ser Ser Glu
                355                 360                 365

Arg Tyr Leu Lys Gln Asn Glu Met Asn Gly Ala Tyr Phe Lys Gln Ser
                370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Leu Pro Gln Val Pro
                    405                 410                 415

Gln Leu Pro Ser Glu Gly Lys Ser Thr Leu Asn Gly Gly Val Leu Glu
                420                 425                 430

Glu His His His Tyr Pro Asn Gln Ser Asn Thr Thr Leu Leu Arg Glu
                435                 440                 445

Val Lys Ile Glu Gly Lys Pro Glu Ala Pro Pro Ser Gln Ser Pro Asn
450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
                500                 505                 510

Lys His Asn Pro Pro Ile Phe Gly Ser Ser Gly Glu Leu Gln Asp Asn
                515                 520                 525

Cys Gln Gln Leu Met Arg Asn Lys Glu Gln Glu Ile Leu Lys Gly Arg
                530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                    565                 570                 575

Ser His Leu Lys Arg Asn Glu Ala Ser Leu Pro Ser Ile Leu Gln Tyr
                580                 585                 590

Gln Pro Asn Leu Ser Asn Gln Met Thr Ser Lys Gln Tyr Thr Gly Asn
                595                 600                 605

Ser Asn Met Pro Gly Gly Leu Pro Arg Gln Ala Tyr Thr Gln Lys Thr
                610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                    645                 650                 655

Ser His Gln Val His Phe Ser Lys Thr Asp His Leu Pro Lys Ala His
                660                 665                 670

Val Gln Ser Leu Cys Gly Thr Arg Phe His Phe Gln Gln Arg Ala Asp
                675                 680                 685

Ser Gln Thr Glu Lys Leu Met Ser Pro Val Leu Lys Gln His Leu Asn
                690                 695                 700

Gln Gln Ala Ser Glu Thr Glu Pro Phe Ser Asn Ser His Leu Leu Gln
705                 710                 715                 720
```

His Lys Pro His Lys Gln Ala Ala Gln Thr Gln Pro Ser Gln Ser Ser
              725                 730                 735

His Leu Pro Gln Asn Gln Gln Gln Gln Lys Leu Gln Ile Lys Asn
    740                 745                 750

Lys Glu Glu Ile Leu Gln Thr Phe Pro His Pro Gln Ser Asn Asn Asp
        755                 760                 765

Gln Gln Arg Glu Gly Ser Phe Phe Gly Gln Thr Lys Val Glu Glu Cys
770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                805                 810                 815

Ser Pro Tyr Ser Gln Thr Met Lys Ser Ser Ala Cys Lys Ile Gln Val
            820                 825                 830

Ser Cys Ser Asn Asn Thr His Leu Val Ser Glu Asn Lys Glu Gln Thr
        835                 840                 845

Thr His Pro Glu Leu Phe Ala Gly Asn Lys Thr Gln Asn Leu His His
    850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
            900                 905                 910

Gln Leu Ala Gln Gln Arg Tyr Leu Ile His Asn His Ala Asn Val Phe
        915                 920                 925

Pro Val Pro Asp Gln Gly Gly Ser His Thr Gln Thr Pro Pro Gln Lys
    930                 935                 940

Asp Thr Gln Lys His Ala Ala Leu Arg Trp His Leu Leu Gln Lys Gln
945                 950                 955                 960

Glu Gln Gln Gln Thr Gln Gln Pro Gln Thr Glu Ser Cys His Ser Gln
                965                 970                 975

Met His Arg Pro Ile Lys Val Glu Pro Gly Cys Lys Pro His Ala Cys
            980                 985                 990

Met His Thr Ala Pro Pro Glu Asn Lys Thr Trp Lys Lys Val Thr Lys
        995                 1000                1005

Gln Glu Asn Pro Pro Ala Ser Cys Asp Asn Val Gln Gln Lys Ser
    1010                1015                1020

Ile Ile Glu Thr Met Glu Gln His Leu Lys Gln Phe His Ala Lys
    1025                1030                1035

Ser Leu Phe Asp His Lys Ala Leu Thr Leu Lys Ser Gln Lys Gln
    1040                1045                1050

Val Lys Val Glu Met Ser Gly Pro Val Thr Val Leu Thr Arg Gln
    1055                1060                1065

Thr Thr Ala Ala Glu Leu Asp Ser His Thr Pro Ala Leu Glu Gln
    1070                1075                1080

Gln Thr Thr Ser Ser Glu Lys Thr Pro Thr Lys Arg Thr Ala Ala
    1085                1090                1095

Ser Val Leu Asn Asn Phe Ile Glu Ser Pro Ser Lys Leu Leu Asp
    1100                1105                1110

Thr Pro Ile Lys Asn Leu Leu Asp Thr Pro Val Lys Thr Gln Tyr
    1115                1120                1125

```
Asp Phe Pro Ser Cys Arg Cys Val Glu Gln Ile Ile Glu Lys Asp
    1130                1135                1140

Glu Gly Pro Phe Tyr Thr His Leu Gly Ala Gly Pro Asn Val Ala
    1145                1150                1155

Ala Ile Arg Glu Ile Met Glu Arg Phe Gly Gln Lys Gly Lys
    1160                1165                1170

Ala Ile Arg Ile Glu Arg Val Ile Tyr Thr Lys Glu Gly Lys
    1175                1180                1185

Ser Ser Gln Gly Cys Pro Ile Ala Lys Trp Val Val Arg Arg Ser
    1190                1195                1200

Ser Ser Glu Glu Lys Leu Leu Cys Leu Val Arg Glu Arg Ala Gly
    1205                1210                1215

His Thr Cys Glu Ala Ala Val Ile Val Ile Leu Ile Leu Val Trp
    1220                1225                1230

Glu Gly Ile Pro Leu Ser Leu Ala Asp Lys Leu Tyr Ser Glu Leu
    1235                1240                1245

Thr Glu Thr Leu Arg Lys Tyr Gly Thr Leu Thr Asn Arg Arg Cys
    1250                1255                1260

Ala Leu Asn Glu Glu Arg Thr Cys Ala Cys Gln Gly Leu Asp Pro
    1265                1270                1275

Glu Thr Cys Gly Ala Ser Phe Ser Phe Gly Cys Ser Trp Ser Met
    1280                1285                1290

Tyr Tyr Asn Gly Cys Lys Phe Ala Arg Ser Lys Ile Pro Arg Lys
    1295                1300                1305

Phe Lys Leu Leu Gly Asp Asp Pro Lys Glu Glu Lys Leu Glu
    1310                1315                1320

Ser His Leu Gln Asn Leu Ser Thr Leu Met Ala Pro Thr Tyr Lys
    1325                1330                1335

Lys Leu Ala Pro Asp Ala Tyr Asn Asn Gln Ile Glu Tyr Glu His
    1340                1345                1350

Arg Ala Pro Glu Cys Arg Leu Gly Leu Lys Glu Gly Arg Pro Phe
    1355                1360                1365

Ser Gly Val Thr Ala Cys Leu Asp Phe Cys Ala His Ala His Arg
    1370                1375                1380

Asp Leu His Asn Met Gln Asn Gly Ser Thr Leu Val Cys Thr Leu
    1385                1390                1395

Thr Arg Glu Asp Asn Arg Glu Phe Gly Gly Lys Pro Glu Asp Glu
    1400                1405                1410

Gln Leu His Val Leu Pro Leu Tyr Lys Val Ser Asp Val Asp Glu
    1415                1420                1425

Phe Gly Ser Val Glu Ala Gln Glu Glu Lys Lys Arg Ser Gly Ala
    1430                1435                1440

Ile Gln Val Leu Ser Ser Phe Arg Arg Lys Val Arg Met Leu Ala
    1445                1450                1455

Glu Pro Val Lys Thr Cys Arg Gln Arg Lys Leu Glu Ala Lys Lys
    1460                1465                1470

Ala Ala Ala Glu Lys Leu Ser Ser Leu Glu Asn Ser Ser Asn Lys
    1475                1480                1485

Asn Glu Lys Glu Lys Ser Ala Pro Ser Arg Thr Lys Gln Thr Glu
    1490                1495                1500

Asn Ala Ser Gln Ala Lys Gln Leu Ala Glu Leu Leu Arg Leu Ser
    1505                1510                1515

Gly Pro Val Met Gln Gln Ser Gln Gln Pro Gln Pro Leu Gln Lys
```

```
                    1520                1525                1530

Gln  Pro  Pro  Gln  Pro  Gln  Gln  Gln  Arg  Pro  Gln  Gln  Gln  Gln
          1535                1540                1545

Pro  His  His  Pro  Gln  Thr  Glu  Ser  Val  Asn  Ser  Tyr  Ser  Ala  Ser
     1550                1555                1560

Gly  Ser  Thr  Asn  Pro  Tyr  Met  Arg  Arg  Pro  Asn  Pro  Val  Ser  Pro
     1565                1570                1575

Tyr  Pro  Asn  Ser  Ser  His  Thr  Ser  Asp  Ile  Tyr  Gly  Ser  Thr  Ser
     1580                1585                1590

Pro  Met  Asn  Phe  Tyr  Ser  Thr  Ser  Ser  Gln  Ala  Ala  Gly  Ser  Tyr
     1595                1600                1605

Leu  Asn  Ser  Ser  Asn  Pro  Met  Asn  Pro  Tyr  Pro  Gly  Leu  Leu  Asn
     1610                1615                1620

Gln  Asn  Thr  Gln  Tyr  Pro  Ser  Tyr  Gln  Cys  Asn  Gly  Asn  Leu  Ser
     1625                1630                1635

Val  Asp  Asn  Cys  Ser  Pro  Tyr  Leu  Gly  Ser  Tyr  Ser  Pro  Gln  Ser
     1640                1645                1650

Gln  Pro  Met  Asp  Leu  Tyr  Arg  Tyr  Pro  Ser  Gln  Asp  Pro  Leu  Ser
     1655                1660                1665

Lys  Leu  Ser  Leu  Pro  Pro  Ile  His  Thr  Leu  Tyr  Gln  Pro  Arg  Phe
     1670                1675                1680

Gly  Asn  Ser  Gln  Ser  Phe  Thr  Ser  Lys  Tyr  Leu  Gly  Tyr  Gly  Asn
     1685                1690                1695

Gln  Asn  Met  Gln  Gly  Asp  Gly  Phe  Ser  Ser  Cys  Thr  Ile  Arg  Pro
     1700                1705                1710

Asn  Val  His  His  Val  Gly  Lys  Leu  Pro  Pro  Tyr  Pro  Thr  His  Glu
     1715                1720                1725

Met  Asp  Gly  His  Phe  Met  Gly  Ala  Thr  Ser  Arg  Leu  Pro  Pro  Asn
     1730                1735                1740

Leu  Ser  Asn  Pro  Asn  Met  Asp  Tyr  Lys  Asn  Gly  Glu  His  His  Ser
     1745                1750                1755

Pro  Ser  His  Ile  Ile  His  Asn  Tyr  Ser  Ala  Ala  Pro  Gly  Met  Phe
     1760                1765                1770

Asn  Ser  Ser  Leu  His  Ala  Leu  His  Leu  Gln  Asn  Lys  Glu  Asn  Asp
     1775                1780                1785

Met  Leu  Ser  His  Thr  Ala  Asn  Gly  Leu  Ser  Lys  Met  Leu  Pro  Ala
     1790                1795                1800

Leu  Asn  His  Asp  Arg  Thr  Ala  Cys  Val  Gln  Gly  Gly  Leu  His  Lys
     1805                1810                1815

Leu  Ser  Asp  Ala  Asn  Gly  Gln  Glu  Lys  Gln  Pro  Leu  Ala  Leu  Val
     1820                1825                1830

Gln  Gly  Val  Ala  Ser  Gly  Ala  Glu  Asp  Asn  Asp  Glu  Val  Trp  Ser
     1835                1840                1845

Asp  Ser  Glu  Gln  Ser  Phe  Leu  Asp  Pro  Asp  Ile  Gly  Gly  Val  Ala
     1850                1855                1860

Val  Ala  Pro  Thr  His  Gly  Ser  Ile  Leu  Ile  Glu  Cys  Ala  Lys  Arg
     1865                1870                1875

Glu  Leu  His  Ala  Thr  Thr  Pro  Leu  Lys  Asn  Pro  Asn  Arg  Asn  His
     1880                1885                1890

Pro  Thr  Arg  Ile  Ser  Leu  Val  Phe  Tyr  Gln  His  Lys  Ser  Met  Asn
     1895                1900                1905

Glu  Pro  Lys  His  Gly  Leu  Ala  Leu  Trp  Glu  Ala  Lys  Met  Ala  Glu
     1910                1915                1920
```

```
Lys Ala Arg Glu Lys Glu Glu Cys Glu Lys Tyr Gly Pro Asp
    1925                1930                1935

Tyr Val Pro Gln Lys Ser His Gly Lys Lys Val Lys Arg Glu Pro
    1940                1945                1950

Ala Glu Pro His Glu Thr Ser Glu Pro Thr Tyr Leu Arg Phe Ile
    1955                1960                1965

Lys Ser Leu Ala Glu Arg Thr Met Ser Val Thr Thr Asp Ser Thr
    1970                1975                1980

Val Thr Thr Ser Pro Tyr Ala Phe Thr Arg Val Thr Gly Pro Tyr
    1985                1990                1995

Asn Arg Tyr Ile
    2000

<210> SEQ ID NO 10
<211> LENGTH: 2136
<212> TYPE: PRT
<213> ORGANISM: Homo sapiens

<400> SEQUENCE: 10

Met Ser Arg Ser Arg His Ala Arg Pro Ser Arg Leu Val Arg Lys Glu
1               5                   10                  15

Asp Val Asn Lys Lys Lys Lys Asn Ser Gln Leu Arg Lys Thr Thr Lys
                20                  25                  30

Gly Ala Asn Lys Asn Val Ala Ser Val Lys Thr Leu Ser Pro Gly Lys
            35                  40                  45

Leu Lys Gln Leu Ile Gln Glu Arg Asp Val Lys Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160

Gln Asp Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
        195                 200                 205

Pro Ala Ala Glu Ile Leu Pro Gly Pro Leu Glu Gly Thr Arg Cys Gly
    210                 215                 220

Glu Gly Leu Phe Ser Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
```

```
                    275                 280                 285
Pro Ile Lys Ser Glu His Asp Cys Tyr Pro Thr Ser Ser Leu Asn Lys
            290                 295                 300
Val Ile Pro Asp Leu Asn Leu Arg Asn Cys Leu Ala Leu Gly Gly Ser
305                 310                 315                 320
Thr Ser Pro Thr Ser Val Ile Lys Phe Leu Leu Ala Gly Ser Lys Gln
                325                 330                 335
Ala Thr Leu Gly Ala Lys Pro Asp His Gln Glu Ala Phe Glu Ala Thr
            340                 345                 350
Ala Asn Gln Gln Glu Val Ser Asp Thr Thr Ser Phe Leu Gly Gln Ala
            355                 360                 365
Phe Gly Ala Ile Pro His Gln Trp Glu Leu Pro Gly Ala Asp Pro Val
        370                 375                 380
His Gly Glu Ala Leu Gly Glu Thr Pro Asp Leu Pro Glu Ile Pro Gly
385                 390                 395                 400
Ala Ile Pro Val Gln Gly Glu Val Phe Gly Thr Ile Leu Asp Gln Gln
                405                 410                 415
Glu Thr Leu Gly Met Ser Gly Ser Val Val Pro Asp Leu Pro Val Phe
            420                 425                 430
Leu Pro Val Pro Pro Asn Pro Ile Ala Thr Phe Asn Ala Pro Ser Lys
            435                 440                 445
Trp Pro Glu Pro Gln Ser Thr Val Ser Tyr Gly Leu Ala Val Gln Gly
        450                 455                 460
Ala Ile Gln Ile Leu Pro Leu Gly Ser Gly His Thr Pro Gln Ser Ser
465                 470                 475                 480
Ser Asn Ser Glu Lys Asn Ser Leu Pro Pro Val Met Ala Ile Ser Asn
                485                 490                 495
Val Glu Asn Glu Lys Gln Val His Ile Ser Phe Leu Pro Ala Asn Thr
            500                 505                 510
Gln Gly Phe Pro Leu Ala Pro Glu Arg Gly Leu Phe His Ala Ser Leu
            515                 520                 525
Gly Ile Ala Gln Leu Ser Gln Ala Gly Pro Ser Lys Ser Asp Arg Gly
        530                 535                 540
Ser Ser Gln Val Ser Val Thr Ser Thr Val His Val Val Asn Thr Thr
545                 550                 555                 560
Val Val Thr Met Pro Val Pro Met Val Ser Thr Ser Ser Ser Ser Tyr
                565                 570                 575
Thr Thr Leu Leu Pro Thr Leu Glu Lys Lys Arg Lys Arg Cys Gly
            580                 585                 590
Val Cys Glu Pro Cys Gln Gln Lys Thr Asn Cys Gly Glu Cys Thr Tyr
        595                 600                 605
Cys Lys Asn Arg Lys Asn Ser His Gln Ile Cys Lys Lys Arg Lys Cys
        610                 615                 620
Glu Glu Leu Lys Lys Lys Pro Ser Val Val Pro Leu Glu Val Ile
625                 630                 635                 640
Lys Glu Asn Lys Arg Pro Gln Arg Glu Lys Lys Pro Lys Val Leu Lys
                645                 650                 655
Ala Asp Phe Asp Asn Lys Pro Val Asn Gly Pro Lys Ser Glu Ser Met
            660                 665                 670
Asp Tyr Ser Arg Cys Gly His Gly Glu Glu Gln Lys Leu Glu Leu Asn
        675                 680                 685
Pro His Thr Val Glu Asn Val Thr Lys Asn Glu Asp Ser Met Thr Gly
        690                 695                 700
```

-continued

```
Ile Glu Val Glu Lys Trp Thr Gln Asn Lys Lys Ser Gln Leu Thr Asp
705                 710                 715                 720

His Val Lys Gly Asp Phe Ser Ala Asn Val Pro Glu Ala Glu Lys Ser
            725                 730                 735

Lys Asn Ser Glu Val Asp Lys Lys Arg Thr Lys Ser Pro Lys Leu Phe
        740                 745                 750

Val Gln Thr Val Arg Asn Gly Ile Lys His Val His Cys Leu Pro Ala
    755                 760                 765

Glu Thr Asn Val Ser Phe Lys Lys Phe Asn Ile Glu Glu Phe Gly Lys
770                 775                 780

Thr Leu Glu Asn Asn Ser Tyr Lys Phe Leu Lys Asp Thr Ala Asn His
785                 790                 795                 800

Lys Asn Ala Met Ser Ser Val Ala Thr Asp Met Ser Cys Asp His Leu
            805                 810                 815

Lys Gly Arg Ser Asn Val Leu Val Phe Gln Gln Pro Gly Phe Asn Cys
        820                 825                 830

Ser Ser Ile Pro His Ser Ser His Ser Ile Ile Asn His His Ala Ser
    835                 840                 845

Ile His Asn Glu Gly Asp Gln Pro Lys Thr Pro Glu Asn Ile Pro Ser
850                 855                 860

Lys Glu Pro Lys Asp Gly Ser Pro Val Gln Pro Ser Leu Leu Ser Leu
865                 870                 875                 880

Met Lys Asp Arg Arg Leu Thr Leu Glu Gln Val Val Ala Ile Glu Ala
            885                 890                 895

Leu Thr Gln Leu Ser Glu Ala Pro Ser Glu Asn Ser Ser Pro Ser Lys
        900                 905                 910

Ser Glu Lys Asp Glu Glu Ser Glu Gln Arg Thr Ala Ser Leu Leu Asn
    915                 920                 925

Ser Cys Lys Ala Ile Leu Tyr Thr Val Arg Lys Asp Leu Gln Asp Pro
930                 935                 940

Asn Leu Gln Gly Glu Pro Pro Lys Leu Asn His Cys Pro Ser Leu Glu
945                 950                 955                 960

Lys Gln Ser Ser Cys Asn Thr Val Val Phe Asn Gly Gln Thr Thr Thr
            965                 970                 975

Leu Ser Asn Ser His Ile Asn Ser Ala Thr Asn Gln Ala Ser Thr Lys
        980                 985                 990

Ser His Glu Tyr Ser Lys Val Thr Asn Ser Leu Ser Leu Phe Ile Pro
    995                 1000                1005

Lys Ser Asn Ser Ser Lys Ile Asp Thr Asn Lys Ser Ile Ala Gln
    1010                1015                1020

Gly Ile Ile Thr Leu Asp Asn Cys Ser Asn Asp Leu His Gln Leu
    1025                1030                1035

Pro Pro Arg Asn Asn Glu Val Glu Tyr Cys Asn Gln Leu Leu Asp
    1040                1045                1050

Ser Ser Lys Lys Leu Asp Ser Asp Asp Leu Ser Cys Gln Asp Ala
    1055                1060                1065

Thr His Thr Gln Ile Glu Glu Asp Val Ala Thr Gln Leu Thr Gln
    1070                1075                1080

Leu Ala Ser Ile Ile Lys Ile Asn Tyr Ile Lys Pro Glu Asp Lys
    1085                1090                1095

Lys Val Glu Ser Thr Pro Thr Ser Leu Val Thr Cys Asn Val Gln
    1100                1105                1110
```

-continued

Gln Lys Tyr Asn Gln Glu Lys Gly Thr Ile Gln Gln Lys Pro Pro
    1115                1120                1125

Ser Ser Val His Asn Asn His Gly Ser Ser Leu Thr Lys Gln Lys
    1130                1135                1140

Asn Pro Thr Gln Lys Lys Thr Lys Ser Thr Pro Ser Arg Asp Arg
    1145                1150                1155

Arg Lys Lys Lys Pro Thr Val Val Ser Tyr Gln Glu Asn Asp Arg
    1160                1165                1170

Gln Lys Trp Glu Lys Leu Ser Tyr Met Tyr Gly Thr Ile Cys Asp
    1175                1180                1185

Ile Trp Ile Ala Ser Lys Phe Gln Asn Phe Gly Gln Phe Cys Pro
    1190                1195                1200

His Asp Phe Pro Thr Val Phe Gly Lys Ile Ser Ser Ser Thr Lys
    1205                1210                1215

Ile Trp Lys Pro Leu Ala Gln Thr Arg Ser Ile Met Gln Pro Lys
    1220                1225                1230

Thr Val Phe Pro Pro Leu Thr Gln Ile Lys Leu Gln Arg Tyr Pro
    1235                1240                1245

Glu Ser Ala Glu Glu Lys Val Lys Val Glu Pro Leu Asp Ser Leu
    1250                1255                1260

Ser Leu Phe His Leu Lys Thr Glu Ser Asn Gly Lys Ala Phe Thr
    1265                1270                1275

Asp Lys Ala Tyr Asn Ser Gln Val Gln Leu Thr Val Asn Ala Asn
    1280                1285                1290

Gln Lys Ala His Pro Leu Thr Gln Pro Ser Ser Pro Pro Asn Gln
    1295                1300                1305

Cys Ala Asn Val Met Ala Gly Asp Asp Gln Ile Arg Phe Gln Gln
    1310                1315                1320

Val Val Lys Glu Gln Leu Met His Gln Arg Leu Pro Thr Leu Pro
    1325                1330                1335

Gly Ile Ser His Glu Thr Pro Leu Pro Glu Ser Ala Leu Thr Leu
    1340                1345                1350

Arg Asn Val Asn Val Val Cys Ser Gly Gly Ile Thr Val Val Ser
    1355                1360                1365

Thr Lys Ser Glu Glu Glu Val Cys Ser Ser Ser Phe Gly Thr Ser
    1370                1375                1380

Glu Phe Ser Thr Val Asp Ser Ala Gln Lys Asn Phe Asn Asp Tyr
    1385                1390                1395

Ala Met Asn Phe Phe Thr Asn Pro Thr Lys Asn Leu Val Ser Ile
    1400                1405                1410

Thr Lys Asp Ser Glu Leu Pro Thr Cys Ser Cys Leu Asp Arg Val
    1415                1420                1425

Ile Gln Lys Asp Lys Gly Pro Tyr Tyr Thr His Leu Gly Ala Gly
    1430                1435                1440

Pro Ser Val Ala Ala Val Arg Glu Ile Met Glu Asn Arg Tyr Gly
    1445                1450                1455

Gln Lys Gly Asn Ala Ile Arg Ile Glu Ile Val Val Tyr Thr Gly
    1460                1465                1470

Lys Glu Gly Lys Ser Ser His Gly Cys Pro Ile Ala Lys Trp Val
    1475                1480                1485

Leu Arg Arg Ser Ser Asp Glu Glu Lys Val Leu Cys Leu Val Arg
    1490                1495                1500

Gln Arg Thr Gly His His Cys Pro Thr Ala Val Met Val Val Leu

```
              1505                1510                1515
Ile Met Val Trp Asp Gly Ile Pro Leu Pro Met Ala Asp Arg Leu
    1520                1525                1530

Tyr Thr Glu Leu Thr Glu Asn Leu Lys Ser Tyr Asn Gly His Pro
    1535                1540                1545

Thr Asp Arg Arg Cys Thr Leu Asn Glu Asn Arg Thr Cys Thr Cys
    1550                1555                1560

Gln Gly Ile Asp Pro Glu Thr Cys Gly Ala Ser Phe Ser Phe Gly
    1565                1570                1575

Cys Ser Trp Ser Met Tyr Phe Asn Gly Cys Lys Phe Gly Arg Ser
    1580                1585                1590

Pro Ser Pro Arg Arg Phe Arg Ile Asp Pro Ser Ser Pro Leu His
    1595                1600                1605

Glu Lys Asn Leu Glu Asp Asn Leu Gln Ser Leu Ala Thr Arg Leu
    1610                1615                1620

Ala Pro Ile Tyr Lys Gln Tyr Ala Pro Val Ala Tyr Gln Asn Gln
    1625                1630                1635

Val Glu Tyr Glu Asn Val Ala Arg Glu Cys Arg Leu Gly Ser Lys
    1640                1645                1650

Glu Gly Arg Pro Phe Ser Gly Val Thr Ala Cys Leu Asp Phe Cys
    1655                1660                1665

Ala His Pro His Arg Asp Ile His Asn Met Asn Asn Gly Ser Thr
    1670                1675                1680

Val Val Cys Thr Leu Thr Arg Glu Asp Asn Arg Ser Leu Gly Val
    1685                1690                1695

Ile Pro Gln Asp Glu Gln Leu His Val Leu Pro Leu Tyr Lys Leu
    1700                1705                1710

Ser Asp Thr Asp Glu Phe Gly Ser Lys Glu Gly Met Glu Ala Lys
    1715                1720                1725

Ile Lys Ser Gly Ala Ile Glu Val Leu Ala Pro Arg Arg Lys Lys
    1730                1735                1740

Arg Thr Cys Phe Thr Gln Pro Val Pro Arg Ser Gly Lys Lys Arg
    1745                1750                1755

Ala Ala Met Met Thr Glu Val Leu Ala His Lys Ile Arg Ala Val
    1760                1765                1770

Glu Lys Lys Pro Ile Pro Arg Ile Lys Arg Lys Asn Asn Ser Thr
    1775                1780                1785

Thr Thr Asn Asn Ser Lys Pro Ser Ser Leu Pro Thr Leu Gly Ser
    1790                1795                1800

Asn Thr Glu Thr Val Gln Pro Glu Val Lys Ser Glu Thr Glu Pro
    1805                1810                1815

His Phe Ile Leu Lys Ser Ser Asp Asn Thr Lys Thr Tyr Ser Leu
    1820                1825                1830

Met Pro Ser Ala Pro His Pro Val Lys Glu Ala Ser Pro Gly Phe
    1835                1840                1845

Ser Trp Ser Pro Lys Thr Ala Ser Ala Thr Pro Ala Pro Leu Lys
    1850                1855                1860

Asn Asp Ala Thr Ala Ser Cys Gly Phe Ser Glu Arg Ser Ser Thr
    1865                1870                1875

Pro His Cys Thr Met Pro Ser Gly Arg Leu Ser Gly Ala Asn Ala
    1880                1885                1890

Ala Ala Ala Asp Gly Pro Gly Ile Ser Gln Leu Gly Glu Val Ala
    1895                1900                1905
```

```
Pro Leu Pro Thr Leu Ser Ala Pro Val Met Glu Pro Leu Ile Asn
    1910                1915                1920

Ser Glu Pro Ser Thr Gly Val Thr Glu Pro Leu Thr Pro His Gln
    1925                1930                1935

Pro Asn His Gln Pro Ser Phe Leu Thr Ser Pro Gln Asp Leu Ala
    1940                1945                1950

Ser Ser Pro Met Glu Glu Asp Glu Gln His Ser Glu Ala Asp Glu
    1955                1960                1965

Pro Pro Ser Asp Glu Pro Leu Ser Asp Pro Leu Ser Pro Ala
    1970                1975                1980

Glu Glu Lys Leu Pro His Ile Asp Glu Tyr Trp Ser Asp Ser Glu
    1985                1990                1995

His Ile Phe Leu Asp Ala Asn Ile Gly Gly Val Ala Ile Ala Pro
    2000                2005                2010

Ala His Gly Ser Val Leu Ile Glu Cys Ala Arg Arg Glu Leu His
    2015                2020                2025

Ala Thr Thr Pro Val Glu His Pro Asn Arg Asn His Pro Thr Arg
    2030                2035                2040

Leu Ser Leu Val Phe Tyr Gln His Lys Asn Leu Asn Lys Pro Gln
    2045                2050                2055

His Gly Phe Glu Leu Asn Lys Ile Lys Phe Glu Ala Lys Glu Ala
    2060                2065                2070

Lys Asn Lys Lys Met Lys Ala Ser Glu Gln Lys Asp Gln Ala Ala
    2075                2080                2085

Asn Glu Gly Pro Glu Gln Ser Ser Glu Val Asn Glu Leu Asn Gln
    2090                2095                2100

Ile Pro Ser His Lys Ala Leu Thr Leu Thr His Asp Asn Val Val
    2105                2110                2115

Thr Val Ser Pro Tyr Ala Leu Thr His Val Ala Gly Pro Tyr Asn
    2120                2125                2130

His Trp Val
    2135

<210> SEQ ID NO 11
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: "X" = any amino acid

<400> SEQUENCE: 11

Cys Xaa Xaa Cys
1

<210> SEQ ID NO 12
<211> LENGTH: 5469
<212> TYPE: DNA
<213> ORGANISM: Artificial Sequence
<220> FEATURE:
<223> OTHER INFORMATION: synthetic polynucleotide

<400> SEQUENCE: 12
atggactaca aggacgacga tgacaagctc gatggaggat accccctacga cgtgcccgac      60 tacgccggag gactcgacag ccagtttcag gtgcccctgg ccgtccagcc ggacctgcca     120
```

```
ggcctttatg acttccctca gcgccaggtg atggtaggga gcttcccggg gtctgggctc      180
tccatggctg ggagtgagtc ccaactccga ggggtggaga atggtcgaaa gaaacggaaa      240
cggtgtggta cttgtgagcc ctgccggcgg ctggaaaact gtggcgcttg cactagctgt      300
accaaccgcc gcacgcacca gatctgcaaa ctgcgaaaat gtgaggtgct gaagaaaaaa      360
gtagggcttc tcaaggaggt ggaaataaag gctggtgaag gagccgggcc gtggggacaa      420
ggagcggctg tcaagacagg ctcagagctc agcccagttg atggacctgt tccaggtcag      480
atggactcag ggccagtgta ccatggggac tcacggcagc taagcgcctc aggggtgccg      540
gtcaatggtg ctagagagcc cgctggaccc agtctgctgg ggactggggg tccttggcgg      600
gtagaccaaa agcccgactg ggaggctgcc ccaggcccag ctcatactgc tcgcctggaa      660
gatgcccacg atctggtggc ctttcggct gtggccgaag ctgtgtcctc ttatggggcc       720
cttagcaccc ggctctatga aaccttcaac cgtgagatga gtcgtgaggc tgggaacaac      780 agcagggggac cccggccagg gcctgagggc tgctctgctg gcagcgaaga ccttgacaca     840
ctgcagacgg ccctggccct cgcgcggcat ggtatgaaac cacccaactg caactgcgat      900
ggcccagaat gccctgacta cctcgagtgg ctggagggga agatcaagtc tgtggtcatg      960
gaaggagggg aggagcggcc caggctccca gggcctctgc ctcctggtga ggccggcctc     1020
ccagcaccaa gcaccaggcc actcctcagc tcagaggtgc cccagatctc tccccaagag     1080
ggcctgcccc tgtcccagag tgccctgagc attgccaagg aaaaaaacat cagcttgcag     1140
accgccattg ccattgaggc cctcacacag ctctcctctg ccctcccgca gccttctcat     1200 tccaccccc aggcttcttg ccccttcct gaggccttgt cacctcctgc cccttcaga       1260 tctccccagt cttacctccg ggctccctca tggcctgtgg ttcctcctga agagcactca     1320
tcttttgctc ctgatagctc tgccttccct ccagcaactc ctagaactga gttccctgaa     1380
gcctggggca ctgacacccc tccagcaacg ccccggagct cctggcccat gcctcgccca    1440
agccccgatc ccatggctga actggagcag ttgttgggca gcgccagtga ttacatccag     1500
tcagtattca gcggcctga ggccctgcct accaagccca aggtcaaggt ggaggcaccc      1560
tcttcctccc cggccccggc cccatcccct gtacttcaga gggaggctcc cacgccatcc    1620
tcggagcccg acacccacca gaaggcccag accgccctgc agcagcacct ccaccacaag    1680
cgcagcctct tcctagaaca ggtgcacgac acctccttcc ctgctccttc agagccttct    1740
gctcctggct ggtggccccc accaagttca cctgtcccac ggcttccaga cagaccaccc    1800
aaggagaaga agaagaagct cccaacacca gctggaggtc ccgtgggaac ggagaaagct    1860
gcccctggga tcaagcccag tgtccgaaag cccattcaga tcaagaagtc caggccccgg    1920
gaagcacagc cctcttccc acctgtccga cagattgtcc tggaagggct taggtcccca    1980
gcctcccagg aagtgcaggc tcatccaccg gcccctctgc ctgcctcaca gggctctgct    2040
gtgcccctgc cccagaacc ttctcttgcg ctatttgcac ctagtccctc cagggacagc     2100
ctgctgcccc ctactcagga aatgaggtcc cccagcccca tgacagcctt gcagccaggc    2160
tccactggcc ctcttccccc tgccgatgac aagctggaag agctcatccg gcagtttgag    2220
gctgaatttg gagatagctt tgggcttccc ggccccct ctgtgcccat tcaggacccc     2280
gagaaccagc aaacatgtct cccagcccct gagagcccct tgctacccg ttccccaag     2340 caaatcaaga ttgagtcttc gggggctgtg actgtgctct caaccacctg cttccattca    2400
gaggagggag gacaggaggc cacacccacc aaggctgaga acccactcac acccacccct    2460
```

-continued

```
agtggcttct tggagtcacc tcttaagtac ctggacacac ccaccaagag tctgctggac    2520
acacctgcca agagagccca ggccgagttc cccacctgcg attgcgtcga acaaatagtg    2580
gagaaagatg aaggtccata ttatactcac ttgggatctg gccccacggt cgcctctatc    2640
cgggaactca tggaggagcg gtatggagag aaggggaaag ccatccggat cgagaaggtc    2700
atctacacgg ggaaggaggg aaagagctcc cgcggttgcc ccattgcaaa gtgggtgatc    2760
cgcaggcaca cgctggagga gaagctactc tgcctggtgc ggcaccgggc aggccaccac    2820
tgccagaacg ctgtgatcgt catcctcatc ctggcctggg agggcattcc ccgtagcctc    2880
ggagacaccc tctaccagga gctcaccgac accctccgga gtatgggaa ccccaccagc    2940 cggagatgcg gcctcaacga tgaccggacc tgcgcttgcc aaggcaaaga ccccaacacc    3000
tgtggtgcct ccttctcctt tggttgttcc tggagcatgt acttcaacgg ctgcaagtat    3060
gctcggagca agacacctcg caagttccgc ctcgcagggg acaatcccaa agaggaagaa    3120
gtgctccgga gagtttccca ggacctggcc accgaagtcg ctcccctgta caagcgactg    3180
gcccctcagg cctatcagaa ccaggtgacc aacgaggaaa tagcgattga ctgccgtctg    3240
gggctgaagg aaggacggcc cttcgcgggg gtcacggcct gcatggactt ctgtgcccac    3300
gcccacaagg accagcataa cctctacaat gggtgcaccg tggtctgcac cctgaccaag    3360
gaagacaatc gctgcgtggg caagattccc gaggatgagc agctgcatgt tctcccctg    3420 tacaagatgg ccaacacgga tgagtttggt agcgaggaga accagaatgc aaaggtgggc    3480
agcggagcca tccaggtgct caccgccttc ccccgcgagg tccgacgcct gcccgagcct    3540
gccaagtcct gccgccagcg gcagctggaa gccagaaagg cagcagccga gaagaagaag    3600
attcagaagg agaagctgag cactccggag aagatcaagc aggaggccct ggagctggcg    3660
ggcattacgt cggacccagg cctgtctctg aagggtggat tgtcccagca aggcctgaag    3720
ccctccctca aggtggagcc gcagaaccac ttcagctcct tcaagtacag cggcaacgcg    3780
gtggtggaga gctactcggt gctgggcaac tgccggccct ccgacccttg cagcatgaac    3840
agcgtgtact cctaccactc ctactatgca cagcccagcc tgacctccgt caatggcttc    3900
cactccaagt acgctctccc gtcttttagc tactatggct ttccatccag caaccccgtc    3960
ttcccctctc agttcctggg tcctggtgcc tgggggcata gtggcagcag tggcagtttt    4020
gagaagaagc cagacctcca cgctctgcac aacagcctga gccggcccta cggtggtgct    4080
gagtttgccg agctgcccag ccaggctgtt cccacagacg cccaccaccc cactcctcac    4140
caccagcagc ctgcgtaccc aggccccaag gagtatctgc ttcccaaggc cccctactc    4200 cactcagtgt ccagggaccc ctccccttt gcccagagct ccaactgcta caacagatcc    4260
atcaagcaag agccagtaga cccgctgacc caggctgagc ctgtgcccag agacgctggc    4320
aagatgggca agacacctct gtccgaggtg tctcagaatg gaggacccag tcacctttgg    4380
ggacagtact caggaggccc aagcatgtcc cccaagagga ctaacggtgt gggtggcagc    4440
tggggtgtgt ctcgtctggg ggagagtcct gccatcgtcc ctgacaagct cagttccttt    4500
ggggccagct gcctggcccc ttcccacttc acagatggcc agtgggggct gttccccggt    4560
gaggggcagc aggcagcttc ccactctgga ggacggctgc gaggcaaacc gtggagcccc    4620
tgcaagtttg gaacagcac ctcggccttg gctgggccca gcctgactga aagccgtgg    4680 gcgctggggg cagggatt caactcggcc ctgaaaggta gtcctgggtt ccaagacaag    4740
ctgtggaacc ccatgaaagg agaggagggc aggattccag ccgcagggc cagccagctg    4800 gacagggcct ggcagtcctt tggtctgccc ctgggatcca gcgagaagct gtttggggct    4860
```

```
ctgaagtcag aggagaagct gtgggacccc ttcagcctgg aggaggggcc ggctgaggag    4920
cccccccagca agggagcggt gaaggaggag aagggcggtg gtggtgcgga ggaggaagag    4980
gaggagctgt ggtcggacag tgaacacaac ttcctggacg agaacatcgg cggcgtggcc    5040
gtggccccag cccacggctc catcctcatc gagtgtgccc ggcgggagct gcacgccacc    5100
acgccgctta agaagcccaa ccgctgccac cccacccgca tctcgctggt cttctaccag    5160
cacaagaacc tcaaccagcc caaccacggg ctggccctct gggaagccaa gatgaagcag    5220
ctggcggaga gggcacgggc acggcaggag gaggctgccc ggctgggcct gggccagcag    5280
gaggccaagc tctacgggaa gaagcgcaag tgggggggca ctgtggttgc tgagccccag    5340
cagaaagaga agaagggggt cgtccccacc cggcaggcac tggctgtgcc cacagactcg    5400
gcggtcaccg tgtcctccta tgcctacacg aaggtcactg gccctacag ccgctggatc    5460
tagtctaga                                                             5469
```

<210> SEQ ID NO 13
<211> LENGTH: 1820
<212> TYPE: PRT
<213> ORGANISM: Artificial Sequence
<220> FEATURE:
<223> OTHER INFORMATION: synthetic polypeptide

<400> SEQUENCE: 13

```
Met Asp Tyr Lys Asp Asp Asp Asp Lys Leu Asp Gly Gly Tyr Pro Tyr
1               5                   10                  15

Asp Val Pro Asp Tyr Ala Gly Gly Leu Asp Ser Gln Phe Gln Val Pro
                20                  25                  30

Leu Ala Val Gln Pro Asp Leu Pro Gly Leu Tyr Asp Phe Pro Gln Arg
            35                  40                  45

Gln Val Met Val Gly Ser Phe Pro Gly Ser Gly Leu Ser Met Ala Gly
        50                  55                  60

Ser Glu Ser Gln Leu Arg Gly Gly Asp Gly Arg Lys Lys Arg Lys
65                  70                  75                  80

Arg Cys Gly Thr Cys Glu Pro Cys Arg Arg Leu Glu Asn Cys Gly Ala
                85                  90                  95

Cys Thr Ser Cys Thr Asn Arg Arg Thr His Gln Ile Cys Lys Leu Arg
                100                 105                 110

Lys Cys Glu Val Leu Lys Lys Lys Val Gly Leu Leu Lys Glu Val Glu
            115                 120                 125

Ile Lys Ala Gly Glu Gly Ala Gly Pro Trp Gly Gln Gly Ala Ala Val
        130                 135                 140

Lys Thr Gly Ser Glu Leu Ser Pro Val Asp Gly Pro Val Pro Gly Gln
145                 150                 155                 160

Met Asp Ser Gly Pro Val Tyr His Gly Asp Ser Arg Gln Leu Ser Ala
                165                 170                 175

Ser Gly Val Pro Val Asn Gly Ala Arg Glu Pro Ala Gly Pro Ser Leu
                180                 185                 190

Leu Gly Thr Gly Gly Pro Trp Arg Val Asp Gln Lys Pro Asp Trp Glu
            195                 200                 205

Ala Ala Pro Gly Pro Ala His Thr Ala Arg Leu Glu Asp Ala His Asp
        210                 215                 220

Leu Val Ala Phe Ser Ala Val Ala Glu Ala Val Ser Ser Tyr Gly Ala
225                 230                 235                 240

Leu Ser Thr Arg Leu Tyr Glu Thr Phe Asn Arg Glu Met Ser Arg Glu
```

```
            245                 250                 255
Ala Gly Asn Asn Ser Arg Gly Pro Arg Pro Gly Pro Glu Gly Cys Ser
            260                 265                 270

Ala Gly Ser Glu Asp Leu Asp Thr Leu Gln Thr Ala Leu Ala Leu Ala
            275                 280                 285

Arg His Gly Met Lys Pro Pro Asn Cys Asn Cys Asp Gly Pro Glu Cys
            290                 295                 300

Pro Asp Tyr Leu Glu Trp Leu Glu Gly Lys Ile Lys Ser Val Val Met
305                 310                 315                 320

Glu Gly Gly Glu Glu Arg Pro Arg Leu Pro Gly Pro Leu Pro Pro Gly
                325                 330                 335

Glu Ala Gly Leu Pro Ala Pro Ser Thr Arg Pro Leu Leu Ser Ser Glu
            340                 345                 350

Val Pro Gln Ile Ser Pro Gln Glu Gly Leu Pro Leu Ser Gln Ser Ala
            355                 360                 365

Leu Ser Ile Ala Lys Glu Lys Asn Ile Ser Leu Gln Thr Ala Ile Ala
            370                 375                 380

Ile Glu Ala Leu Thr Gln Leu Ser Ser Ala Leu Pro Gln Pro Ser His
385                 390                 395                 400

Ser Thr Pro Gln Ala Ser Cys Pro Leu Pro Glu Ala Leu Ser Pro Pro
                405                 410                 415

Ala Pro Phe Arg Ser Pro Gln Ser Tyr Leu Arg Ala Pro Ser Trp Pro
            420                 425                 430

Val Val Pro Pro Glu Glu His Ser Ser Phe Ala Pro Asp Ser Ser Ala
            435                 440                 445

Phe Pro Pro Ala Thr Pro Arg Thr Glu Phe Pro Glu Ala Trp Gly Thr
450                 455                 460

Asp Thr Pro Pro Ala Thr Pro Arg Ser Ser Trp Pro Met Pro Arg Pro
465                 470                 475                 480

Ser Pro Asp Pro Met Ala Glu Leu Glu Gln Leu Leu Gly Ser Ala Ser
                485                 490                 495

Asp Tyr Ile Gln Ser Val Phe Lys Arg Pro Glu Ala Leu Pro Thr Lys
            500                 505                 510

Pro Lys Val Lys Val Glu Ala Pro Ser Ser Pro Ala Pro Ala Pro
            515                 520                 525

Ser Pro Val Leu Gln Arg Glu Ala Pro Thr Pro Ser Ser Glu Pro Asp
            530                 535                 540

Thr His Gln Lys Ala Gln Thr Ala Leu Gln Gln His Leu His His Lys
545                 550                 555                 560

Arg Ser Leu Phe Leu Glu Gln Val His Asp Thr Ser Phe Pro Ala Pro
                565                 570                 575

Ser Glu Pro Ser Ala Pro Gly Trp Trp Pro Pro Pro Ser Ser Pro Val
            580                 585                 590

Pro Arg Leu Pro Asp Arg Pro Lys Glu Lys Lys Lys Leu Pro
            595                 600                 605

Thr Pro Ala Gly Gly Pro Val Gly Thr Glu Lys Ala Ala Pro Gly Ile
            610                 615                 620

Lys Pro Ser Val Arg Lys Pro Ile Gln Ile Lys Lys Ser Arg Pro Arg
625                 630                 635                 640

Glu Ala Gln Pro Leu Phe Pro Pro Val Arg Gln Ile Val Leu Glu Gly
                645                 650                 655

Leu Arg Ser Pro Ala Ser Gln Glu Val Gln Ala His Pro Pro Ala Pro
            660                 665                 670
```

Leu Pro Ala Ser Gln Gly Ser Ala Val Pro Leu Pro Glu Pro Ser
    675                 680                 685

Leu Ala Leu Phe Ala Pro Ser Pro Ser Arg Asp Ser Leu Leu Pro Pro
690                 695                 700

Thr Gln Glu Met Arg Ser Pro Ser Pro Met Thr Ala Leu Gln Pro Gly
705                 710                 715                 720

Ser Thr Gly Pro Leu Pro Pro Ala Asp Asp Lys Leu Glu Glu Leu Ile
                725                 730                 735

Arg Gln Phe Glu Ala Glu Phe Gly Asp Ser Phe Gly Leu Pro Gly Pro
                740                 745                 750

Pro Ser Val Pro Ile Gln Asp Pro Glu Asn Gln Gln Thr Cys Leu Pro
                755                 760                 765

Ala Pro Glu Ser Pro Phe Ala Thr Arg Ser Pro Lys Gln Ile Lys Ile
    770                 775                 780

Glu Ser Ser Gly Ala Val Thr Val Leu Ser Thr Thr Cys Phe His Ser
785                 790                 795                 800

Glu Glu Gly Gly Gln Glu Ala Thr Pro Thr Lys Ala Glu Asn Pro Leu
                805                 810                 815

Thr Pro Thr Leu Ser Gly Phe Leu Glu Ser Pro Leu Lys Tyr Leu Asp
                820                 825                 830

Thr Pro Thr Lys Ser Leu Leu Asp Thr Pro Ala Lys Arg Ala Gln Ala
                835                 840                 845

Glu Phe Pro Thr Cys Asp Cys Val Glu Gln Ile Val Glu Lys Asp Glu
    850                 855                 860

Gly Pro Tyr Tyr Thr His Leu Gly Ser Gly Pro Thr Val Ala Ser Ile
865                 870                 875                 880

Arg Glu Leu Met Glu Glu Arg Tyr Gly Glu Lys Gly Lys Ala Ile Arg
                885                 890                 895

Ile Glu Lys Val Ile Tyr Thr Gly Lys Glu Gly Lys Ser Ser Arg Gly
                900                 905                 910

Cys Pro Ile Ala Lys Trp Val Ile Arg Arg His Thr Leu Glu Glu Lys
    915                 920                 925

Leu Leu Cys Leu Val Arg His Arg Ala Gly His His Cys Gln Asn Ala
    930                 935                 940

Val Ile Val Ile Leu Ile Leu Ala Trp Glu Gly Ile Pro Arg Ser Leu
945                 950                 955                 960

Gly Asp Thr Leu Tyr Gln Glu Leu Thr Asp Thr Leu Arg Lys Tyr Gly
                965                 970                 975

Asn Pro Thr Ser Arg Arg Cys Gly Leu Asn Asp Asp Arg Thr Cys Ala
                980                 985                 990

Cys Gln Gly Lys Asp Pro Asn Thr Cys Gly Ala Ser Phe Ser Phe Gly
    995                 1000                1005

Cys Ser Trp Ser Met Tyr Phe Asn Gly Cys Lys Tyr Ala Arg Ser
    1010                1015                1020

Lys Thr Pro Arg Lys Phe Arg Leu Ala Gly Asp Asn Pro Lys Glu
    1025                1030                1035

Glu Glu Val Leu Arg Lys Ser Phe Gln Asp Leu Ala Thr Glu Val
    1040                1045                1050

Ala Pro Leu Tyr Lys Arg Leu Ala Pro Gln Ala Tyr Gln Asn Gln
    1055                1060                1065

Val Thr Asn Glu Glu Ile Ala Ile Asp Cys Arg Leu Gly Leu Lys
    1070                1075                1080

```
Glu Gly Arg Pro Phe Ala Gly Val Thr Ala Cys Met Asp Phe Cys
1085                1090                1095

Ala His Ala His Lys Asp Gln His Asn Leu Tyr Asn Gly Cys Thr
1100                1105                1110

Val Val Cys Thr Leu Thr Lys Glu Asp Asn Arg Cys Val Gly Lys
1115                1120                1125

Ile Pro Glu Asp Glu Gln Leu His Val Leu Pro Leu Tyr Lys Met
1130                1135                1140

Ala Asn Thr Asp Glu Phe Gly Ser Glu Glu Asn Gln Asn Ala Lys
1145                1150                1155

Val Gly Ser Gly Ala Ile Gln Val Leu Thr Ala Phe Pro Arg Glu
1160                1165                1170

Val Arg Arg Leu Pro Glu Pro Ala Lys Ser Cys Arg Gln Arg Gln
1175                1180                1185

Leu Glu Ala Arg Lys Ala Ala Ala Glu Lys Lys Lys Ile Gln Lys
1190                1195                1200

Glu Lys Leu Ser Thr Pro Glu Lys Ile Lys Gln Glu Ala Leu Glu
1205                1210                1215

Leu Ala Gly Ile Thr Ser Asp Pro Gly Leu Ser Leu Lys Gly Gly
1220                1225                1230

Leu Ser Gln Gln Gly Leu Lys Pro Ser Leu Lys Val Glu Pro Gln
1235                1240                1245

Asn His Phe Ser Ser Phe Lys Tyr Ser Gly Asn Ala Val Val Glu
1250                1255                1260

Ser Tyr Ser Val Leu Gly Asn Cys Arg Pro Ser Asp Pro Tyr Ser
1265                1270                1275

Met Asn Ser Val Tyr Ser Tyr His Ser Tyr Tyr Ala Gln Pro Ser
1280                1285                1290

Leu Thr Ser Val Asn Gly Phe His Ser Lys Tyr Ala Leu Pro Ser
1295                1300                1305

Phe Ser Tyr Tyr Gly Phe Pro Ser Ser Asn Pro Val Phe Pro Ser
1310                1315                1320

Gln Phe Leu Gly Pro Gly Ala Trp Gly His Ser Gly Ser Ser Gly
1325                1330                1335

Ser Phe Glu Lys Lys Pro Asp Leu His Ala Leu His Asn Ser Leu
1340                1345                1350

Ser Pro Ala Tyr Gly Gly Ala Glu Phe Ala Glu Leu Pro Ser Gln
1355                1360                1365

Ala Val Pro Thr Asp Ala His His Pro Thr Pro His His Gln Gln
1370                1375                1380

Pro Ala Tyr Pro Gly Pro Lys Glu Tyr Leu Leu Pro Lys Ala Pro
1385                1390                1395

Leu Leu His Ser Val Ser Arg Asp Pro Ser Pro Phe Ala Gln Ser
1400                1405                1410

Ser Asn Cys Tyr Asn Arg Ser Ile Lys Gln Glu Pro Val Asp Pro
1415                1420                1425

Leu Thr Gln Ala Glu Pro Val Pro Arg Asp Ala Gly Lys Met Gly
1430                1435                1440

Lys Thr Pro Leu Ser Glu Val Ser Gln Asn Gly Gly Pro Ser His
1445                1450                1455

Leu Trp Gly Gln Tyr Ser Gly Gly Pro Ser Met Ser Pro Lys Arg
1460                1465                1470

Thr Asn Gly Val Gly Gly Ser Trp Gly Val Phe Ser Ser Gly Glu
```

1475                1480                1485

Ser Pro Ala Ile Val Pro Asp Lys Leu Ser Ser Phe Gly Ala Ser
    1490                1495                1500

Cys Leu Ala Pro Ser His Phe Thr Asp Gly Gln Trp Gly Leu Phe
    1505                1510                1515

Pro Gly Glu Gly Gln Gln Ala Ser His Ser Gly Gly Arg Leu
    1520                1525                1530

Arg Gly Lys Pro Trp Ser Pro Cys Lys Phe Gly Asn Ser Thr Ser
    1535                1540                1545

Ala Leu Ala Gly Pro Ser Leu Thr Glu Lys Pro Trp Ala Leu Gly
    1550                1555                1560

Ala Gly Asp Phe Asn Ser Ala Leu Lys Gly Ser Pro Gly Phe Gln
    1565                1570                1575

Asp Lys Leu Trp Asn Pro Met Lys Gly Glu Glu Gly Arg Ile Pro
    1580                1585                1590

Ala Ala Gly Ala Ser Gln Leu Asp Arg Ala Trp Gln Ser Phe Gly
    1595                1600                1605

Leu Pro Leu Gly Ser Ser Glu Lys Leu Phe Gly Ala Leu Lys Ser
    1610                1615                1620

Glu Glu Lys Leu Trp Asp Pro Phe Ser Leu Glu Glu Gly Pro Ala
    1625                1630                1635

Glu Glu Pro Pro Ser Lys Gly Ala Val Lys Glu Glu Lys Gly Gly
    1640                1645                1650

Gly Gly Ala Glu Glu Glu Glu Glu Leu Trp Ser Asp Ser Glu
    1655                1660                1665

His Asn Phe Leu Asp Glu Asn Ile Gly Gly Val Ala Val Ala Pro
    1670                1675                1680

Ala His Gly Ser Ile Leu Ile Glu Cys Ala Arg Arg Glu Leu His
    1685                1690                1695

Ala Thr Thr Pro Leu Lys Lys Pro Asn Arg Cys His Pro Thr Arg
    1700                1705                1710

Ile Ser Leu Val Phe Tyr Gln His Lys Asn Leu Asn Gln Pro Asn
    1715                1720                1725

His Gly Leu Ala Leu Trp Glu Ala Lys Met Lys Gln Leu Ala Glu
    1730                1735                1740

Arg Ala Arg Ala Arg Gln Glu Glu Ala Ala Arg Leu Gly Leu Gly
    1745                1750                1755

Gln Gln Glu Ala Lys Leu Tyr Gly Lys Lys Arg Lys Trp Gly Gly
    1760                1765                1770

Thr Val Val Ala Glu Pro Gln Gln Lys Glu Lys Lys Gly Val Val
    1775                1780                1785

Pro Thr Arg Gln Ala Leu Ala Val Pro Thr Asp Ser Ala Val Thr
    1790                1795                1800

Val Ser Ser Tyr Ala Tyr Thr Lys Val Thr Gly Pro Tyr Ser Arg
    1805                1810                1815

Trp Ile
    1820

<210> SEQ ID NO 14
<211> LENGTH: 18
<212> TYPE: DNA
<213> ORGANISM: Artificial Sequence
<220> FEATURE:
<223> OTHER INFORMATION: synthetic polynucleotide

```
-continued

<400> SEQUENCE: 14
cccaaagagg aagaagtg                                                  18

<210> SEQ ID NO 15
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 15
gcagtcaatc gctatttc                                                  18
```